United States Patent
Yokoi et al.

(10) Patent No.: US 6,793,885 B1
(45) Date of Patent: Sep. 21, 2004

(54) BLOOD TEST CONTAINER

(76) Inventors: Masayuki Yokoi, Kusatsu (JP);
Jun-ichiro Shinoda, Kyoto (JP);
Junzou Shibata, Kameoka (JP); Mie Matsumoto, Osaka (JP); Kazuo Shimmura, Osaka (JP); Hironobu Isogawa, Tokuyuama (JP)

( * ) Notice: Subject to any disclaimer, the term of this patent is extended or adjusted under 35 U.S.C. 154(b) by 0 days.

(21) Appl. No.: 09/508,098
(22) PCT Filed: Sep. 9, 1998
(86) PCT No.: PCT/JP98/04033
§ 371 (c)(1), (2), (4) Date: Mar. 16, 2000
(87) PCT Pub. No.: WO99/14593
PCT Pub. Date: Mar. 25, 1999

(30) Foreign Application Priority Data

Sep. 16, 1997 (JP) ............................................. 9-250942
Nov. 7, 1997 (JP) ............................................. 9-305559
Jan. 21, 1998 (JP) ........................................... 10-009579

(51) Int. Cl.[7] ............................................. G01N 33/48
(52) U.S. Cl. ........................... 422/58; 422/61; 422/102; 436/63; 436/68; 436/69
(58) Field of Search ........................... 422/58, 61, 101, 422/102, 104; 436/63, 68, 69, 910

(56) References Cited

U.S. PATENT DOCUMENTS

| | | |
|---|---|---|
| 5,455,009 A | 10/1995 | Vogler et al. |
| 5,533,518 A | 7/1996 | Vogler |

FOREIGN PATENT DOCUMENTS

| | | |
|---|---|---|
| JP | 63-181861 | 11/1988 |
| JP | 04142442 | 5/1992 |
| JP | 7-167858 | 7/1995 |
| JP | 7-294517 | 11/1995 |

OTHER PUBLICATIONS

Abstract of Japanese Patent Publ. No. 07128330; dated May 19, 1995.
Abstract of Japanese Patent Publ. No. 05288747; dated Nov. 2, 1993.
Abstract of Japanese Patent Publ. No. 05340939; dated Dec. 24, 1993.

Primary Examiner—Lyle A. Alexander

(57) ABSTRACT

A blood test container which facilitate the procedures starting from blood collection and ending with measurement of various components present in the blood while eliminating a risk for a tester to come into contact with the blood. A blood test container 1 having a closed-bottom tubular container 2, a closed-bottom second tubular container having a diameter smaller than that of the tubular container 2 for accommodation therein, and a blood test reagent 3 secured onto at least one of an inner face of the tubular container and an outer face of the second tubular container.

14 Claims, 34 Drawing Sheets

(a)

(b)

(a)

(b)

BLOOD TEST CONTAINER

TECHNICAL FIELD

The present invention relates to a blood test container for use in clinical examinations or testing of human and animals, and more particularly to a blood test container by which a whole procedure starting from blood collection and ending with measurement of blood components can be carried out with the use of a single container.

BACKGROUND ART

The blood component testing as heretofore practiced in clinical examinations and the like is accomplished according to the following procedure. First, blood is collected by using an injector or a vacuum blood-collecting tube. Next, the blood either transferred into a test tube or introduced into the blood-collecting tube is centrifuged to separate serum or plasma and solid matter. Subsequently, the serum or plasma separated is distributed into separately-prepared test containers for measurements.

An equipment for carrying out such measurements is commercially available, for example, under the product name "ORTHO HCV.AB QUICKPACK" from Orthoclinical Diagnostics Co., Ltd. With the use of this testing equipment, HCV antigen screening test can be performed, for example, after serum or plasma is dripped on a reagent of the testing equipment such as by a dropping pipet.

However, the aforementioned conventional test method has required a tester to remove a cover from the blood-collecting tube and distribute the blood into metering cups during the blood collection and measurement. Thus, several opportunities have existed for the tester to contact the blood. This has imposed a risk for the tester to acquire infectious HIV, hepatitis and the like.

It is an object of the present invention to provide a blood test container and a blood test method which can facilitate the practice of a series of procedures starting from blood collection and ending with measurement of various blood components while reducing the chance for the tester to contact the blood.

DISCLOSURE OF THE INVENTION

The blood test container according to the present invention includes a bottom-closed tubular container and a blood test reagent fixedly accommodated in the tubular container.

For the blood test container according to the present invention which secures the test reagent within the bottom-closed blood test container, (1) the blood or its component (referring to serum or plasma previously separated from the blood) is introduced into the tubular container where it is allowed to contact the blood test reagent, or alternatively, (2) the blood is introduced into the tubular container and subsequently centrifuged so that the separated blood component, such as serum or plasma, is allowed to contact the blood test reagent. Therefore, a series of procedures from collection till measurement of the blood can be carried out without the occurrence for a tester to contact the blood.

The blood test reagent may be secured onto an inner face of the tubular container, either directly or indirectly with the aid of other supplemental members. Alternatively, the blood test reagent may be secured onto an outer surface of an inner tubular container, a second tubular container, a tubular member or the like, accommodated within the tubular container.

The "securement of the test reagent onto the inner face or "securement onto the outer face", as used in describing the present invention, is not limited to the configurations whereby the test reagent is literally secured onto the inner or outer face, and encompasses configurations whereby a liquid-form test reagent is located in contact with the inner or outer face and configuration whereby a powder-form test reagent is located in contact with the inner or outer face. Illustrating typical examples of such configurations of the blood test container, the liquid- or powder-form test reagent is located between the tubular container and any one of the inner tubular container, second tubular container and tubular member accommodated within the tubular container to contact therewith.

In accordance with the invention, the blood test container according to the present invention further includes a contact control structure effective to normally prevent the contact of blood introduced in the container with the test reagent and, when centrifuged, allow a blood component to successfully contact the test reagent. In the invention, the contact control structure operates such that it initially prevents the blood introduced into the tubular container from contacting the test reagent but, when centrifuged, permits the separated blood component to contact the test reagent.

In accordance with the invention, the aforementioned contact control structure includes an inner container portion extending along an inner face toward a bottom of said tubular container and perforated at its bottom to have a hole, and a solid member accommodated in the inner container portion for closing the hole and configured to fall down through the hole when centrifuged. Also, the blood test reagent is provided onto an inner face of the tubular container and/or an outer face of the inner container portion. Due to the presence of the solid member which closes the bottom hole of the inner container portion, the blood, when introduced into the tubular container, is initially retained to stay within the tubular container. As centrifuging is subsequently applied, the solid member is caused to fall down and the blood starts to build up in the bottom of the tubular container. After centrifugation, the separated serum or plasma is brought into contact with the test reagent.

In accordance with the invention, the contact control structure includes an open-ended tubular member accommodated in the tubular container and an annular member radially extending between the outer face of the tubular member and the inner face of the tubular container to contact therewith. The annular member is positioned to initially locate below the test reagent. Also, the blood test reagent is secured onto at least one of the inner face of the tubular container and the outer face of the tubular member. This construction permits the blood when introduced into the tubular member to flow through the bottom opening of the tubular member into the bottom of the tubular container. However, the annular member blocks the blood which is accordingly prevented from reaching to contact with the test reagent. When centrifuged, the blood in the tubular member is forced to move downward and then upward along the circumferential surface of the tubular member, whereby the annular member is pushed upward. Also, the blood, when centrifuged, is separated into serum or plasma and solid matter and the separated serum or plasma is brought into contact with the test reagent.

In accordance with the invention, the contact control structure includes an open-ended tubular member accommodated in the tubular container and having a bottom end brought into contact with an interior bottom face of the tubular container, and a pressing means for pressing the tubular member against the interior bottom face of the tubular container so that the blood introduced into the tubular member is prevented from leaking therefrom but, when centrifuged, a component of the blood is permitted to leak therefrom. Also, the blood test reagent is secured onto at least one of the inner face of the tubular container and the outer face of the tubular member. Since the pressing means acts to press the bottom end of the tubular member against the interior bottom face of the tubular container, the blood is initially prevented from leaking to leave the tubular member. When centrifuged, the blood is caused to leak from the tubular member while separated into serum or plasma and solid matter. As a result, the serum or plasma separated is brought into contact with the test reagent.

In accordance with the invention, the contact control structure includes an open-ended tubular member secured onto the inner face of the tubular container, and a solid member secured adjacent a bottom end of the tubular member for closing a bottom opening of the tubular member and adapted to fall through the bottom opening when centrifuged. Also, the test reagent is secured within the tubular member to locate at a position above the solid member. In an initial condition where the test reagent is placed within the tubular member and the bottom opening of the tubular member is closed by the solid member, the blood when introduced into the tubular container is prevented from contacting the test reagent. The subsequent centrifugation causes the solid member to fall down while separating the blood into serum or plasma and solid matter. The falling of the solid member permits the separated serum or plasma to move into the tubular member and contact the test reagent.

In accordance with the invention the blood test container according to the invention, the inner and outer peripheral surfaces of the annular member are brought into abutment against the outer face of the tubular member and the inner face of the tubular container, respectively, with the aid of paraffin of the formula $C_nH_{2n+2}$ (where n is 18–22, preferably 22–24). In an initial condition, the contact of blood with the test reagent is blocked by the intervention of the annular member. The blood, when collected and then centrifuged, is separated into serum or plasma and solid matter. The paraffin, when subsequently heated to a temperature of not below its melting point, is caused to melt. This permits the annular member to freely move vertically. As a result, the serum or plasma is allowed to push the annular member upward and reach to contact the test reagent. That is, the application of heat after centrifugation results in bringing the serum or plasma into contact with the test reagent.

For the blood test container according to the invention, the contact control structure includes an open-ended tubular member having a smaller diameter than the tubular container and accommodated in the tubular container. The blood test reagent is secured onto at least one of the inner face of the tubular container and the outer face of the tubular member. Also, a space between the tubular container and the tubular member, inclusive of a region where the blood test reagent is secured, is sealed by a sealing member comprised of thixotropic material having a viscosity of 5,000–500,000 centipoise at 25° C. Due to the presence of the sealing member which seals the space, the blood when introduced into the tubular member is prevented from flowing straight into the space. Following centrifugation causes the thixotropic sealing member to shift in location toward a bottom of the tubular container, thereby unsealing the space. When the blood test container is subsequently turned upside down or slanted, the separated serum or plasma is allowed to enter the space where it contacts the blood test reagent for reaction therewith.

For the blood test container according to the invention, the aforementioned contact control structure includes a flexible inner resin tube accommodated in the tubular container and having an outer peripheral surface portion brought into circumferential contact with an inner face of the tubular container. One end portion of the inner tube is dimensioned to have an outer diameter smaller than an inner diameter of the tubular container so that its outer peripheral surface is separated from the inner face of the tubular container to define a space therebetween. The blood test container further includes a communicating member disposed within the space so as to be moveable. Also, the blood test reagent is located within the space and secured onto the inner face of the tubular container or onto the outer face of the inner tube.

In accordance with the invention, the blood is introduced into the inner tube. In the case where the inner tube is opened at its bottom, the blood when introduced is brought straight into a bottom of the tubular container. In the alternative case where the inner tube is closed at its bottom, the blood is retained within the inner tube.

In either case, the blood is initially prevented from reaching to contact the test reagent, due to the presence of the circumferential contact of the inner tube peripheral portion and the tubular container inner face that keeps the blood away from the space within which the test reagent is located. When the blood test container is subsequently centrifuged, the communicating member is forced to move toward the circumferential contact region and finally release the circumferential contact of the outer peripheral surface portion of the inner tube and the inner face of the tubular container. As a result, the separated serum or plasma is allowed to enter the space where it contacts the blood test reagent for reaction therewith.

For the blood test container according to the invention, the inner tube may specifically be opened at its top and bottom ends and an outer diameter of its top end may be made smaller than an inner diameter of the tubular container. In this case, the blood when introduced into the inner tube is allowed to pass through the bottom opening of the inner tube down into a bottom of the tubular container. The inner tube has an upper peripheral surface portion terminating in its top end, which is spaced from the inner face of the tubular container to provide a space therebetween. The test reagent is secured within this space. The inner tube also has a lower peripheral surface portion terminating in its bottom end, which is brought into circumferential contact with the inner face of the tubular container. Accordingly, the blood when introduced into the inner tube is initially prevented from contacting the test reagent. When centrifuged, the communicating member is caused to move downward and act to release the circumferential contact of the lower peripheral surface portion of the inner tube and the inner face of the tubular container. As a result, the centrifugally-separated serum or plasma is brought into contact with the blood test reagent.

For the blood test container according to the invention, the inner tube may be closed at its bottom and an outer diameter of a near bottom portion of the inner tube may be made smaller than an inner diameter of the tubular container to space a lower peripheral surface portion of the inner tube from the inner face of the tubular container. The remaining portion, i.e., the upper peripheral surface portion of the inner tube is held in circumferential contact with the inner face of the tubular container. Accordingly, the blood is prevented from reaching to contact the test reagent. After collection of the blood, the blood test container is turned upside down and subsequently centrifuged. The centrifugation serves to separate serum or plasma from the blood. Concurrently, the communicating member is caused to move toward the upper portion of the tubular container, i.e., downwardly within the reversed blood test container. The communicating member while moved acts to release the circumferential contact of the upper peripheral surface portion of the inner tube with the inner face of the tubular container. The separated serum or plasma is then allowed to enter the space defined between the lower peripheral surface portion of the inner tube and the inner face of the tubular container and contact the blood test reagent.

The blood test container according to the invention further includes a bottom-closed second tubular container having a diameter smaller than that of the tubular container for its accommodation within the tubular container. The blood test reagent is secured onto at least one of the inner face of the tubular container and the outer face of the second tubular container. The test reagent in the form of a liquid or powder may be placed between the tubular container and the second tubular container, as stated earlier. After introduction of the blood into the second tubular container, a stopper may be placed on the blood test container to close its top opening, for example. When the blood test container is subsequently turned upside down or slanted, the blood is caused to leave the second tubular container and enter the space between the tubular container and the second tubular container. Within the space, the blood contacts and reacts with the blood test reagent secured onto the inner face of the tubular container and/or the outer face of the second tubular container. The reaction results can be observed visually or measured by using a measuring equipment such as a spectrophotometer.

In the blood test container according to the invention, the second tubular container is provided at its bottom with a plurality of through-holes having diameters of 0.1–10 μm. Also, the blood test reagent is secured onto at least one of the inner face of the tubular container and the outer face of the second tubular container. The blood, when introduced into the second tubular container, is initially retained within the second tubular container. When needed, the blood test container is subsequently centrifuged. Then, the serum or plasma present in the blood is forced to pass through the hole and starts to build up in the bottom of the tubular container. After centrifugation, the serum or plasma can thus be brought into contact with the test reagent.

In accordance with the invention, the second tubular container is provided at its bottom with a plurality of through-holes having diameters of 10–400 μm, and a porous bottom region including the plurality of through-holes is located at a position below the test reagent. Also, the blood test reagent is secured onto at least one of the inner face of the tubular container and the outer face of the second tubular container. The blood, when introduced into the second tubular container, is allowed to grudually leak through the though-holes into the tubular container. Accordingly, the blood introduced into the second tubular container is restricted from flowing rapidly into the outer tubular container. The gradual build-up of the blood in the tubular container retards the contact thereof with the test reagent. When needed, the blood test container is subsequently centrifuged. Then, the blood, while separated into serum or plasma and solid matter, is transferred from the second tubular container into the outer tubular container. As a result, the serum or plasma can be brought into contact with the test reagent.

For the blood test container according to the invention, the space between the tubular container and the second tubular container, inclusive of a region where the blood test reagent is secured, is sealed by a sealing member comprised of water-soluble material. When the blood is collected in or distributed into the blood test container, the blood is thus restricted from immediately flowing into the space between the inner face of the tubular container and the outer face of the second tubular member. When in use, the blood is introduced into the second tubular container. After optional centrifugation, the blood test container is turned upside down or slanted, so that a blood sample such as serum or plasma is brought into contact with the aforementioned water-soluble material. In a while after their contact, the water-soluble material is caused to dissolve. The blood sample is then allowed to enter the space between the tubular container and the second tubular container and contact the blood test reagent for reaction therewith.

For the blood test container according to the invention, the space between the tubular container and the second tubular container, inclusive of a region where the blood test reagent is secured, is sealed by a sealing member fabricated from material having a melting point of not below 40° C. The blood when introduced into the blood test container is thus prevented from accidentally flowing straight into the space defined between the tubular container and the second tubular container. After the blood sample is introduced into the second tubular container, the blood test container is centrifuged when needed. The blood test container is then turned upside down or slanted. The sealing member, when subsequently heated to a temperature of above its melting point, is caused to melt. The blood sample is then allowed to enter the space where it contacts the blood test reagent and a reaction thereof is initiated.

The blood test container according to the invention includes a stopper. The stopper has a first stopper portion terminating in its bottom end and having a relatively small diameter dimensioned to be press fitted into a top opening of the second tubular container, and a second stopper portion upwardly neighboring the first stopper portion and configured to be press fitted into a top opening of the tubular container. The first stopper portion is provided on its peripheral surface with a groove extending upwardly from its bottom end to points which are located above its peripheral surface region that is to be press fitted in the second tubular portion. The second tubular container is provided on its inner face with a groove extending downwardly from its top end to points which are located below its inner face region that receives the first stopper portion.

When in use, the blood is introduced into the second tubular container, with the stopper being either held attached to or detached from the blood test container. When detached, the stopper is reattached to the blood test container after the blood introduction. In this instance, attachment of the stopper is accomplished in such a way to stagger the groove on the first stopper portion from the groove on the second tubular container. This prevents the blood from entering the aforementioned space. When in measurement, the blood test container is centrifuged, when needed. Subsequently, the stopper is rotated to a position where the groove on the first stopper portion comes into alignment with the groove provided on the inner face of the second tubular container, thereby assuring the provision of a flow path communicated with the space between the second tubular container and the tubular container. When the blood test container is then turned upside down or slanted, the blood is caused to pass through the flow path into the space where it is contacted with the blood test reagent.

For the blood test container according to the invention, a top opening of the second tubular container is sealed by a polymer or metal film having a thickness up to 100 μm. When in measurement, the polymer or metal film is partially broken to provide an open region through which a tubular member is inserted for introduction of the blood into the second tubular container. The blood while distributed is thus prevented from entering the space between the second tubular container and the tubular container. Next, the blood test container is centrifuged, when needed, and then turned upside down. This allows the blood sample to enter the space between the second tubular container and the tubular container and react with the blood test reagent.

For the blood test container according to the invention, the top opening of the second tubular container is sealed by a film formed of material having a melting point of not below 40° C. This film is partly broken to provide an open region through which a tubular member or the like is inserted for introduction of the blood sample into the second tubular container. This accordingly prevents the blood sample from flowing straight into the space between the second tubular container and the tubular container. Subsequently, the blood test container is centrifuged when needed, turned upside down or slanted, and then heated to a temperature of not below 40° C. This results in melting the film formed of material having a melting point of not below 40° C. The blood sample is then brought immediately into the space between the tubular container and the second tubular container, where it contacts the blood test reagent for reaction therewith.

In accordance with the invention, the blood test container as includes a serum or plasma separating medium accommodated in the second tubular container. Accordingly, the centrifugation steadily separates the serum or plasma from the blood and bring the separated serum or plasma into contact with the blood test reagent for reaction therewith.

The blood test container according to the invention includes a bottom-closed second tubular container which has a diameter smaller than that of the tubular container and is accommodated in the tubular container. The second tubular container is provided at its bottom with a downwardly-projecting trap portion for trapping erythrocyte and adjacent the trap portion with a hemocyte separating portion with a plurality of through-holes having diameters of 0.1–20 μm.

When in use, a blood sample is introduced into the second tubular container. The subsequent centrifugation causes serum or plasma to pass through the through-holes to outside the trap portion. However, the hemocyte, because of its high specific gravity, is retained to stay within the trap portion. As a result, only the serum or plasma is allowed to leave the trap portion to enter the space between the second tubular container and the tubular container and contact the blood test reagent. It should be understood here that the centrifuging operation is not always required. In an exemplary case where the blood is vacuum collected by reducing the interior pressure of the blood test container, this pressure reduction creates a suction force which acts to pass the blood sample through the trap portion to thereby filter the serum or plasma.

In the blood test container according to the invention, the second tubular container is provided at its bottom with a plurality of through-holes. A layer consisting of 0.1–200 μm hydrophilic fine particles is further placed to overlie the through-holes. When in use, the blood is first introduced into the second tubular container. When subsequently centrifuged, for example, the serum or plasma is induced to pass through the layer consisting of 0.1–200 μm hydrophilic fine particles and through the through-holes into the space between the second tubular container and the tubular container. On the other hand, the hemocyte is retained within the second tubular container to stay over the hydrophilic fine particle layer. As a result, the serum or plasma alone can be brought into contact with the blood test reagent secured onto the inner face of the tubular container and/or the outer face of the second tubular container. The above centrifuging operation is not essential. For example, when the blood is vacuum collected by reducing the interior pressure of the blood test container, the pressure reduction creates a suction force which acts to pass the blood sample through the hydrophilic fine particle layer to thereby filter the serum or plasma.

In accordance with the invention, the second tubular container of the blood test container according to the invention comprises a tubular member opened at it both ends and a bottom member secured onto the bottom end of the tubular member and having a plurality of through-holes. That is, the plurality of through-holes can be provided in the bottom of the second tubular container of the blood test container according to the invention by perforating the closed bottom of the tubular container, or alternatively, by securing a perforated bottom member onto the open bottom of the tubular member.

In accordance with the invention, the second tubular container of the blood test container according to the invention has a hole at its bottom. This hole is closed by a water-soluble cover secured onto the bottom of the second tubular container.

For the blood test container according to the invention, when the blood is introduced into the second tubular container, it is initially prevented from contacting the blood test reagent, due to the presence of the water-soluble cover which closes the bottom hole of the second tubular container. However, the water-soluble cover has a tendency to dissolve into the water content either in the blood or in the serum or plasma separated when the blood is centrifuged. Accordingly, either with the lapse of time or after centrifugation, the water-soluble cover material is caused to dissolve, whereby the blood, serum or plasma is permitted to flow into the space between the second tubular container and the outer tubular container and contact the blood test reagent for reaction therewith.

In accordance with the invention, the second tubular container of the blood test container according to the invention also has a hole at its bottom. A metal or magnet cover is placed within the second tubular container in such a fashion as to close the aforementioned hole. Accordingly, when the blood is introduced into the second tubular container, its contact with the blood test reagent is prevented, because of the intervention of the water-soluble cover which closes the bottom hole of the second tubular container.

When in measurement, the cover member, if formed of a metal, is magnetically moved from outside by using an external magnet and, if formed of a magnet, by using an external metal or magnet, so that the bottom hole of the second tubular container is caused to expose. As a result, the blood introduced into the second tubular container or the serum or plasma separated from the introduced blood by the following centrifugation is allowed to pass through the bottom hole of the second tubular container and enter the space between the second tubular container and the outer tubular container. This results in bringing the blood, serum or plasma into contact with the blood test reagent for reaction therewith.

In accordance with the invention, as the blood test reagent accommodated in the blood test container according to the invention is partly exposed. The remaining portion of the test reagent is covered with a coating layer so that its contact with the blood is prevented. This configuration serves to suppress undesired swelling of the blood test reagent and thus eases ascertainment of test results.

In accordance with the invention the blood test container has a sliding switch is mounted, for vertical movement, to a side wall of the tubular container in such a manner as to grip the side wall. The blood test reagent is secured to a sliding switch portion located within the tubular container.

Accordingly, after introduction of the blood into the tubular container, the blood test reagent can be brought into contact with the introduced blood for reaction therewith by operating the sliding switch to move the blood test reagent downwardly.

That is, the contact of the blood with the blood test reagent can be initially prevented by selecting a volume of the blood introduced such that its level is located in elevation below a bottom edge of the blood test reagent. Also, when in measurement, the blood test reagent can be immersed in the blood, serum or plasma for contact therewith simply by operating the sliding switch.

In accordance with the invention the blood test container further includes a tube having a smaller diameter than the tubular container and accommodated in the tubular container. The tube has a bottom end located at a position below the lowest position that the sliding switch can assume. When in measurement, the blood is introduced into the tube. Since the bottom end of the tube is located at a position below the lowest position that the sliding switch can assume, the blood introduced is hardly allowed to adhere to the sliding switch mounted on the side wall of the tubular container. Accordingly, in an exemplary case where the tubular container is provided with an elongated cutout or the like for vertical movement of the sliding switch therealong, the blood is prevented from leaking through the cutout to outside.

Preferably, the aforementioned tube is located axially centrally of the tubular container. While not intended to limit the invention, the following techniques (1)–(3) can be utilized to locate the tube at such a position. (1) A lid member is provided closing a top opening of the tubular container and the top end of the tube is secured onto a bottom face of the lid member as by an adhesive. (2) A stopper is fitted into the top opening of the tubular container and the top end of the tube is secured onto a bottom face of the stopper. The securement can be achieved with the aid of an adhesive or by threading the top end of the tube into the stopper. (3) Engaging means is provided for engageably suspending the the top end of the tube from the open end of the tubular container.

A blood test container according to the invention further includes a closed-bottom second tubular container arranged to accommodate the tubular container mounting the sliding switch, as well as a stopper provided to simultaneously close respective top openings of those two tubular containers. Also, those two tubular containers are both reduced in interior pressure. The second tubular container may be detached either after the blood is collected according to a vacuum blood-collecting technique or, when needed, after the serum or plasma is centrifugally separated from the blood. The measurement can be accomplished in the same manner as used for the blood test container. A series of procedures from blood collection till measurement of various blood components can thus be readily practiced while eliminating the chance for the tester to contact the blood.

In accordance with the invention the blood test container according to the invention is reduced in interior pressure. This allows the blood to be readily introduced into the blood test container according to a vacuum blood-collecting technique.

In accordance with the blood test method, the blood test can be readily accomplished by introducing the blood into the blood test container and allowing the blood or its component to contact the aforementioned blood test reagent.

In accordance with the blood test method, the blood test can be readily accomplished by introducing the blood into the blood test container, centrifuging the blood and then allowing a component of the blood to contact the blood test reagent. The blood component, as used herein, may be serum or plasma, for example. The blood test container, includes a closed-bottom tubular container and a test reagent for immunochromatography fixed within said tubular container. In accordance with the blood test container, a portion of said test reagent for immunochromatography is exposed and the remaining portion thereof is covered with a protective layer so that the contact of the test reagent for immunochromatography with blood or the like is prevented at the remaining portion.

BRIEF DESCRIPTION OF THE DRAWINGS

FIG. 49(a) is its sectional view when the blood is introduced thereinto and FIG. 49(b) is its sectional view when the blood, after centrifugation, is measured.

FIG. 49(b) is its sectional view when the blood, after centrifugation, is measured.

FIG. 51(a) is its sectional view when the blood is introduced thereinto and FIG. 51(b) is its transverse sectional view when the blood, after centrifugation, is measured.

FIG. 52(a) is its transverse sectional view when the blood is introduced thereinto and FIG. 52(b) is its transverse sectional view when the blood, after centrifugation, is measured.

FIG. 56(a) is a sectional view showing its initial condition and FIG. 56(b) is a transverse sectional view showing its condition after it was vigorously centrifuged.

FIG. 57(a) is a sectional view showing its condition where the serum and solid matter were separated from each other and FIG. 57(b) is a transverse sectional view showing its condition after it was vigorously centrifuged.

FIG. 58(a) is a transverse sectional view which explains the shifting in location of the communicating member when the container is vigorously centrifuged and FIG. 58(b) is a transverse sectional view showing its condition after it was vigorously centrifuged.

FIG. 59(a) is a sectional view showing its initial condition and FIG. 59(b) is a transverse sectional view showing its condition where the blood was introduced thereinto.

FIG. 61(a) is a transverse sectional view which explains the shifting in location of the communicating member by centrifugation and FIG. 61(b) is a transverse sectional view showing its condition after centrifuged.

BEST MODES FOR CARRYING OUT THE INVENTION

Exemplary constructions of the blood test container of the present invention will be now described with referece to the drawings.

Figure 1:
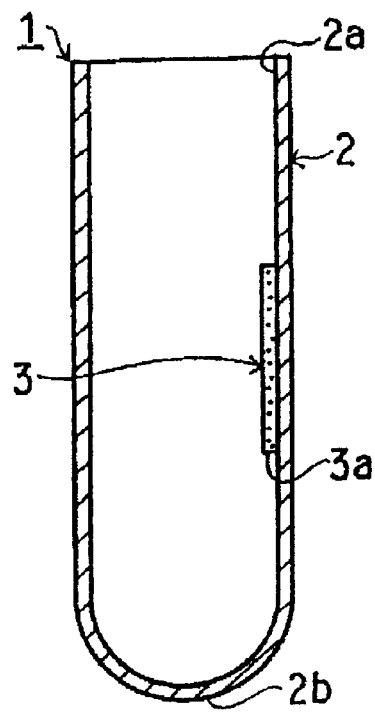
FIG. 1 is a transverse sectional view, showing one embodiment of the blood test container in accordance with the present invention.

FIG. 1 is a sectional view, showing a blood test container in accordance with the present invention. A blood test container 1 has a closed-end tubular container 2, and a blood test reagent 3 secured onto an inner surface of the tubular container 2. The tubular container 2 may be made from suitable materials, such as a synthetic resin and glass, preferably from transparent materials which permit visual inspection of an interior of the tubular container 2. Although illustrated in FIG. 1 as having a circular cross section, the tubular container 2 may be configured to have a polygonal cross section such as a triangle or rectangle, or alternatively, another arbitraty-shaped cross section.

The test reagent 3 may be of any suitable type for use in the measurement of components present in serum or plasma. The test reagent 3 is preferably in the form of solid for its easy securement onto the inner surface of the tubular container 2. However, any viscoelestic test reagent which can be secured somehow onto the the inner surface of the tubular container 2 may also be used. As stated above, the test reagent 3 may be in the form of a liquid or powder, or in the form of being coated on or adsorbed by an insoluble carrier. The type of the test reagent 3 is not particularly limited, so long as its contact with blood components allows the detection or quantitative determination thereof by visual, calorimetric, fluorometric or reflection spectral analysis.

Examples of the test reagents 3 include 1) those, like immunochromatography for detection of hepatitis B antigens, which are used, for component determination, in the form of being included in a film-, disc- or stick-form medium, such as a test paper, cloth, nitrocellulose membrane or glass fiber (test paper or the like may be at its surface covered with a film); 2) liquid-form reagents such as liquid-form pH indicators or liquid-form reagents for measurement of biochemistry- or immunity-associated items; 3) immunological reagents such as TIA and the like utilizing freeze-dried antibodies, enzymes or proteins, or powder-form reagents utilizing chemical substances and the like; 4) reagents such as antibodies, proteins, chemical substances or the like in the form of being coated on a wall surface; 5) liquid- or powder-form reagents in the form of being adsorbed by latex particles or colloidal particles of metals. More specifically, the class 1) is illustrated by reagents for detection of HBs antigen (product name: Quick Chaser HBsAg, manufactured by Mizuho Meddy Co., Ltd., product name: Dyna Screen HBsAg, manufacture by Dynabbot Co., Ltd.). The class 2) is illustrated by a phenolphthalein solution and BTB solution.

Illustrative of the class 3) are TIA reagents utilizing freeze-dried antibodies such as CRP, RF and the like.

Illustrative of the class 4) are chromoreagents or enzymes fixed onto needle-like glass fibers, and antigens or antibodies directly coated on a container inner surface.

Illustrative of the class 5) are liquid-form reagents in the form of antigens or antibodies held by synthesized polymer latex particles or colloidal metals, and dry-form reagents made by freezing those liquid-form reagents.

The technique used to secure the aforementioned test reagent 3 onto the inner surface of tubular container 3 is not particularly specified, including the use of pressure-sensitive adhesive tapes or adhesives.

The size of tubular container 2 is not particularly specified. The tubular container 2 may be of any suitable size, so long as it can collect blood and be subjected to centrifugation and permits the reaction of the test reagent 3 accommodated therein with the serum or plasma separated from the collected blood.

Figure 2:
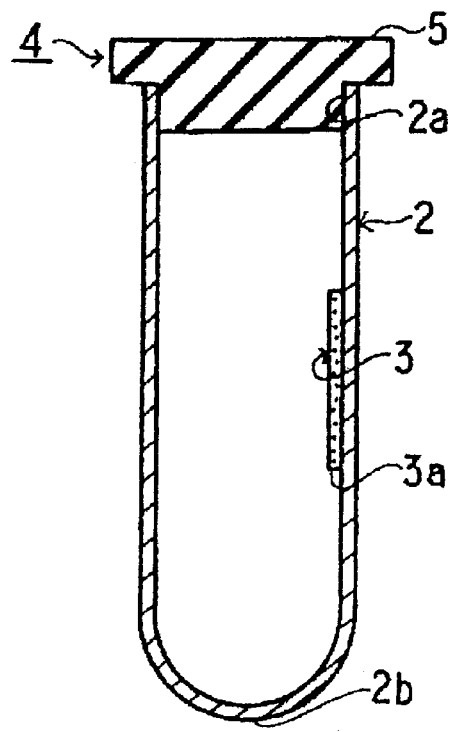
FIG. 2 is a transverse sectional view, showing one exemplary construction of the blood test container, in accordance with the present invention, wherein an interior pressured of the tubular container is reduced.

FIG. 2 is a sectional view, illustrating another exemplary construction of the blood test container in accordance with the present invention. The blood test container 4 differs in construction from the blood test container 1 shown in FIG. 1 in that the former includes a stopper 5 for closing a top opening 2a of the tubular container 2. The material used to constitute the stopper 5 is not particularly specified, and can be natural or synthetic rubber, such as silicone rubber, which exhibits rubber elasticity.

For the blood test container 4, the tubular container 2 is closed by the stopper 3 and its interior is reduced in pressure. The degree of pressure reduction is selected such that the blood can be introduced promptly into the interior of tubular container 2 when a blood-collecting needle is at one end inserted into a patient's blood vessel and at another end inserted-through the stopper 5. Generally, the interior of the tubular container 2 is reduced approximately to 0.1–0.8 atmospheric pressure.

Figure 3:
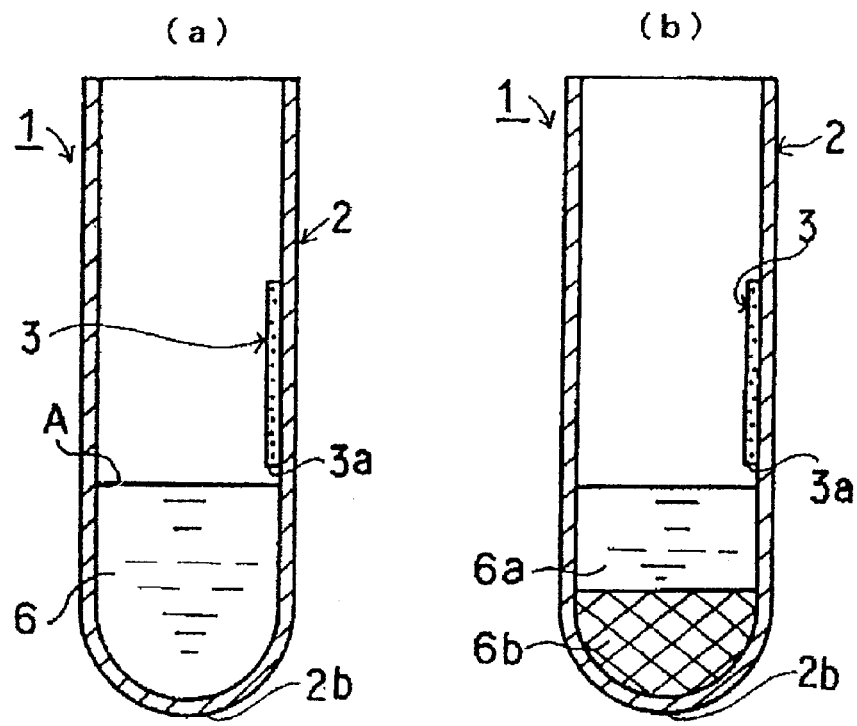
FIGS. 3(a) and 3(b) are transverse sectional views which explain blood test procedures when the blood test container shown in FIG. 1 is used, respectively.

For blood test containers 1 and 4 shown in FIG. 1 and FIG. 2, the test reagent 3 is secured onto the inner wall of tubular container 2 so that it locates a certain distance above a bottom 2b of the tubular container 2. It is thus preferred that collection of blood 6 is carried out so as for its top surface A to stay below a bottom edge 3a of the test reagent 3, as shown in FIG. 3(a) and FIG. 4(a), whereby the contact of blood 6 with the test reagent 3 is prevented. Also, as shown in FIG. 3(b) and FIG. 4(b), once centrifuged to separate the blood into serum or plasma 6a and solid matter 6b, the subsequent inclination of the tubular container 2 allows a ready contact of the test reagent 3 with the serum or plasma 6a.

That is, for the blood test containers 1, 4, the securement of the test reagent 3 at the intermediate height of the tubular container 2 leads to the provision of a contact control structure according to the present invention.

The centrifugal operation may be performed at 500–5,000 r.p.m for the approximate period of 5 minutes–30 minutes.

In the shown exemplary constructions which follow, the tubular container 2 and test reagent 3 can be made from the same materials as those described above. The stopper 5 can also be configured analogously to the stopper 5 used for the blood test container 4.

Figure 5:
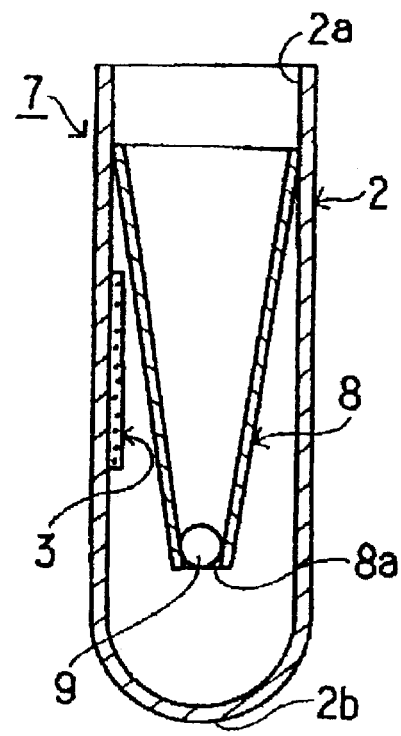
FIG. 5 is a transverse sectional view, showing one embodiment of the blood test container in accordance with the invention.

FIG. 5 is a transverse sectional view of a blood test container in accordance with the invention. For the blood test container 7, an inner container portion 8 is accommodated in the tubular container 2. The inner container portion 8 is made from the same or different material from the tubular container 2, and is secured at its upper end to an inner surface of the tubular container 2. The inner container portion 8 is configured such that its diameter is gradually reduced in dimension toward the bottom 2b of the tubular container 2 as it extends downwardly from its upper end.

The inner container portion 8 has at its bottom end a hole 8a which is closed by a solid member 9. The solid member 9 is initially secured to the inner container portion 8, as by adhesives when needed, so that it is prevented from falling downwardly and the hole 8a is kept closed as shown.

The solid member 9 is designed to fall downwardly through the hole 8a by a centrifugal force produced when the centrifuging follows the blood introduction into the inner container portion 8. The solid member 9 may be placed in position, either without or with the aid of adhesives. In the latter case, the adhesive force must be adjusted to the level that permits the solid member to fall when the centrifugal force is applied thereto. The outer diameter and material type of the solid member 9, as well as the diameter of the hole 8a, are also selected to permit the solid member 9 to fall upon centrifugation.

The solid member 9 can be made from any suitable material which allows the above-described action of the solid member 9. Useful materials include, for example, synthetic resin beads such as polystyrene beads, and polymer compounds and rubbers which have thixotropic properties, such as an oxidized ellagic acid. For the purpose of facilitating the fall of the solid member 9, the thixotropic polymer compounds or rubbers, among those materials, are preferably used to constitute the solid member 9.

In the blood test container 7, the test reagent 3 is secured onto the inner wall surface of the tubular container 2 so that it is positioned above the aforementioned solid member 9.

In the blood testing procedure using the blood test container 7, blood is introduced into the inner container portion 8 and the blood test container 7 is subsequently centrifuged. The centrifuging condition is not particularly specified. Centrifuging may be carried out at 500 r.p.m.–5,000 r.p.m. for the period of 5–+minutes, analogously to the case for the blood test container 1.

Figure 6:
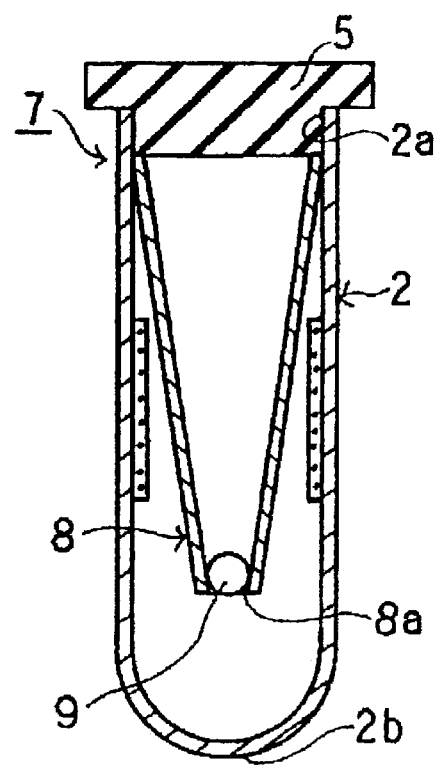
FIG. 6 is a transverse sectional view, showing one exemplary construction of the blood test container, in accordance with the invention, wherein an interior pressured of the tubular container is reduced.

During the centrifugation, the blood is held staying in the bottom portion 2b of the tubular container 2 while it is separated into serum or plasma and solid matter. This permits the test reagent 3 disposed outwardly of the inner container portion 8 to readily contact the serum or plasma. Preferably, the stopper 5 is fitted into the opening 2a of the tubular container 2, as shown in FIG. 6, and the interior pressure of the tubular container 2 is reduced. The reduction in interior pressure of the tubular container 2 allows the prompt introduction of blood into the inner container portion 8 disposed within the tubular container 8.

Figure 25:
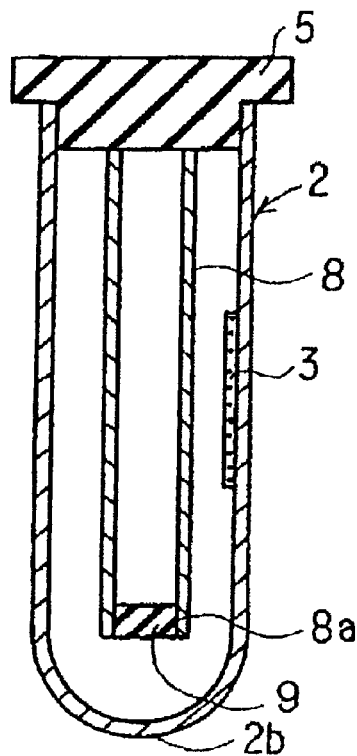
FIG. 25 is a transverse sectional view which explains a modified embodiment of the blood test container in accordance with the invention.

FIG. 25 is a transverse sectional view, showing a modified embodiment of a blood test container in accordance with the invention. In this modified embodiment, the inner container portion 8, in the form of a tube having a diameter smaller than that of the tubular container 2, is placed within the tubular container 2. That is, the inner container portion 8 is not limited to the tapered configuration shown in FIG. 5 wherein tapering is made to gradually reduce its diameter toward the bottom portion 2b, and may be in the tubular form as shown in FIG. 25. Although not depicted in FIG. 25, the inner container portion 8 is fixedly connected to the tubular container 2 by a rib which is not shown.

In the modified embodiment shown in FIG. 25, the inner container portion 8 is at its bottom opened to define a hole 8a which is closed by the rubber-made solid member 9. The solid member 9 can be made from the aforementioned materials other than rubber, whereby the blood is initially prevented from leaking from the inner container portion 8 toward outside and contacting the test reagent, as analogous to the construction embodiment shown in FIG. 5. The following centrifugation causes the solid member 9 to fall downwardly and the blood in the tubular container 2 to separate into serum or plasma and solid matter. This assures the subsequent contact of the serum or plasma with the test reagent 3.

In FIGS. 5, 6 and 25, the test reagent 3 may be secured onto an outer surface of the inner container portion 8, or onto both the outer surface of the inner container portion 8 and the inner surface of the tubular container 2. The test reagent may be placed, in the form of a liquid or powder, between the tubular container 2 and the inner container portion 8. The inner container portion 8 may be integrally connected to the separately-formed tubular container 2, or alternatively, integrally formed with the tubular container 2.

Figure 7:
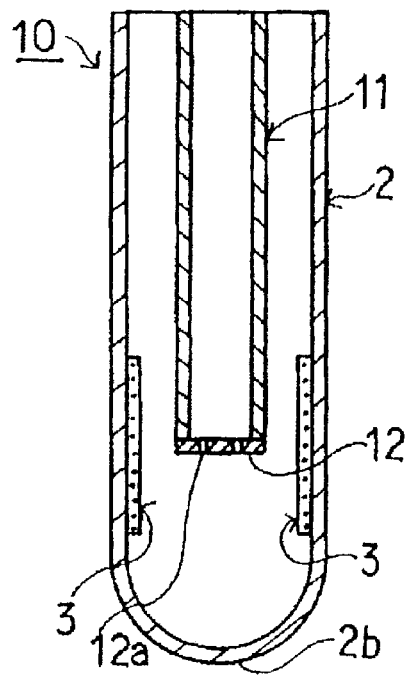
FIG. 7 is a transverse sectional view which explains the blood test container in accordance with the invention.

FIG. 7 is a transverse sectional view of a blood test container in accordance with the invention. The blood test container 10 includes the test reagents 3, 3 respectively secured onto an inner wall surface of the tubular container 2. On the inner wall surface of the tubular container 2, the test reagents 3, 3 are positioned in pairs to face toward each other. However, this is not intended to exclude the case where the reagent 3 is singularly secured onto one location on the inner wall surface.

The tubular container 2 accommodates therein a second tubular container 11 which has a reduced diameter relative to the tubular container 2. The second tubular container 11 provides a space into which blood is introduced. The second tubular container 11 can be made from various suitable materials including, for example, synthetic resins such as polyethylene terephthalate and glass. The material type is not particularly specified. Although desired to be made transparent, the second tubular container 11 needs not be made transparent since the measurement results can be obtained outside the second tubular container 11.

Figure 8:
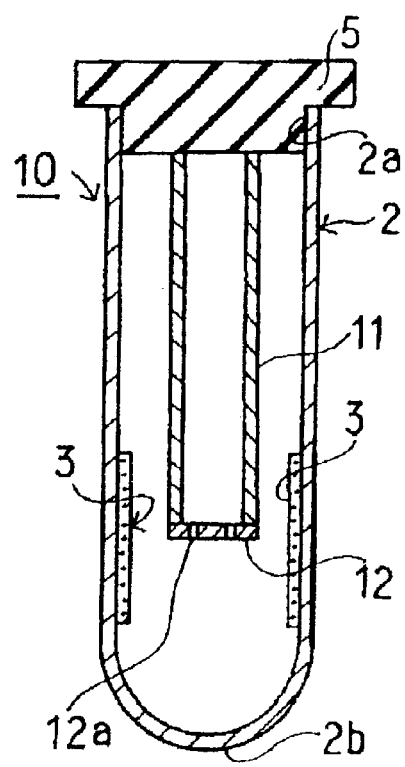
FIG. 8 is a transverse sectional view, showing one exemplary construction of the blood test container, in accordance with the invention, wherein an interior pressured of the tubular container is reduced.

The second tubular container 11 is fixedly connected to the tubular container 2 as by a rib which is not shown. In the case where the below-described stopper 5 is used, the second tubular container 11 may be secured to the stopper 5, as shown in FIG. 8.

A bottom opening of the second tubular container 11 is closed by a perforated plate 12 secured thereto. The perforated plate 12 has a number of through-holes 12a having diameters of 0.1–10 μm. The perforated plate 12 can be made from suitable synthetic resins, such as polyethylene terephthalate, or glass.

The perforated plate 12 may be adhesively secured to the second tubular container 11. The perforated plate 12 may be integrally formed with the second tubular container 11. The perforated plate 12 is not necessarily positioned to locate its bottom end contiguous with the bottom edge of the second tubular container 11, and may be positioned to locate slightly above the bottom edge.

Figure 9:
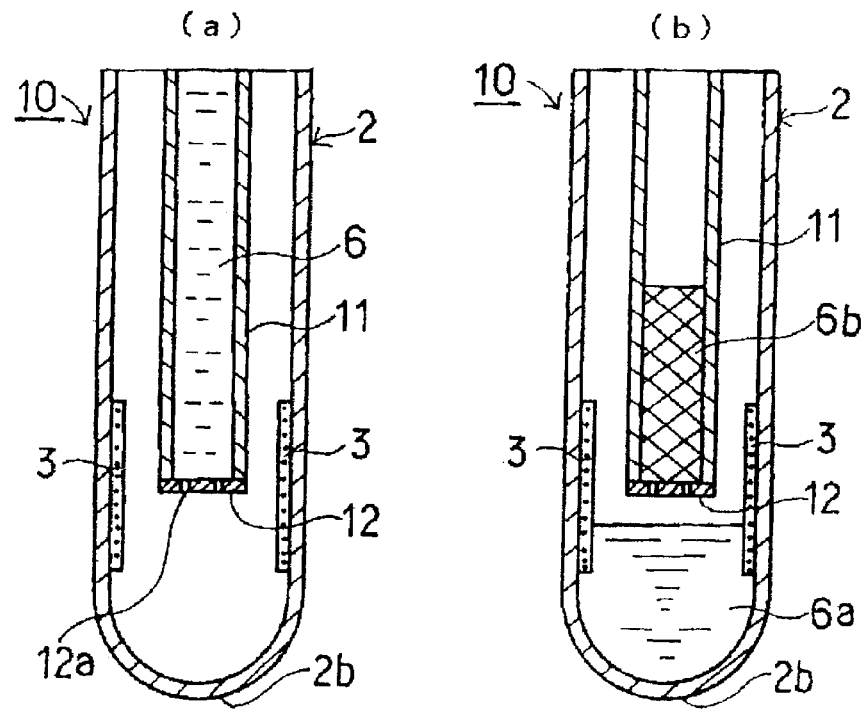
FIGS. 9(a) and 9(b) are transverse sectional views which explain blood test procedures when the blood test container shown in FIG. 7 is used, respectively.

When the blood is introduced into the second tubular container 11, the through-holes having diameters of 0.1–10 μm restrict the blood from passing therethrough and leaving the second tubular container 11. The blood is initially introduced into the second tubular container 11, as shown in FIG. 9(a). The subsequent centrifugation forces the serum or plasma 6a to pass through the perforated plate 12, while the solids 6b in the blood, such as hemocyte and clot, are held remaining in the tubular container 11, as shown in FIG. 9(b). In the situation as shown in FIG. 9(b), the test reagent 3 can be brought into contact with the serum or plasma 6a for measurement.

Figure 10:
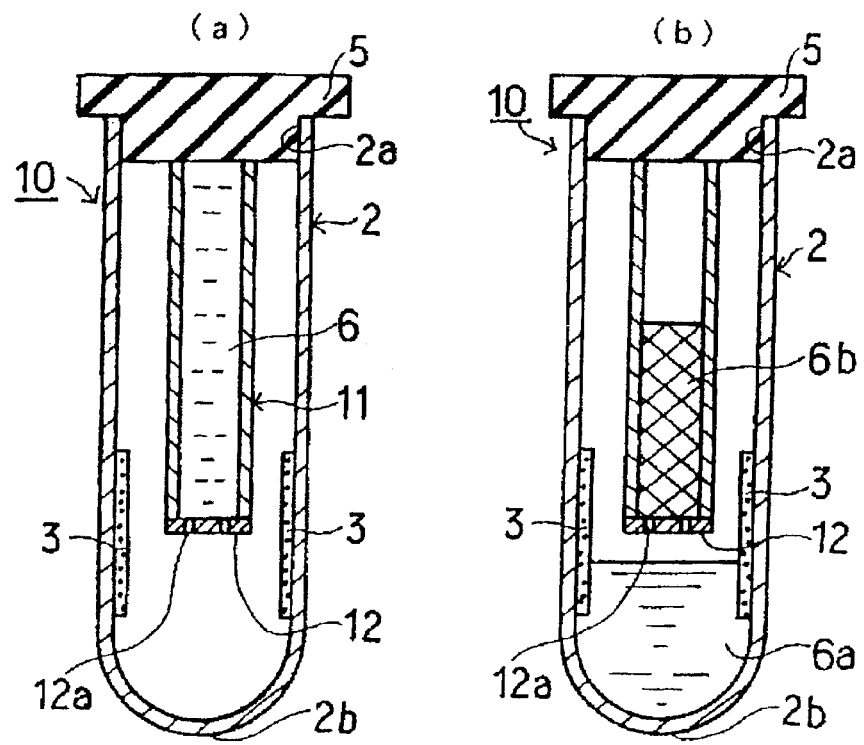
FIGS. 10(a) and 10(b) are transverse sectional views which explain blood test procedures when the blood test container shown in FIG. 8 is used, respectively.

Also for the blood test container 10, the stopper 5 is preferably diposed to close a top opening 2a of the tubular container 2, as shown in FIG. 8, and an interior of the tubular container 2 is reduced in pressure. In this case, the pressure differential can be utilized to draw the blood into the second tubular container 11 so that the blood 6 is collected in the blood test container 10, as shown in FIG. 10(a). The subsequent centrifugation forces the serum or plasma 6a to pass through the second tubular container 11, while the solid matter 6b such as clot is held remaining in the tubular container 11, as shown in FIG. 10(b). This permits the test reagent 3 to be brought into contact with the serum or plasma 6a for measurement.

The test reagent 3 may be secured onto an outer surface of the second tubular container 11, or onto both the second tubular container 11 and the tubular container 2. The test reagent may be placed, in the form of a liquid or powder, between the tubular container 2 and the second tubular container 11. The inner container portion may be integrally connected to the separately-formed tubular container, or alternatively, integrally formed with the tubular container.

Figure 11:
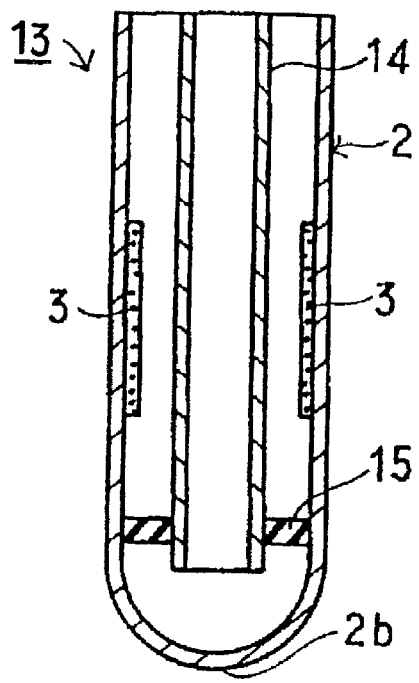
FIG. 11 is a transverse sectional view, showing one embodiment of the blood test container in accordance with the invention.

FIG. 11 is a transverse sectional view of a blood test container in accordance with the invention. For the blood test container 13, a tubular member 14 having a diameter smaller than the tubular container 2 is accommodated within the tubular container 2. The tubular member 14 is opened at its both ends and is secured to the tubular container 2 as by a rib which is not shown. This tubular member 14 can be constructed from the materials used in forming the tubular container 2, and its material type is not particularly specified.

An annular member 15 is placed near the bottom edge of the tubular member 14 to come into circumferential contacts with the outer surface of the tubular member 14 and with the inner surface of the tubular container 2. The annular member 15 can be made from materials of rubber elasticity, such as natural and synthetic rubber.

Figure 13:
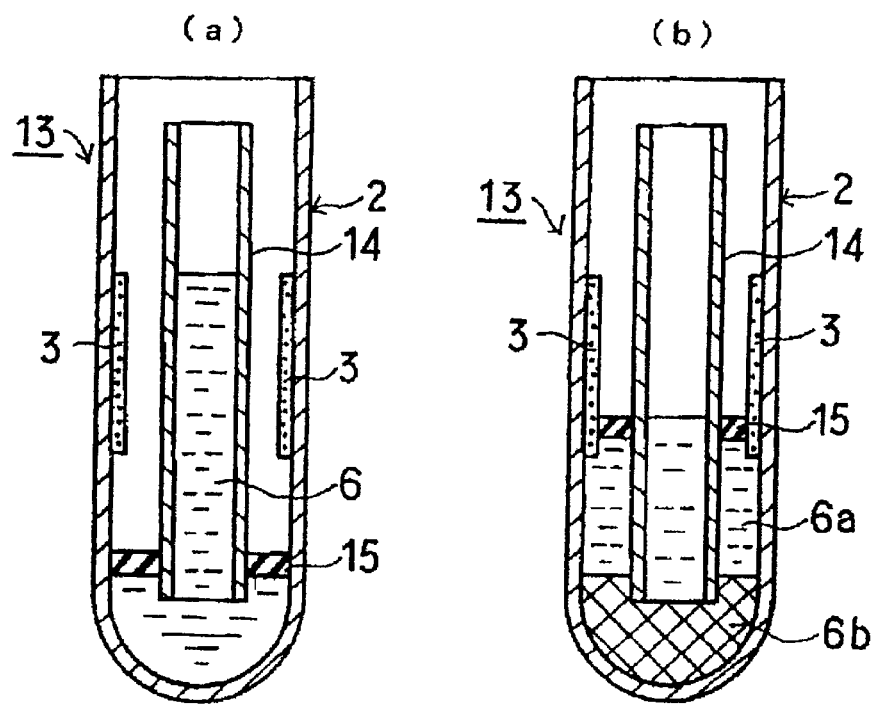
FIGS. 13(a) and 13(b) are transverse sectional views which explain blood test procedures when the blood test container shown in FIG. 11 is used, respectively.

The annular member 15 is initially located below the test reagent 3. When blood is introduced into the tubular member 14, the blood is allowed to pass through the bottom of the tubular member 14 and reaches an interior of the tubular container 2. However, the annular member 15 restricts the blood from moving upwardly thereacross, as shown in FIG. 13(a). The subsequent centrifugation forces the blood in the tubular member 14 to move downwardly, so that the annular member 15 is pushed upwardly, as shown in FIG. 13(b). Also, the centrifugation separates the blood into serum or plasma and solid matter. In this instance, the annular member 15 is caused to move upward to a position above a bottom edge of the test reagent 3, as shown in FIG. 13(b). As a result, the serum or plasma is brought into contact with the test reagent 3.

Figure 12:
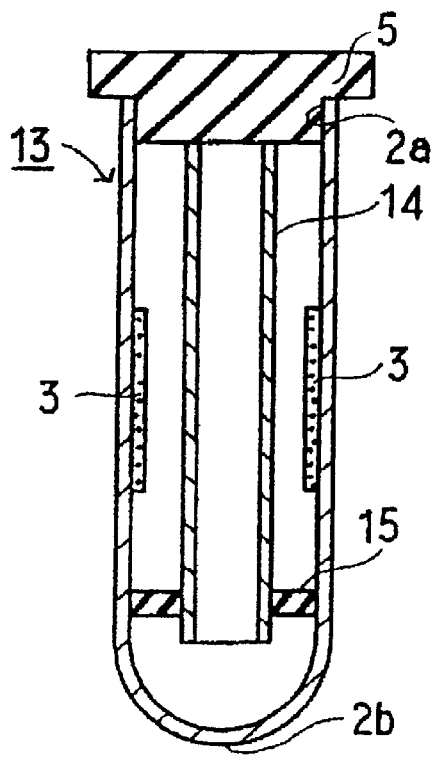
FIG. 12 is a transverse sectional view, showing one exemplary construction of the blood test container, in accordance with the invention, wherein an interior pressure of the tubular container is reduced.

For the blood test container 13, the stopper 5 may be mounted to the tubular container 2 to close its top opening 2a, as shown in FIG. 12. In such an instance, an interior of the tubular container 2 is reduced in pressure. The following insertion of a blood-collecting needle through the stopper 5 thus results in the prompt suction of blood into the tubular member 14.

Also for the blood test container 13, the test reagent 3 may be secured onto an outer surface of the tubular member 14, or onto both the tubular member 14 and the tubular container 2. The tubular member 14 may be integrally connected to the separately-formed tubular container 2, or alternatively, integrally formed with the tubular container.

Figure 15:
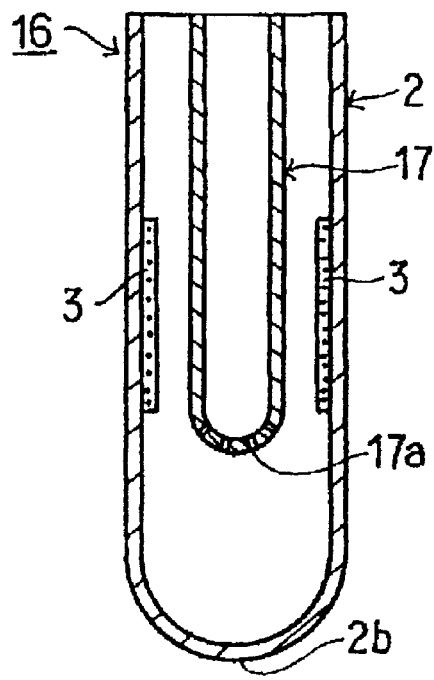
FIG. 15 is a transverse sectional view, showing one embodiment of the blood test container in accordance with the invention.

FIG. 15 is a transverse sectional view showing a blood test container embodiment in accordance with the invention. For the blood test container 16, a bottom-closed second tubular container 17 is placed within the tubular container 2. The second tubular container 17 is secured to the tubular container 2 as by a rib which is not shown. A bottom portion of the tubular container 17 is provided with a number of through-holes 17a having diameters of 10–400 μm, and this porous portion having those through-holes is positioned to locate below the test reagent 3.

The material used to form the tubular container 17 is not particularly specified. It can be formed from synthetic resins such as polypropylene and polyethylene terephthalate, glass and the like.

The porous portion having through-holes 17a may be made from a separate material. That is, a porous member having through-holes with the above-specified diameters, such as a perforated plate, may be secured to the hollow tubular member near its bottom end.

Figure 17:
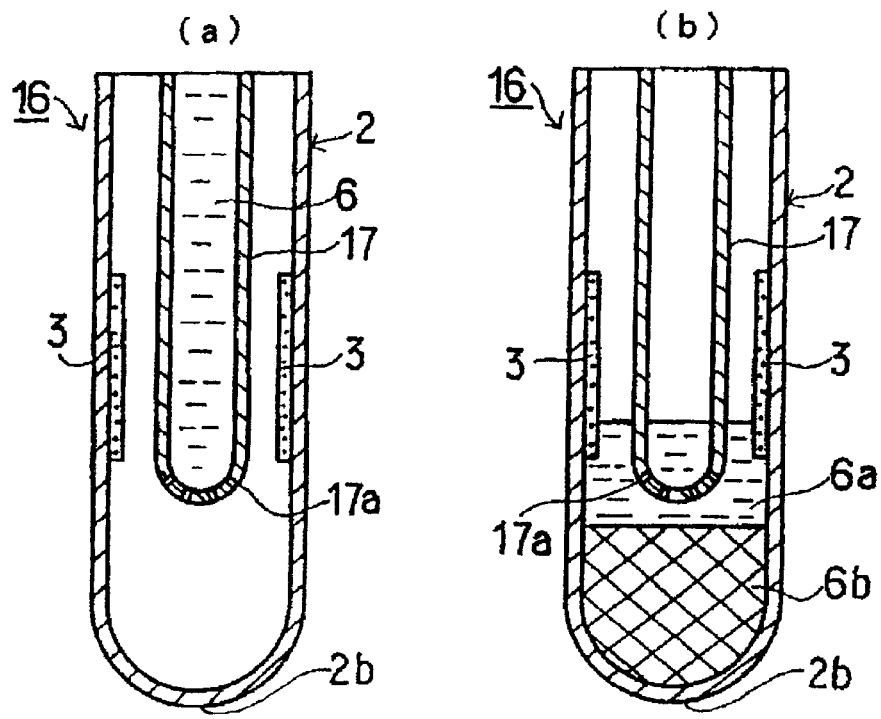
FIGS. 17(a) and 17(b) are transverse sectional views which explain blood test procedures when the blood test container shown in FIG. 15 is used, respectively.

In either case, when the blood 6 is introduced into the tubular container 17, the serum or plasma therein is allowed to gradually pass through the container but the solid matter is initially prevented from passing through the container, due to the size of the through-holes within the range of 10–400 μm, as shown in FIG. 17(a).

The centrifuging, subsequent to the introduction of the blood into the second tubular container 17, forces the blood to flow into the tubular container 2 where the blood is separated into the serum or plasma 6a and solid matter 6b see FIG. 17(b)).

Figure 16:
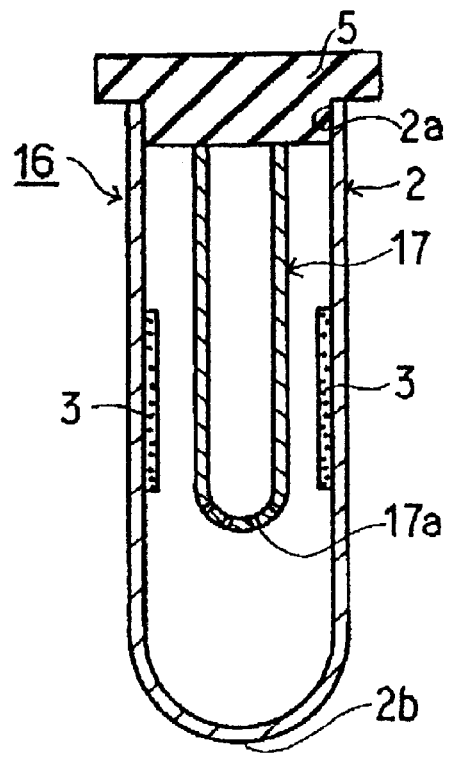
FIG. 16 is a transverse sectional view, showing one exemplary construction of the blood test container, in accordance with the invention, wherein an interior pressure of the tubular container is reduced.

Then, it becomes possible to conduct measurements by contacting the serum or plasma 6a with the test reagent 3. Also for the blood test container 16, the stopper 5 may preferably be used to close the opening 2a of the tubular container 2 with an interior of the tubular container 2 being reduced in pressure, as shown in FIG. 16. In this case, the blood can be readily introduced into the second tubular container 17 by reducing the interior pressure of the second tubular container 17, either with or without reducing the interior pressure of the tubular container 2.

The test reagent 3 may be secured onto an outer surface of the second tubular container 11, or onto both the second tubular container 11 and the tubular container 2. The test reagent may be placed, in the form of a liquid or powder, between the tubular container 2 and the second tubular container 11. The inner container portion may be integrally connected to the separately-formed tubular container, or alternatively, integrally formed with the tubular container.

Figure 19:
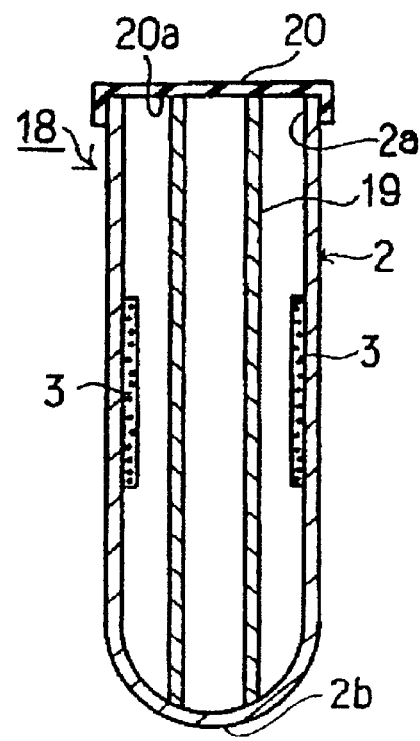
FIG. 19 is a transverse sectional view, showing one embodiment of the blood test container in accordance with the invention.

FIG. 19 is a transverse sectional view of a blood test container embodiment in accordance with the invention. For the blood test container 18, a tubular member 19 having a diameter smaller than that of the tubular container 2 is accommodated in the tubular container 2. The tubular member 19 is opened at its both ends, and its bottom end extends onto an inner bottom surface of the tubular container 2 for contact therewith. The tubular member 19 can be made from suitable glass or synthetic resins such as polypropylene and polyethylene terephthalate. However, the use of synthetic resins is preferred for their increased ability to initially prevent the blood from leaking from the tubular member 19 to enter the tubular container 2.

A cap 20 is provided as a means for pressing the bottom end of the tubular member 19 against a bottom of the tubular container 2. The cap 20 can be made from various suitable materials such as synthetic resins and glass. The cap 20 must be configured such that, when it is attached to the tubular container 2, its bottom surface 20a presses the tubular member 19 downwardly sufficiently to restrict the blood, if introduced into the tubular member 19, from leaking to the tubular container 2 side. To attain such an action, a material type of the cap 20 and a length of the tubular member 19 must be determined according to the particular dimension of the tubular container 2 used.

Figure 21:
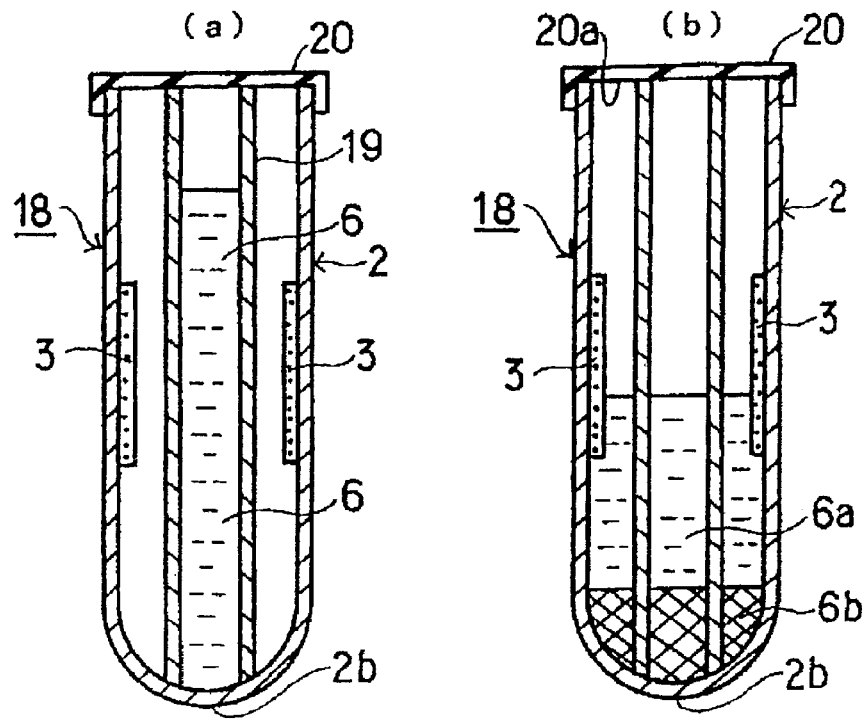
FIGS. 21(a) and 21(b) are transverse sectional views which explain blood test procedures when the blood test container shown in FIG. 19 is used, respectively.

For the blood test container 18, blood is introduced into the tubular member 19, followed by the attachement of the cap 20, as shown in FIG. 21(a). Alternatively, one end of a blood-collecting needle may be thrust into the cap 20 so that the blood can be introduced into the tubular member 19 directly from the blood-collecting needle. In an initial state, the blood is held residing in the tubular member 19 and its leakage toward the tubular container 2 side is prevented, because the bottom end of the tubular member 19 is being pressed against the bottom wall of the tubular container 2.

When the blood test container 18 is centrifuged, the blood acts to push open a space between the bottom end of the tubular member 19 and the bottom face of the tubular container 2, and escapes from the space to outside of the tubular member 19, as shown in FIG. 21(b), while it is separated into the serum or plasma 6a and solid matter 6b. The serum or plasma 6a is accordingly brought into contact with the test reagent 3 for measurements.

Figure 20:
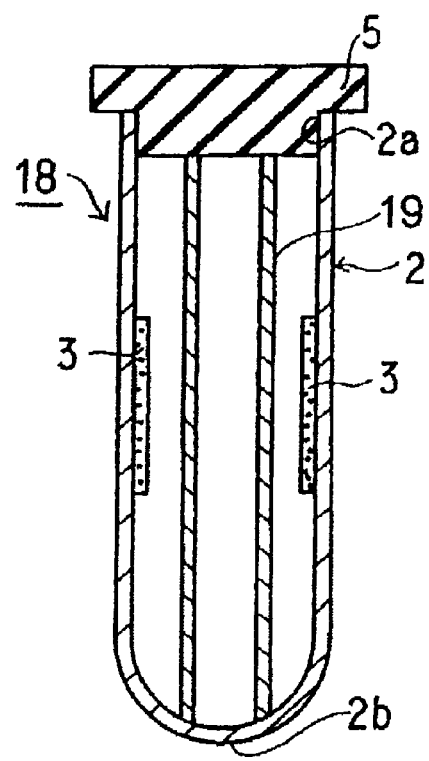
FIG. 20 is a transverse sectional view, showing one exemplary construction of the blood test container, in accordance with the invention, wherein an interior pressure of the tubular container is reduced.

For the blood test container 18, the stopper 5, instead of the cap 20 serving as a pressing means, may be attached to close the opening 2a of the tubular container 2, as shown in FIG. 20. In such a case, the configuration of the stopper 5 must be carefully selected to allow the stopper to press the tubular member 19 downwardly and acts in the same fashion as the cap 20 for the blood test container 8.

Where the stopper 5 is fitted in the tubular container 2, the blood can be drawn and introduced quickly into the tubular member 19 by reducing the internal pressures of the tubular container 2 and tubular member 19.

For the blood test container 18, the test reagent 3 may be secured onto an outer surface of the tubular member 19, or onto both the tubular member 19 and the tubular container 2. The test reagent may be placed, in the form of a liquid or powder, between the tubular member 19 and the tubular container 2. The inner container portion may be integrally connected to the separately-formed tubular container, or alternatively, integrally formed with the tubular container.

Figure 23:
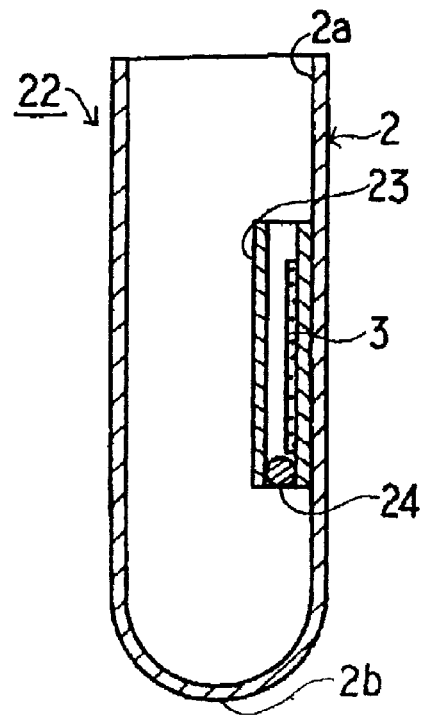
FIG. 23 is a transverse sectional view, showing one embodiment of the blood test container in accordance with the invention.

FIG. 23 is a transverse sectional view, illustrating a blood test container according to the invention. For the blood test container 22, a tubular member 23 having a diameter smaller than that of the tubular container 2 is secured onto an inner wall surface of the tubular container 2. The tubular member 23 is opened at its both ends and can be formed of suitable materials including synthetic resins such as polypropylene and polyethylene terephthalate, glass and the like. The tubular member 23 can be secured to the inner face of the tubular container 2 by the use of adhesives, pressure-sensitive adhesive tapes and the like.

The test reagent 3 is secured within the tubular member 23. Accordingly, the test reagent 3 is secured not directly but indirectly to an inner wall of the tubular container 2. A solid member 24 is inserted in the tubular member 23 for placement at the bottom opening thereof. The solid member 24 is secured, as by adhesives when needed, such that it can be held in position when no force is applied thereto, but is caused to drop when centrifuged.

The solid member 24 can be formed of the same material as used for the solid member 9 shown in FIG. 5.

When in use, blood is initially introduced into the tubular container 2 of the blood test container 22 in such a way that the entry of the blood into the tubular member 23 can be avoided. Also, the amount of the blood introduced is regulated so that a blood surface level does not reach a top end of the tubular member 23. This assures no entry of the blood into the tubular member 23, since the tubular member 23 is closed at its bottom opening by the solid member 24. The subsequent centrifuging of the blood test container 22 causes the solid member 24 to drop, as well as causing the blood to separate into serum or plasma and solid matter.

Now that the solid member 24 has fallen from inside of the tubular member 25, the subsequent inclination of the blood test container 22 allows the serum or plasma to contact the test reagent 3. However, in the case where the blood has been initially brought in level to an intermediate height of the tubular member 23, i.e., to the elevation of the test reagent 3, the serum or plasma is allowed to spontaneously flow into the tubular member 23 to contact the test reagent 3. This permits the measurement without the need to incline the blood test container 22.

Figure 24:
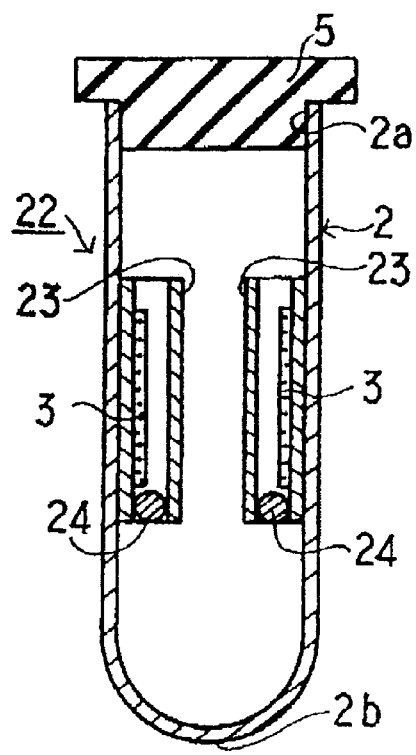
FIG. 24 is a transverse sectional view, showing one exemplary construction of the blood test container, in accordance with the invention, wherein an interior pressure of the tubular container is reduced.

Also for the blood test container 22, the stopper 5 may be used to close the opening 2a of the tubular container 2, as shown in FIG. 24, and its interior may be reduced in pressure. Such reduction in interior pressure of the tubular container 2 suction draws the blood into the tubular container 2, facilitating the blood collection thereinto. In FIG. 24, a pair of the tubular members 23 is disposed to face toward each other. The inner container portion may be integrally connected to the separately-formed tubular container, or alternatively, integrally formed with the tubular container.

Figure 26:
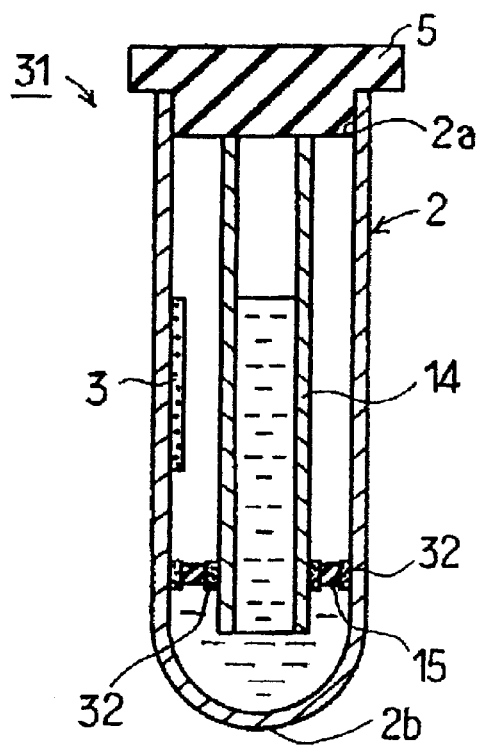
FIG. 26 is a transverse sectional view of the blood test container in accordance with the invention.

FIG. 26 is a transverse sectional view, illustrating a blood test container in accordance with the invention. The blood test container 31 is constructed in the same configuration as the blood test container 13 shown in FIG. 11, according to the present invention, with the exception that the annular member 15 is mounted in a different fashion. Accordingly, the description of the like parts is omitted by referring to the description given above in explaining the embodiment shown in FIG. 11.

For the blood test container 31, the annular member 15 is fixedly placed between the outer surface of tubular member 14 and the inner surface of tubular container 2 with the aid of paraffin 32. In this case, the compositions of the formula $C_nH_{2n+2}$ (n is 18–22, preferably 22–24) are used for the paraffin 32. Examples of such paraffins include octadecane ($C_{18}H_{38}$, melting point of 28° C.), nonadecane ($C_{19}H_{40}$, melting point of 32° C.), icosane ($C_{20}H_{42}$, melting point of 37° C.), monoicosane ($C_{21}H_{44}$, melting point of 42° C.), diicosane ($C_{22}H_{46}$, melting point of 47° C.), triicosane ($C_{23}H_{48}$, melting point of 52° C.), tetraicosane ($C_{24}H_{50}$, melting point of 57° C.), and pentaicosane ($C_{25}H_{52}$, melting point of 62° C.).

These paraffins are caused to melt when heated to temperatures of not below their respective melting points as indicated above. For the blood test container 31, the annular member 15 is initially secured to both the tubular member 14 and tubular container 2 by the paraffin 32, as shown in FIG. 26. When blood is introduced into the tubular member 14, the annular member 15 withstands the flow of blood so that the annular member 15 is not forced to move upwardly, as analogously to the instance for the blood test container 13 shown in FIG. 11.

Figure 27:
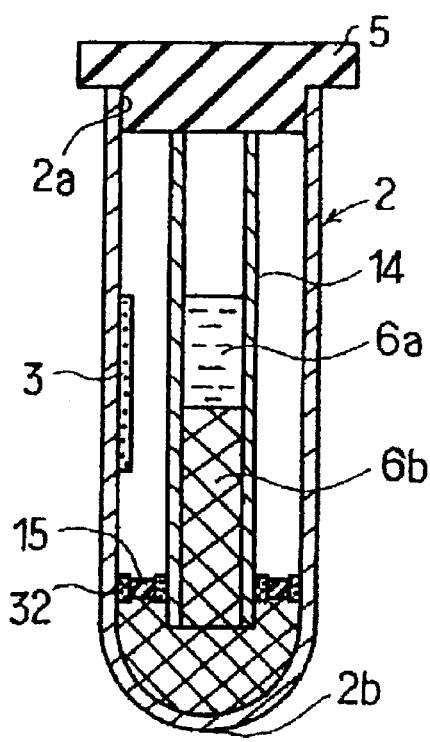
FIG. 27 is a transverse sectional view, showing the condition when the blood test container shown in FIG. 26, after blood collection, was centrifuged.
Figure 28:
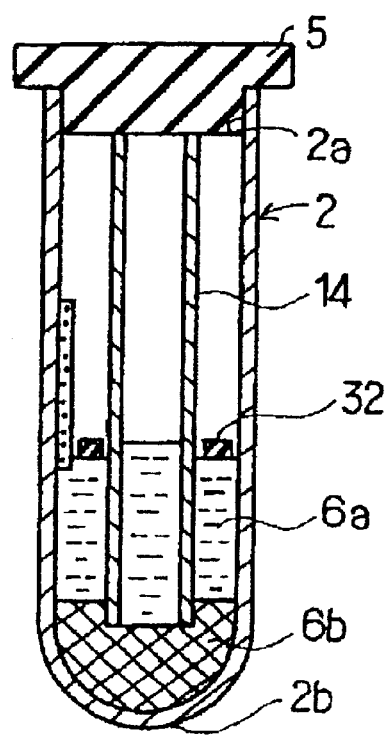
FIG. 28 is a transverse sectional view, showing the condition when the blood test container shown in FIG. 26, after the centrifugation, was heated.

The following centrifugation separates the blood into the serum or plasma 6a and the solid matter 6b, as shown in FIG. 27. The aforementioned paraffin 32 is caused to melt when subsequently heated to a temperature of not below its melting point, permitting the annular member 15 to freely move vertically, as shown in FIG. 28. This allows the serum or plasma 6a to push the annular member 15 upward and contact the test reagent 3. Also, the inner container portion may be integrally connected to the separately-formed tubular container, or alternatively, integrally formed with the tubular container.

Figure 29:
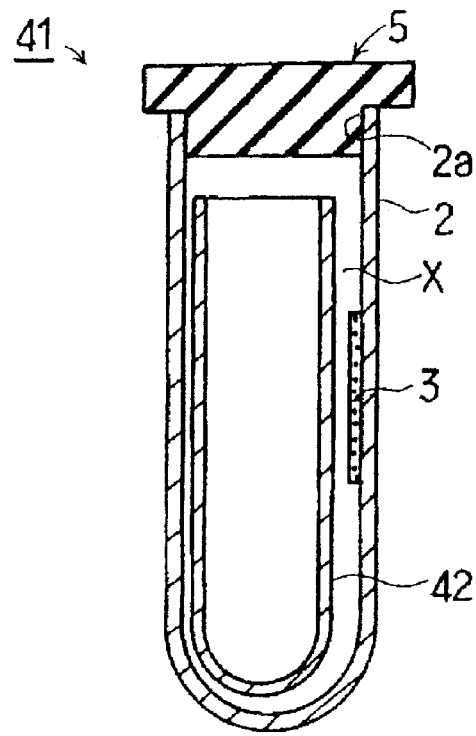
FIG. 29 is a transverse sectional view, showing the blood test container in accordance with the invention.

FIG. 29 is a transverse sectional view, showing a blood test container embodiment in accordance with the invention. For the blood test container 41, a closed-bottom second tubular container 42 is accommodated within the tubular container 2. The tubular container 42 can be made from suitable glass or synthetic resins such as polyethylene terephthalate.

The blood test reagent 3 is secured onto an inner surface of the tubular container 2. The stopper 5 is fittingly pressed into the opening 2a of the tubular container 2 to seal its interior.

The tubular container 2, blood test reagent 3 and stopper 5 are constructed analogously to those of the above-described test container 1 in accordance with the invention shown in FIGS. 1 and 2.

The second tubular container 42 having a diameter smaller than the tubular container 2 is accommodated in the tubular container 2.

When in use, the interior pressure of the tubular container 2 is reduced, a vacuum blood-collecting needle is inserted through the stopper 5, and blood is introduced into the tubular container 42 by using a vacuum blood collection technique. An alternative sequence may be detaching the stopper 5, introducing the blood into the second tubular container 42, and again attaching the stopper 5.

The blood test container is subsequently centrifuged. Centrifuging may be achieved at 500–5,000 r.p.m. for about 5 minutes–30 minutes. This results in the separation of the blood into serum or plasma and solid matter. When the blood test container 41 is subsequently turned upside down, the serum or plasma previously held in the second tubular container 42 is now permitted to flow into a space X defined between the outer surface of second tubular container 42 and the inner surface of tubular container 2 and finally contact the blood test reagent 3 to react therewith.

This permits the visual observation of the reaction result from outside of the tubular container 2, or permits measurement of the reaction result by the use of a measuring equipment such as a spectro photometer.

Preferably, the blood test container 41 is closed tight by using the stopper 5 so that the blood can be introduced promptly into the second tubular container 42 upon reduction of an interior pressure of the tubular container 2. The degree of pressure reduction is generally in the approximate range of 0.1–0.8 atmospheric pressure. The inner container portion may be integrally connected to the separately-formed tubular container, or alternatively, integrally formed with the tubular container.

The test reagent 3 may be secured onto an outer surface of the second tubular container 42, or onto both the second tubular container 42 and the tubular container 2. The test reagent may be placed, in the form of a liquid or powder, between the tubular container 2 and the second tubular container 42.

Figure 30:
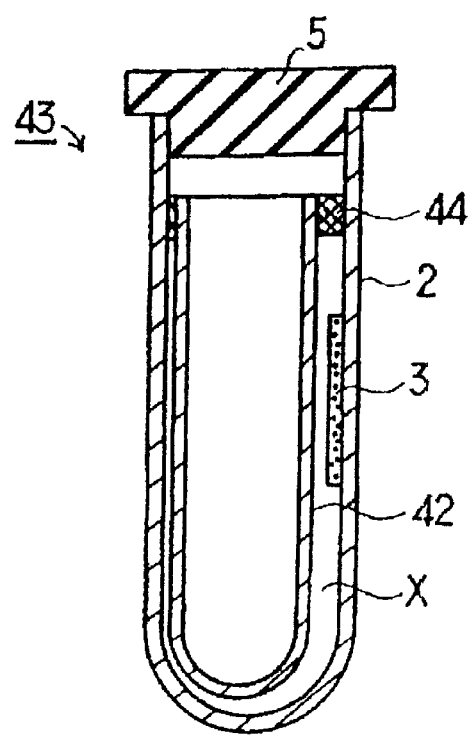
FIG. 30 is a transverse sectional view which explains the blood test container in accordance with the invention.

FIG. 30 is a transverse sectional view, illustrating a blood test container in accordance with the invention.

For the blood test container 43, a space X defined between the second tubular container 42 and the tubular container 2 is sealed by a sealing member 44. That is, the space X containing the test reagent 3 is sealed by the sealing member 44.

The sealing member 44 is secured to locate above the blood test reagent 3, e.g., extend laterally from near a peripheral top end of the second tubular container 42 to an inner surface of the tubular container 2, as shown in FIG. 30.

The sealing member 44 is formed from water-soluble material. The water-soluble material is not particularly specified, so long as it can isolate the blood introduced in the tubular container 42 from the test reagent 3. Examples of such water-soluble materials include, but not limited to, various natural polymers, semisynthetic materials and synthetic polymers. Examples of natural polymers include chitin, chitosan, casein, gelatin, collagen, egg albumin, starch (wafer), seaweeds, carrageenan, sodium alginate, agar, xanthane gum and pullulan. Examples of semisynthetic materials include dextrin, methyl cullulose and carboxy methyl cellulose. Examples of synthetic polymers include poyvinyl alcohol, sodium polyacrylate, polymethacrylic acid, polyacrylamide, polyethylene oxide, polyetylene glycol and the like.

Exemplary commercial products for use as the water-soluble material include SOLBLON (manufactured by Icello Chemical Co., Ltd.), KURAREAR (manufactured by Kuraray Co., Ltd.), TOSLON (manufactured by Tokyo Cellophane Co., Ltd.), HI-CELLON (Nippon Synthetic Film Co., Ltd.), VINYLON Film (manufactured by Kuraray Co., Ltd.), BOBLON (manufactured by Nippon Synthetic Film Co., Ltd.), EMBLER (manufactured by Unitica Co., Ltd.), EXCEED (manufactured by Okura Kogyo Co., Ltd.), EVAL (manufactured by Kuraray Co., Ltd.) and the like.

When in use, the blood is introduced into the second tubular container 42, followed by centrifugation. The centrifugation can be achieved under the same conditions as employed for the blood test container 41.

The blood, when centrifuged, is separated into serum or plasma and solid matter. When the blood test container 43 is subsequently turned upside down, the serum or plasma is brought into contact with the water-soluble material 44 which is then caused to dissolve. This allows the serum or plasma to flow into the space X where it contacts the test reagent 3 and the reaction thereof proceeds.

The reaction result can be observed visually from outside, or alternatively, measured by a measuring equipment such as a spectro photometer.

While the blood test container in accordance with the invention uses water-soluble material for the sealing member 44, the blood test container in accordance with the invention uses material having a melting point of not below 40° C. for the sealing member 44. The material having a melting point of not below 40° C. is not particularly specified, and may be paraffin of the formula $C_nH_{2n+2}$(n is 18–22), for example.

Where the aforementioned material having a melting point of not below 40° C. is used for the sealing member 44, the blood test container 43, after being centrifuged, may be turned upside down and heated so that the sealing member 44 is elevated in temperature to 40° C. or higher. The sealing member 44 is then caused to melt, resulting in the entry of the serum or plasma into the space X where it contacts the test reagent 3 for reaction therewith. The inner container portion may be integrally connected to the separately-formed tubular container, or alternatively, integrally formed with the tubular container.

For the blood test container 43, the water-soluble material is used to form the sealing member 44. The blood test container in accordance with the invention, however, uses thixotropic material having a viscosity of 5,000–500,000 centipoise to form the sealing member 44. The other parts are identical in structure to the blood test container 43.

The sealing member may be made from oxidized ellagic acid or chlorinated polybutene, for example.

In such an instance, when the blood is introduced into the second tubular container 42, the immediate entry of the blood into the space X is reliably prevented by the presence of the sealing member having a thixotropic property and a viscosity within the above-specified range. During the centrifugal operation to separate the blood into serum or plasma and solid matter, the sealing member 44 is forced to move toward a bottom of the tubular container 2. As a result, sealing of the space X is deactivated. Accordingly, when the blood test container 43, after being centrifuged, is turned upside down, the serum or plasma is brought into the space X where it contacts the test reagent 3 for reaction therewith. The inner container portion may be integrally connected to the separately-formed tubular container, or alternatively, integrally formed with the tubular container.

FIGS. 31 through 34 are views which explain an exemplary construction of a blood test container according to the invention.

The blood test container 45 has the tubular container 2 and the second tubular container 42. The test reagent 3 is secured onto an outer surface of the second tubular container 42.

The blood test container 45 uses a stopper 46 which, when pressed, can be fitted in both the tubular container 2 and the second tubular container 42. The stopper 46 has a first stopper portion 46a which extends upwardly from a distal end of the stopper and has such a relatively small diameter that it, when pressed, fits in the second tubular container 42. The continuous and upward extension from the first stopper portion 46a is a second stopper portion 46b which has such a relatively large diameter that it, when pressed, fits in the tubular container 2.

Figure 32:
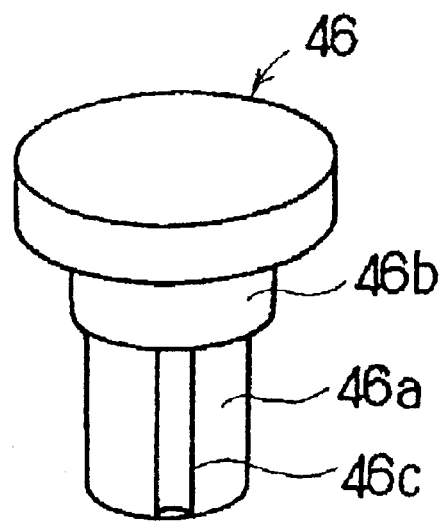
FIG. 32 is an exploded perspective view of the blood test container shown in FIG. 31.
Figure 32:
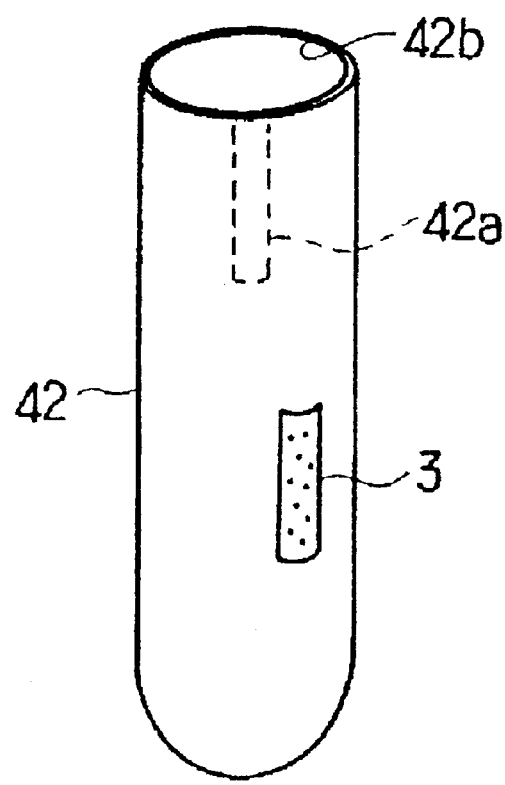
Figure 33:
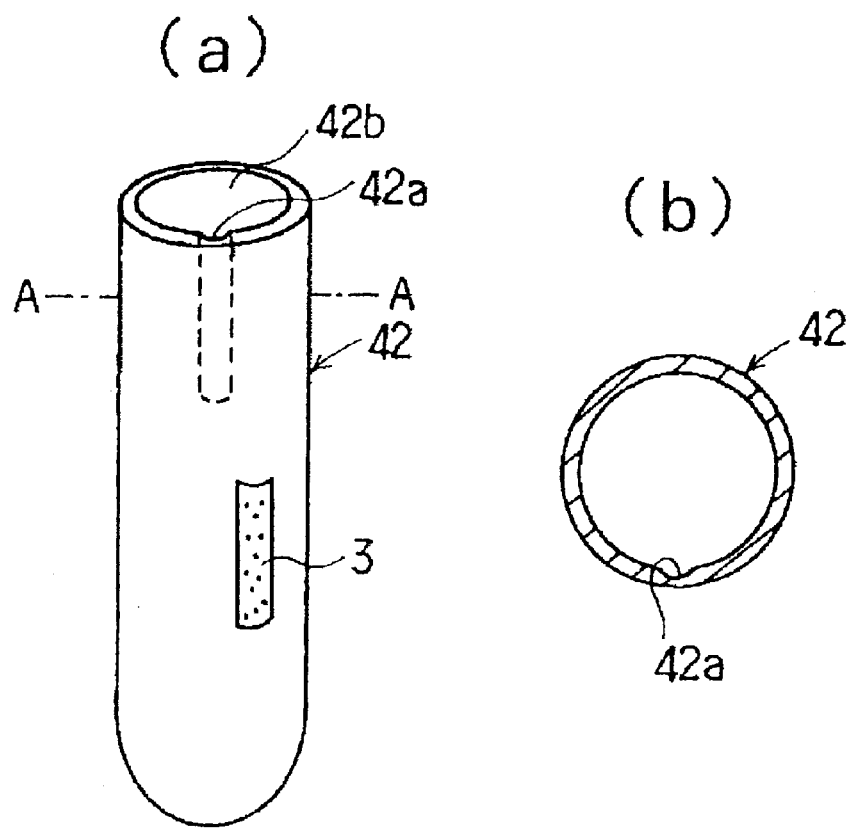
FIGS. 33(a) and 33(b) are a perspective view of the second tubular container for use in the blood test container shown in FIG. 31 and a sectional view taken along the line A—A of FIG. 33(a), respectively.
Figure 34:
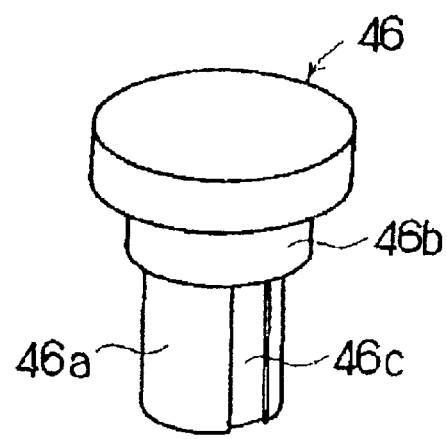
FIG. 34 is a perspective view of the stopper for use in the blood test container shown in FIG. 31.

The first stopper portion 46a has a groove 46c on its outer periphery, which extends in a length direction, as shown in FIGS. 32 and 34.

The second tubular container 42 has on its inner surface a groove 42a which extends downwardly from the opening edge 42b along a length direction, as shown in FIGS. 33(a) and 33(b).

The aforementioned grooves 46c and 42a extend upwardly and downwardly, respectively, from a region where the first stopper portion 46a is press fitted in the second tubular container 42.

When the blood test container 45 is used, blood is introduced into the second tubular container 42. In this case, the stopper 46 may be detached from the second tubular container 42 before the blood is introduced into the second tubular container 42. Alternatively, the stopper 46 may be held attached to the second tubular container 42 and the blood is introduced into the second tubular container 42 as by using a vacuum blood-collecting needle.

Subsequently, the stopper 46 is rotated to laterally align the groove 46c thereon with the groove 42a on the second tubular container 42. As a result, the grooves 42a and 46c provide a flow path which communicates the interior of the second tubular container 42 with the space X between the outer face of the second tubular container and the inner face of the tubular container.

The following centrifugation separates the blood into serum or plasma and solid matter. When the blood test container 45 is then turned upside down, the serum or plasma is caused to pass through the flow path into the space X where it contacts the test reagent 3 for reaction therewith.

Also in the this exemplary constructions, an interior pressure of the blood test container 45 may preferably be reduced. The subsequent insertion of a blood-collecting needle or the like through the stopper 46 results in the introduction of the blood sample into the second tubular container 42 by a suction force created by the pressure reduction. Also, the inner container portion may be integrally connected to the separately-formed tubular container, or alternatively, integrally formed with the tubular container.

Figure 35:
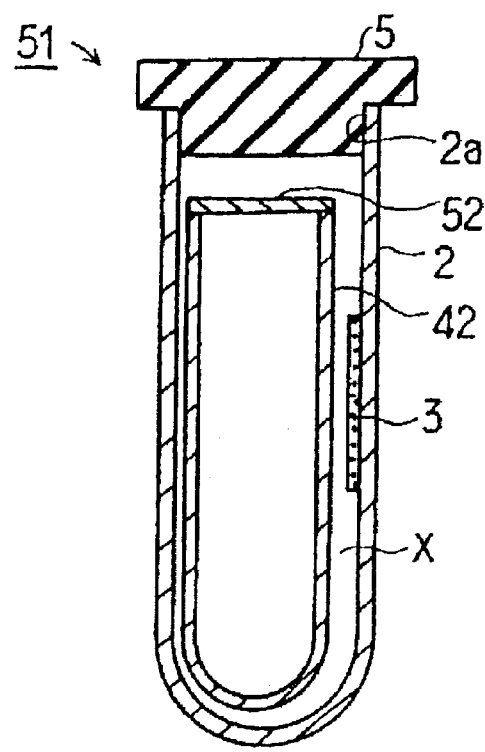
FIG. 35 is a transverse sectional view which explains the blood test container in accordance with the invention.

FIG. 35 is a transverse sectional view which explains a blood test container in accordance with the invention. For the blood test container 51, a second tubular container 42 having a diameter smaller than that of the tubular container 2 is accommodated within the tubular container 2. The test reagent 3 is secured onto an inner surface of the tubular container 2. Also, the stopper 5 is press fitted into the opening 2a of the tubular container 2. These follow the construction of the blood test container 41 shown in FIG. 29.

A feature of the blood test container 51 resides in its provision of a polymer film 52 having a thickness of up to 100 μm which serves to seal a top opening of the second tubular container 42.

The aforementioned polymer film 52 is not particularly specified, and may be formed of polyethylene, polyvinyl chloride or arabic gum, for example. A metal film having a thickness of up to 100 μm, such as of aluminum, silver or copper, can also be used in the place of the polymer film 52.

Where the polymer film 52 is used, it may be secured to an open edge of the tubular container 42 either by heat bonding or by using a suitable adhesive. Where the metal film is used, it may be secured to an open edge of the tubular container 42 by using a suitable adhesive.

For the illustrated blood test container 51, the polymer film is broken through as by a needle before a blood sample is introduced into the second tubular container 42. The small thickness of the polymer film 52 or metal, up to 100 μm, permits a needle or the like to easily break through a part of thereof. Accordingly, in an exemplary case where a vacuum blood-collecting needle is subsequently inserted through the attached stopper 5, a catheter or a blood-discharging tip of the vacuum blood-collecting needle can be easily inserted through the broken part of the polymer film 52. Alternatively, the blood-discharging tip of the vacuum blood-collecting needle may be utilized to directly break through the polymer film 52. Since the opening of the second tubular container 42 is sealed by the polymer film 52, the blood, when introduced into the second tubular container 42, is prevented from flowing into the space X defined between the outer face of second tubular container 42 and the inner face of tubular container 2.

In the testing, a blood sample is brought into the second tubular container 42 and subsequently centrifuged so that it is separated into serum or plasma and solid matter. The blood test container 51 is then turned upside down to allow the serum or plasma to pass through the broken part of the polymer film 52 and flow into the space X where it contacts the test reagent 3.

Also in the case of using the metal film in the place of the polymer film 52, the above procedure may be followed to contact the serum or plasma with the test reagent 3.

Preferably, the blood test container 51 is sealed by the stopper 5 and its interior pressure is reduced to create a suction force which acts to draw the blood promptly into the second tubular container 42.

Figure 36:
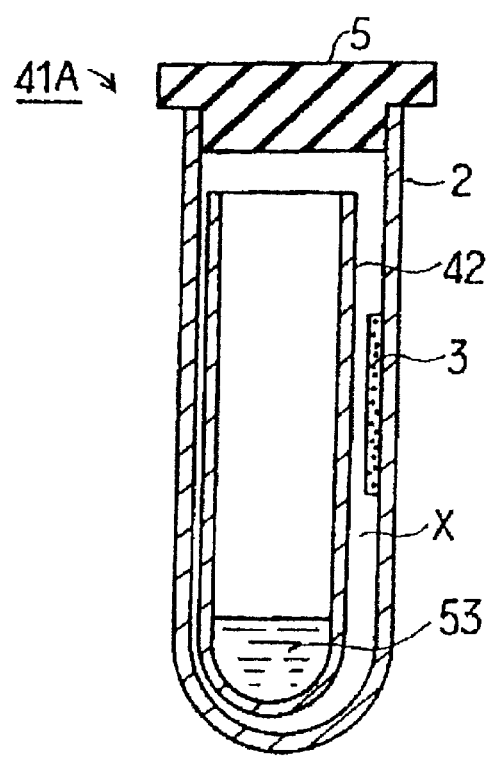
FIG. 36 is a transverse sectional view, showing the blood test container in accordance with the invention wherein the serum or plasma separating medium is accommodated in the second tubular container.

FIG. 36 is a sectional view which explains a modified embodiment of the blood test container 41. For the modified blood test container 41A, a serum separating medium 53 is accommodated in the second tubular container 42. The serum separating medium 53 is not particularly specified, and can be illustrated by polybutene, polystyrene, oxidized ellagic acid or the like which has a specific gravity within the range of 1.00–1.2. These substances can also be used as a plasma separating medium, and in such a case, the serum separating medium may be utilized as an alternative of the plasma separating medium 53.

For the blood test container 41A, the serum separating medium 53 is accommodated in the second tubular container 42. This assures that the blood, when centrifuged, separates into the serum and clot. Similarly, the use of the plasma separating medium always results in separation of the blood into the plasma and solid matter.

Also for the blood test containers 43, 45, 51 according to the other exemplary constructions as described earlier, the serum or plasma separating medium may be accommodated in the second tubular container 42, whereby the blood, when centrifuged, can be reliably separated into the serum or plasma and the solid matter.

For the blood test containers 41, 41A, 43 and 51, securement of the second tubular container 42 to the tubular container 2 can be achieved by the sealing member 44, if one is used. Unless the sealing member 44 is used, a bridge-like connection member such as of a synthetic resin or metal may be provided which extends between an outer wall surface of the second tubular container 42 and an inner wall surface of the tubular container 2 for connection thereof. Alternatively, an open top end of the second tubular container 42 may be connected to the stopper 5. Also, the inner container portion may be integrally connected to the separately-formed tubular container, or alternatively, integrally formed with the tubular container.

Further, the tubular container 2 may be tapered to have a decreasing diameter toward its bottom. In such a case, the second tubular container 42, when its bottom portion is brought into abutment against an inner face of the tapered portion of the tubular container 2, can be held in position within the tubular container 2. Alternatively, the tubular container 2 may be configured to carry on its inner face at least one projection by which the second tubular container 42 can be held in a predetermined position while the space X is defined between the second tubular container 42 and the inner face of the tubular container 2.

The test reagent 3 may be secured to an inner face of the tubular container 2 and/or an outer face of the second tubular container 42. The test reagent 3 may be placed, in the form of a liquid or powder, between the tubular container 2 and the second tubular container 42.

FIGS. 37(a) and (b) are transverse sectional views which explain a blood test container in accordance with the invention.

For a blood test container 61, a second tubular container 62 is accommodated within the tubular container 2. The second tubular container 62 has a smaller diameter than the tubular container 2 and is at its top end secured to the stopper 5.

The second tubular container 62 has at its bottom end a trap portion 62a which is configured to project downwardly and serves to trap erythrocytes. Provided adjacent the trap portion 62a is a hemocyte separator portion 62c which has a number of through-holes 62b having diameters of 0.1–20 μm.

Any suitable material can be used for the second tubular container 62, so long as the bottom-located trap portion 62a made therefrom functions to trap etythrocytes. Examples of useful materials include polymeric materials, such as polyethylene terephthalate, vinyl chloride, polyethylene, polystyrene and polypropylene, and inorganic materials or metals such as glass, iron and aluminum.

The size of the trap portion 62a may be determined depending on the particular volume of blood collected. The trap portion 62a may generally be sized in volume to about 50% of a total volume of the blood collected, since a standard hematocrit value for human blood is around 50%.

A number of through-holes 62b which permit serum or plasma to pass therethrough are provided adjacent the trap portion 62a, thereby constituting the hemocyte separator portion 62c. The hemocyte separator portion 62c having such through-holes 62b can be constructed from suitable filter materials, or alternatively, from particles aggregated so as to form the through-holes 62b. When the blood is collected in the second tubular container 62 and then centrifuged, the separated serum or plasma is allowed to pass through the through-holes 62b to leave the tubular container 62, while the controlled size of the through-holes within the range of 0.1–20 μm prevents the passage of the erythrocyte which, because of its high specific gravity, is retained within the trap portion 62a. As a result, the serum or plasma passes through the through-holes 62b and reaches a bottom portion of the tubular container 2 where it is collected and stored.

The serum or plasma collected in the bottom portion of the tubular container 2, when it amounts to a certain volume, is contacted with the test reagent 3 and a reaction thereof is initiated.

In the testing, blood is introduced into the second tubular container 62 and subsequently centrifuged. This results in allowing the separated serum or plasma to collect in the bottom portion of the tubular container 2. When the volume of the serum or plasma collected increases and its level reaches the test reagent 3, a reaction therebetween is initiated immediately.

As shown in FIG. 37(b), in the case where the serum or plasma separated by centrifugation is insufficient in volume to reach the test reagent 3, the reaction of the serum or plasma 63 with the test reagent 3 can be caused to start by slanting or turning the blood test container 61 upside down.

Also in this exemplary construction, an inner pressure of the blood test container 61 may preferably be reduced to the aforestated level to create a suction force which acts to draw a blood sample promptly into the second tubular container 62.

Also, the test reagent 3 may be secured to either an outer face of the second tubular container 62 or to both of the outer face of the second tubular container 62 and the inner face of the tubular container 2. The inner container portion may be integrally connected to the separately-formed tubular container, or alternatively, integrally formed with the tubular container.

Figure 38:
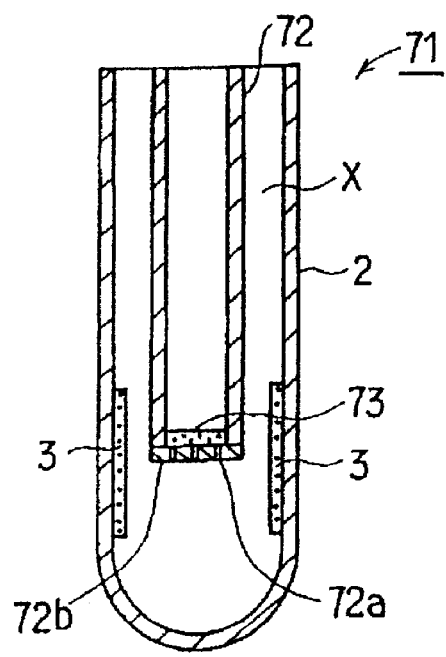
FIG. 38 is a transverse sectional view which explains the blood test container in accordance with the invention.
Figure 39:
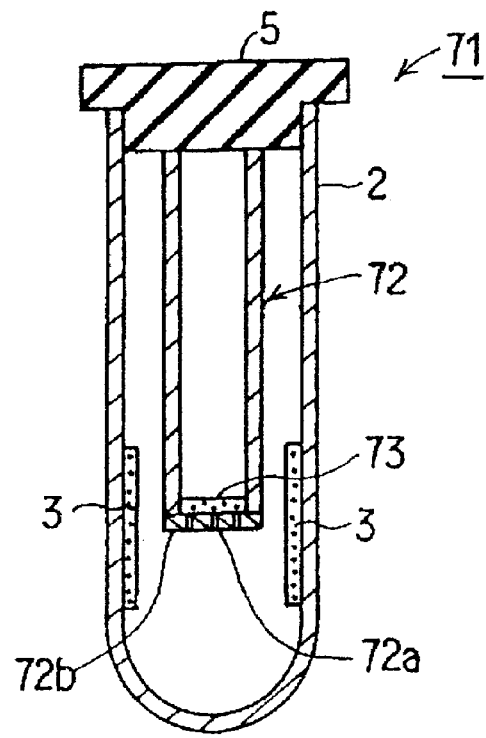
FIG. 39 is a transverse sectional view which explains a modified embodiment of the blood test container shown in FIG. 38.

FIGS. 38 and 39 are sectional views which explain a blood test container in accordance with the invention.

For a blood test container 71, a second tubular container 72 having a diameter smaller than that of the tubular container 2 is accommodated in the tubular container 2. Although the second tubular container 72 is depicted in FIG. 38 as if floating within the tubular container 2, the second tubular container 72 can be fixedly placed within the tubular container 2 as by using the above-described suitable structure which connects the second tubular container 42 and the tubular container 2 while assuring the space X between the outer face of the second tubular container 72 and the inner face of the tubular container 2.

For a blood test container 71, a second tubular container 72 has a bottom provided with plural through-holes 72a. Preferably, these through-holes 72a are sized in diameter to permit passage of serum or plasma but prevent passage of hemocytes therethrough, i.e., not to exceed 10 μm. A layer 73 is provided to overlie the bottom provided with through-holes 72a, which is comprised of hydrophilic fine particles having diameters of 0.1–200 μm.

In an exemplary construction shown in FIG. 38, a separate bottom member 72b having the aforementioned plural through-holes 72a is secured by adhesive (not shown) to close a bottom opening of a tubular member 72c. However, those through-holes 72a may be provided in a bottom of a closed-bottom tubular container.

The 0.1–200 μm diameter hydrophilic fine particles used to form the aforementioned layer is not particularly specified in type, and may be comprised, for example, of hydrophilic group-containing, e.g., carboxyl-containing polystyrene, vinyl chloride, silica, iron oxide or sugar.

When in use, blood is introduced into the second tubular container 72. The blood, when subsequently centrifuged, is caused to separate into serum or plasma and solid matter. In such an instance, red and white blood cells and the like are held staying in or above the hydrophilic fine particle layer 73 while the serum or plasma is allowed to flow downwardly and pass through the through-holes 72a to leave the second tubular container 72. When the serum or plasma is brought into contact with the test reagent 3, a reaction thereof is caused to take place.

In the case where the serum or plasma collected is insufficient in volume to reach the test reagent 3, the contact of the serum or plasma with the test reagent 3 can be attained by inclining or turning the blood test container 71 upside down.

Preferably, the stopper 5 is pressed to fit in the tubular container 2, as shown in FIG. 39, and an interior of the blood test container 71 is brought into a pressure-reduced condition. Such reduction in internal pressure of the blood test container 71 allows prompt introduction of a sample blood into the second tubular container 72 when a vacuum blood-collecting technique is utilized, and also creates a suction force which acts to draw the blood through the hydrophilic fine particle layer 73 where it is filtered effectively, so that the serum or plasma can be brought into a bottom portion of the tubular container 2.

That is, when the internal pressure of the blood test container 71 is reduced, the blood is filtered by the hydrophilic fine particle layer 73, while drawn therethrough by a suction force created by the pressure reduction. This enables the serum or plasma in the blood to flow into the bottom portion of the tubular container 2 without the need to be separated by centrifugation. The inner container portion may be integrally connected to the separately-formed tubular container, or alternatively, integrally formed with the tubular container.

Figure 42:
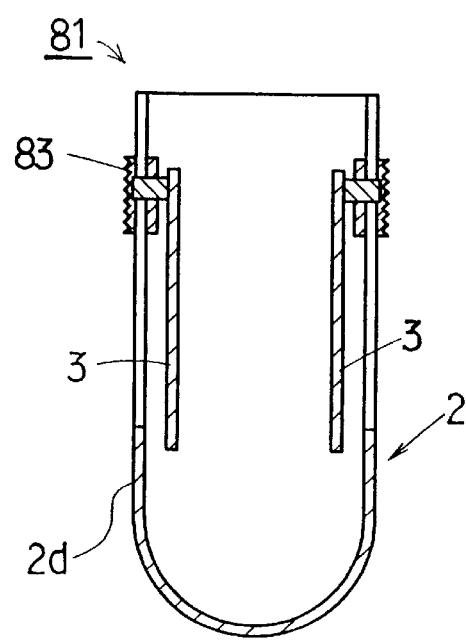
FIG. 42 is a transverse sectional view which explains the blood test container in accordance with the invention.

FIG. 42 is a sectional view, showing an exemplary construction of a blood test container in accordance with the invention. For a blood test container 81, a sliding switch 83 is provided in such a manner as to grip a side wall 2d of the closed-bottom tubular container 2, so that it is vertically moveable along the side wall 2d. The test reagent 3 is located inside the tubular container 2 where it is attached to the sliding switch 83.

The respective constructions of the sliding switch 83 and test reagent 3 are not particularly specified, so long as they meet the requirements that the sliding switch 83 should be provided in such a manner as to grip a side wall 2d of the closed-bottom tubular container 2 so that it is vertically moveable along the side wall 2d, and that the reagent 3 should be located inside the tubular container 2 where it is attached to the sliding switch 83.

Figure 43:
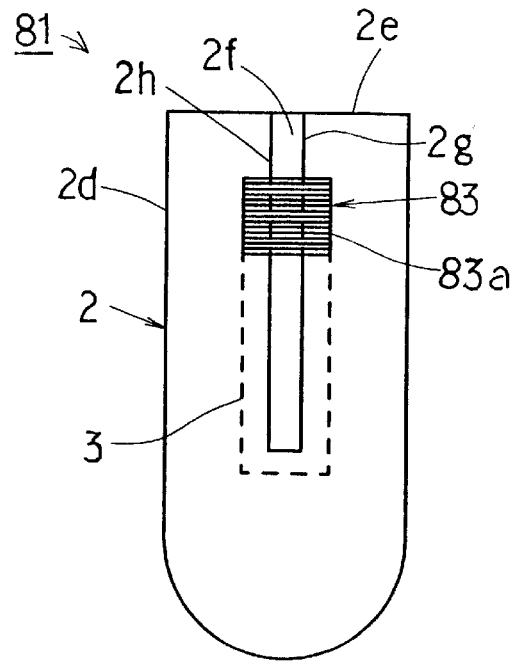
FIG. 43 is a side view of the blood test container shown in FIG. 42 to which the sliding switch is mounted, when viewed from outside of the tubular container.
Figure 44:
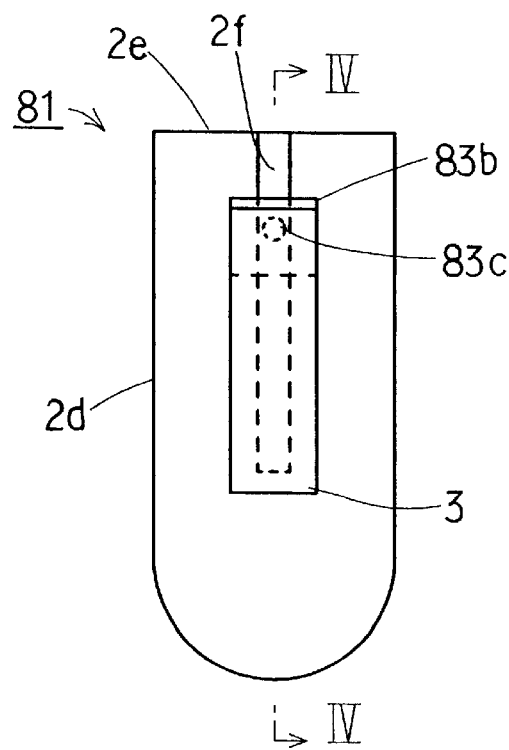
FIG. 44 is a side view of the blood test container shown in FIG. 42 to which the sliding switch is mounted, when viewed from inside of the tubular container.
Figure 45:
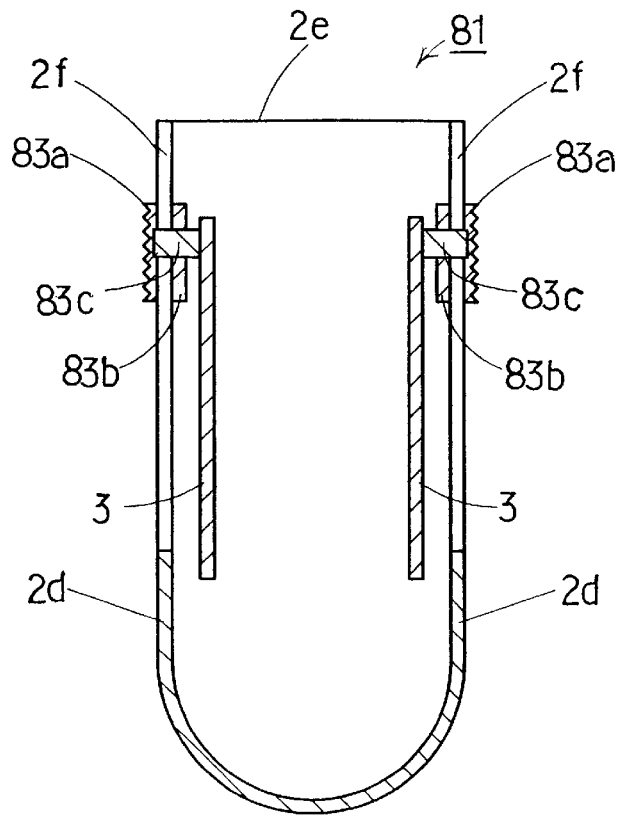
FIG. 45 is an enlarged sectional view taken along the line IV—IV of FIG. 44.

Exemplary constructions of the sliding switch 83 and test reagent 4 will be now described with reference to FIGS. 43, 44 and 45. FIG. 43 and FIG. 44 show the configuration by which the sliding switch 83 is mounted to the tubular container 2, when viewed from outside and inside of the tubular container 2, respectively. FIG. 45 is an enlarged view of a section taken along the line IV—IV of FIG. 44.

As shown in FIG. 43, an elongated parallel-side slot 2f is provided at a side wall 2d of the tubular container 2, which extends downwardly from its peripheral top edge 2e. The slot 2f has opposing side walls 2g, 2h that extend between an outer wing 83a and an inner wing 83b of the sliding switch 83, respectively. The outer and inner wings 83a, 83b of the sliding switch 83 are constructed in a thin-walled rectangular configuration, and both curved to conform to a curvature of the side wall 2d. The outer and inner wings 83a, 83b are joined to each other by a joining member 83c having a diameter smaller in dimension than a width of the slot 2f, so that they are brought into tight contact with the side walls 2g, 2h. This construction allows the sliding switch to slidably move up and down along the side walls 2g, 2h when its outer wing 83a is pushed up and down by a finger force. As also shown in FIG. 43, the outer wing 83a is irregularly surfaced to facilitate a finger operation by which the outer wing is pushed moved up and down. The joining member 83c of the sliding switch 83 suspends the test reagent 3 so as to locate it in an interior of the tubular container 2. Securement of the test reagent 3 to the joining member 83c can be accomplished by an arbitrary technique which uses, for example, a mechanical linkage, pressure-sensitive tape or adhesive. In this particular embodiment, the pressure-adhesive tape is used.

The sliding switch 83 can be made from suitable material such as synthetic resins.

The size of the tubular container 2 is not particularly specified. Any suitable size of the tubular container 2 can be chosen if the downward movement of the sliding switch 83, subsequent to blood collection and optional centrifuging, permits a part of the test reagent 3 to contact the blood, serum or plasma, leading to a reaction of the test reagent 4 with components present in the blood, serum or plasma.

Figure 46:
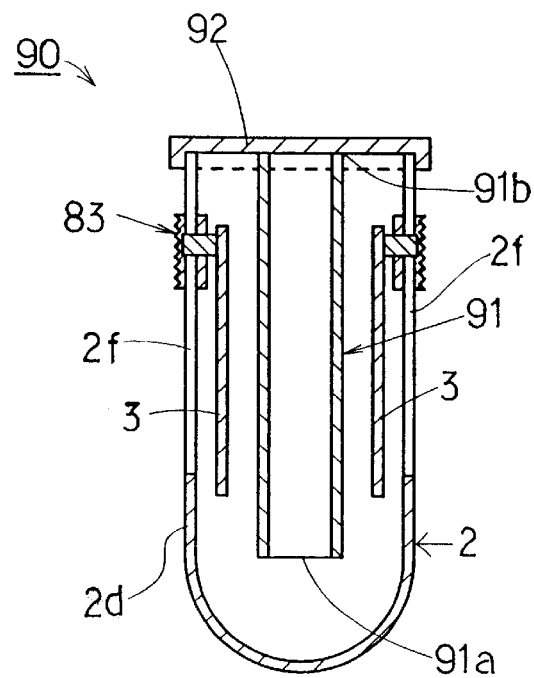
FIG. 46 is a transverse sectional view, showing an exemplary construction of the blood test container in accordance with the invention.

FIG. 46 is a sectional view, showing an exemplary construction of a blood test container 90 in accordance with the invention. A tube 91 is further added to the blood test container 1 shown in FIG. 42 so as to locate axially centrally of the tubular container 2. The tube extends from the vicinity of the top opening toward a bottom of the tubular container 2 so that its bottom end 91 is located at a position below the lowest position that the sliding switch 83 can assume.

In FIG. 46, the aforementioned tube 91 is shown as being at its top end 91b adhesively secured to a bottom portion of a stopper 92 that closes a top opening of the tubular container 2. However, other techniques such as described above can also be used to fixedly locate the tube at the above-stated position.

Figure 47:
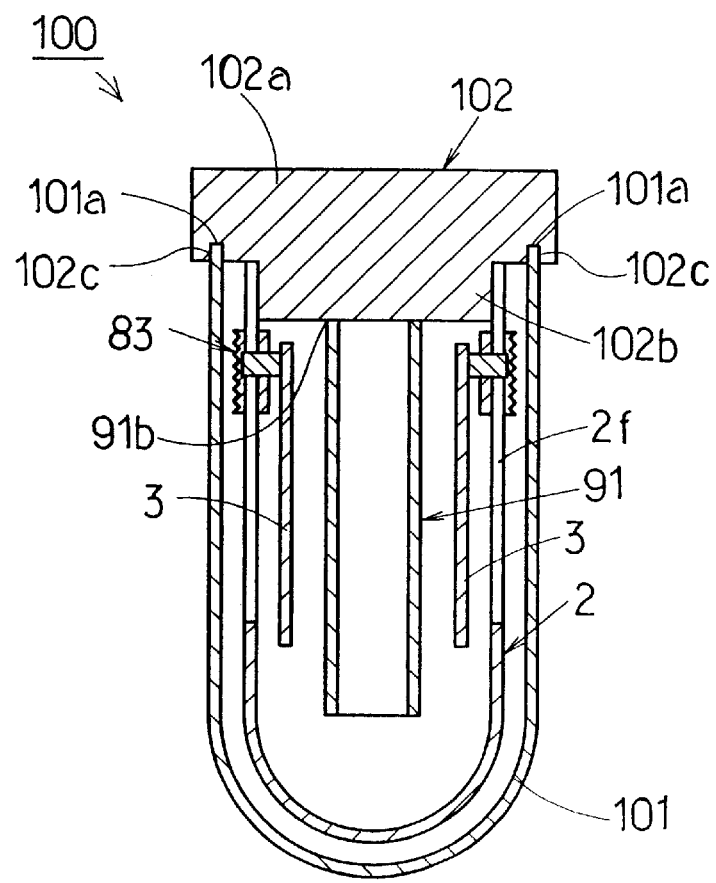
FIG. 47 is a transverse sectional view, showing an exemplary construction of the blood test container in accordance with the invention.

FIG. 47 is a sectional view, showing an exemplary construction of a blood test container 100 in accordance with the invention. A closed-bottom tubular container 101 for housing both a whole body of the tubular container 2 and the sliding switch 83, as well as a stopper 102 for closing the respective top openings of the aforementioned two tubular containers 2 and 101, are added either to the blood test container 81 shown in FIG. 42 or the blood test container 90 shown in FIG. 43 (although FIG. 47 illustrates a case where the blood test container 90 shown in FIG. 46 is used, the stopper 92 used for the blood test container 90 is replaced by the stopper 102). Also, both of the aforementioned two tubular containers 2 and 101 are internally reduced in pressure.

The stopper 102 has a larger diameter upper portion 102a and a smaller diameter lower portion 102b. An outer face of the lower portion 102b is sized to be fittingly received by an inner face of a top opening portion of the tubular container 2. The larger diameter upper portion 102a has at its bottom portion a groove 102c into which a top opening edge 101a of the outer tubular container 101 can be inserted in an air-tight fashion.

The aforementioned tube 91 is at its top end portion 91b joined to a bottom portion of the lower portion 102b of the stopper 102. Joining can be achieved by a technique which utilizes, for example, a pressure-sensitive tape, adhesive or mechanical engagement.

In the assembly of the aforementioned blood test container 100, the reduction in internal pressure of the above-described two tubular containers 2 and 101 can be performed according to the following procedure. The stopper 102 (to which the tube 91 has been previously joined) is fittingly inserted into the top opening of the tubular container 2 carrying the sliding switch 83. This blood test container, together with the outer tubular container 101, are placed within a chamber provided with a pressure-reducing equipment, such as a vacuum pump, and then reduced in pressure to a desired level. Thereafter, the peripheral edge 101a of the top opening of the outer tubular portion 101 is fittingly inserted into the groove 102c provided in the upper portion 102a of the stopper 102. This procedure enables the pressure reduction of an interior of the tubular container 2. Otherwise, the reduction in internal pressure of the tubular container 2 will fail even if the stopper 102 is fitted therein, because the slot 2f for attachment of the sliding switch 83 defines an air passage that prevents the interior of the tubular container 2 from being brought into an air-tight condition.

Figure 48:
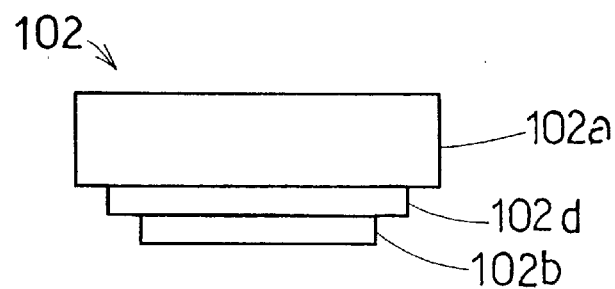
FIG. 48 is a side view which explains an alternative embodiment of the stopper for use in the blood test container shown in FIG. 47.

For the stopper 102, the provision of the groove 102c on its upper portion 102a is not essential. The stopper 102 may be constructed in a configuration shown in FIG. 48. As shown in FIG. 48, the stopper 102 further includes an intermediate diameter middle portion 102d located between the larger diameter upper portion 102a and the smaller diameter lower portion 102b. The middle portion 102d is configured such that its peripheral surface is fittingly received by the inner face of the open end of the outer tubular container 101. The inner face of the open end of the inner tubular container 2 is designed to fittingly receive the peripheral surface of the lower portion 102b.

The degree of the aforementioned pressure reduction is selected such that blood can be introduced immediately into the interior of tubular container 2 when a blood-collecting needle is at one end inserted into a patient's blood vessel and at another end inserted through the stopper 102. In general, the tubular containers 2 and 101 are reduced in internal pressure to about 0.1–0.9 atmospheric pressure.

The outer tubular container 101 can be formed from suitable materials such as synthetic resins and glasses, preferably from transparent materials, as analogous to those used to form the above-described inner tubular container 2.

The material used to form the stopper 102 is not particularly specified, and may be a natural or synthetic rubber having rubber elasticity, such as silicone or butyl rubber.

Figure 49:
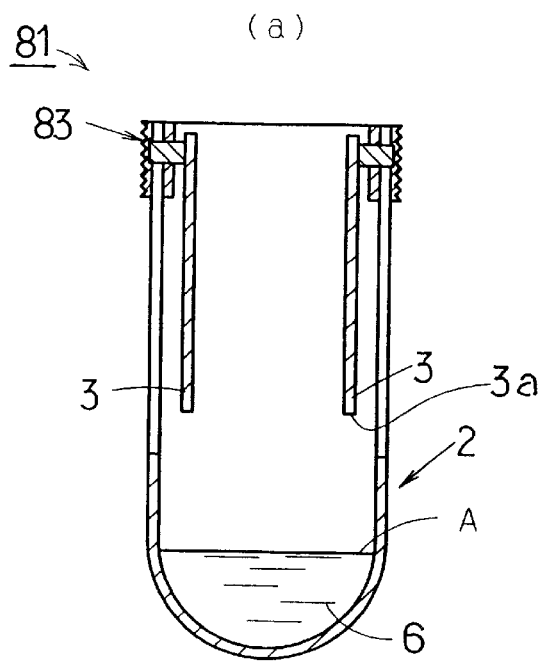
FIGS. 49(a) and 49(b) show the blood test container illustrated in FIG. 42 while it is in use.
Figure 49:
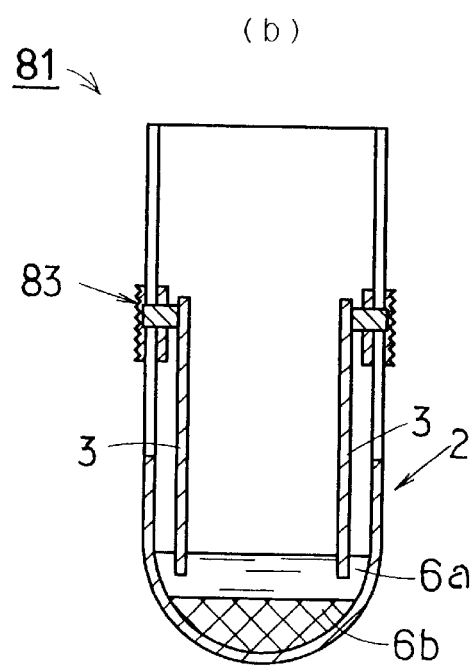
Figure 50:
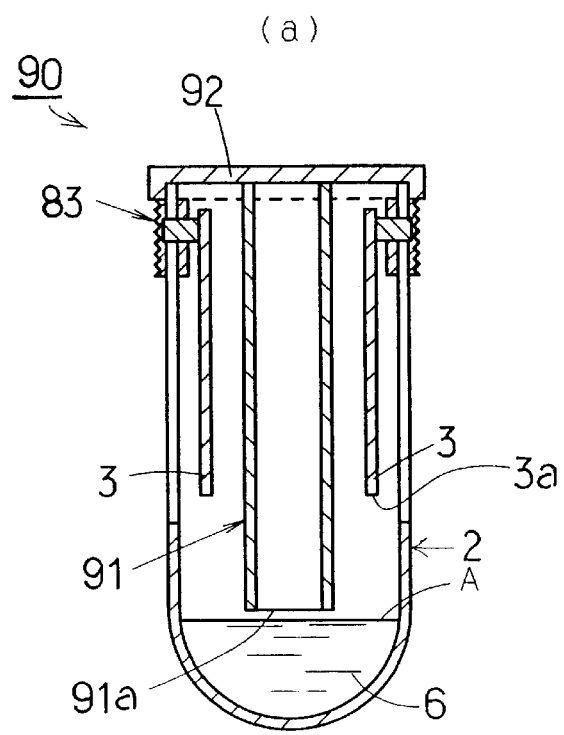
FIGS. 50(a) and 50(b) show the blood test container illustrated in FIG. 46 while it is in use, FIG. 49 (a) is its sectional view when the blood is introduced thereinto
Figure 50:
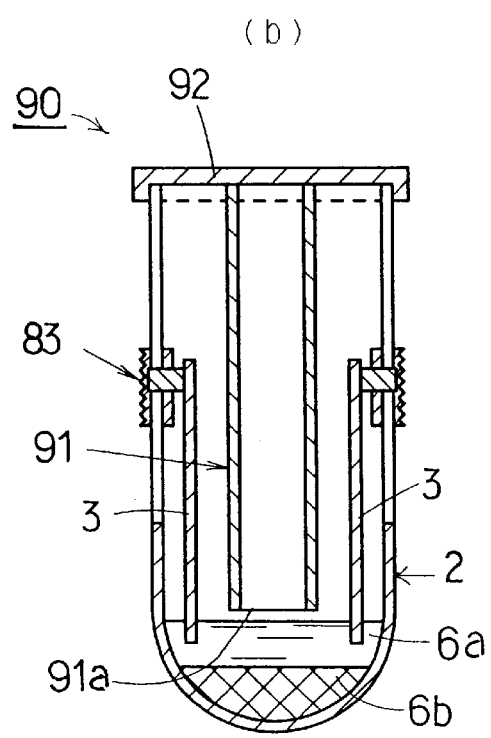

For blood test containers 81, 90 and 100 respectively shown in FIGS. 42, 46 and 47, the sliding switch 83 is set at the highest position during collection of blood 6 and centrifugation, as shown in FIGS. 49(a), 50(a) and 51(a). Preferably, the blood 6 is collected such that a blood level A does not reach the lower edge 3a of the test reagent 3, for the purpose of preventing the contact of the blood 6 and the test reagent 3. The subsequent centrifuging causes the blood 6 to separate into the serum or plasma 6a and the blood clot or cell 6b, as respectively shown in FIGS. 49(b), 50(b) and 51(b). After centrifugation, the sliding switch 83 is moved downwardly to contact a part of the test reagent 3 with the serum or plasma 6a for determination of components present therein. For the blood test container 100 shown in FIG. 47, the outer tubular container 101 is removed before the sliding switch 3 is moved downwardly.

The centrifuging may be performed at 500–5,000 r.p.m. for about 3–30 minutes, preferably at 500–3,000 r.p.m. for about 5–25 minutes.

FIGS. 42, 46 and 47 show that a pair of test reagents 3, 3 are provided facing toward each other. However, the test reagent 3 may be singularly provided in a single location.

Exemplary constructions of a blood test container in accordance with the invention as recited in claims 24–26 will be now described with reference to FIGS. 53 through 55.

Figure 53:
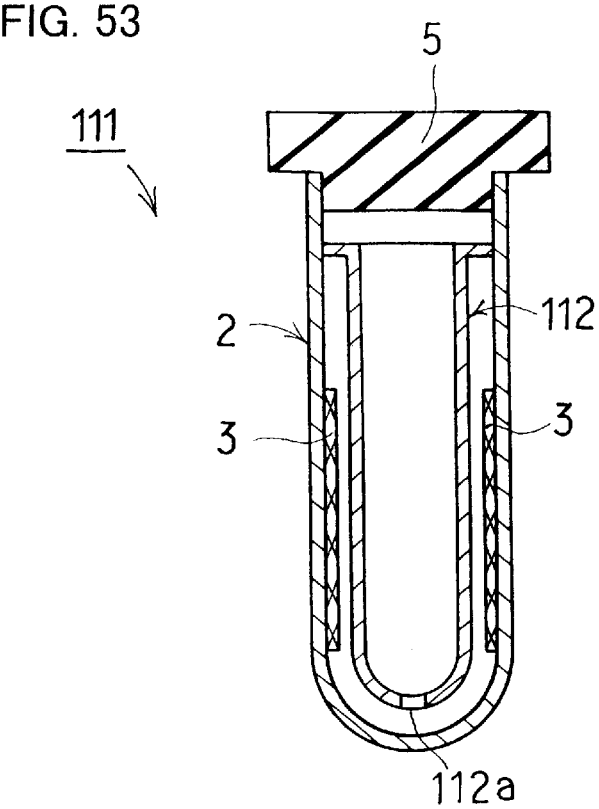
FIG. 53 is a transverse sectional view which explains an exemplary construction of the blood test container in accordance with the invention.

FIG. 53 is a transverse sectional view of a blood test container as recited in claim 24. For this blood test container 111, a second tubular container 112 having a closed bottom is accommodated within a closed-bottom tubular container 2 having a larger diameter than the second tubular container 112. The second tubular container 112 has a hole 112a at its bottom. A cover member 113, in the form of a water-soluble membrane, is secured to the bottom of the second tubular container 112 to close the hole 112a.

The test reagents 3, 3 are secured either to an outer face of the second tubular container 112 or to an inner face of the tubular container 2. The blood test reagents 3, 3 may be secured to the outer face of the second tubular container 112, although they are shown in FIG. 53 as being secured to the inner face of the tubular container 2.

Those materials used to form the tubular container, second tubular container and blood test reagent for the invention as recited in claim 12 can also be utilized to form the above-described tubular container 2, second tubular container 112 and blood test reagent 3, respectively.

The stopper 5 is further provided to close the tubular container 2.

The stopper 5 can be formed from suitable materials such as rubber and synthetic resins.

The material of the water-soluble membrane used to form the cover member 113 is not particularly specified, so long as it can be solubilized by a water content in blood, serum or plasma. Examples of materials which can form the water-soluble membrane include natural polymers, semisynthetic materials and synthetic polymers. Examples of natural polymers include chitin, chitosan, casein, collagen, egg albumin, starch, seaweeds, carrageenan, sodium alginate, agar, xanthane gum, pullulan and the like.

Examples of semisynthetic materials include dextrin, methyl cullulose, carboxy methyl cellulose and the like.

Examples of synthetic polymers include polyvinyl alcohol, sodium polyacrylate, polymethacrylic acid, polyacrylamide, polyethylene oxide, polyetylene glycol and the like.

Exemplary commercial products usable to form the water-soluble membrane include SOLUBLON, name used in trade and manufactured by Daicel Chemical Co., Ltd.; KURAREAR, name used in trade and manufactured by Kuraray Co., Ltd.; TOSLON, name used in trade and manufactured by Tokyo Cellophane Co., Ltd.; HI-CELLON, name used in trade and manufactured by Nippon Synthetic Film Co., Ltd.; VINYLON Film, name used in trade and manufactured by Kuraray Co., Ltd.; BOBLON, name used in trade and manufactured by Nippon Synthetic Film Co., Ltd.; EXCEED, name used in trade and manufactured by Okura Kogyo Co., Ltd.; EVAL, name used in trade and manufactured by Kuraray Co., Ltd.; and the like.

When in use, blood is introduced into the second tubular container 112. In an initial condition, the blood is held staying in the second tubular container 112 and thus its contact with the blood test reagent 3, 3 is prevented. That is, the cover member 113 that closes the hole 112a functions to prevent the blood under the initial condition from contacting the blood test reagent.

With the lapse of time, an increasing fraction of the cover member 113 dissolves into the water content of the blood to finally allow the blood to flow into a space between the outer face of the second tubular container 112 and the inner face of the tubular container 2 and reach the blood test reagents 3, 3, whereby a reaction thereof is caused to proceed.

The reaction results can be observed visually from outside, or alternatively, measured by a suitable measuring equipment such as a spectro photometer, reflected light reading equipment or camera.

The serum or plasma may be brought into contact with the blood test reagents 3, 3, after the blood has been introduced into the second tubular container 112 and then centrifuged. In this case, the cover member 113 is solubilized by the water content in the serum or plasma to allow the serum or plasma to flow into the space defined between the outer face of the second tubular container 112 and the inner face of the tubular container 2 and then contact the blood test reagents 3, 3.

While centrifuged, the blood test container 111 may be maintained in the orientation as shown in FIG. 53. Alternatively, the blood test container 111 while centrifuged may be maintained in the reversed orientation and then turned upside down after the centrifuging.

The aforementioned stopper 5 may be attached to the tubular container 2. The subsequent reduction in internal pressure of the tubular container 2 and second tubular container 112 will then allow the blood to be introduced into the second tubular container 112 by a vacuum blood-collecting technique.

By the use of the blood test container 111 shown in FIG. 53, the determination of components in the blood can be efficiently accomplished while a chance for a tester to contact blood during a period from collection of the blood until test results are obtained is effectively reduced.

Particularly when a vacuum blood-collecting technique is employed, a chance for an examiner to contact blood during a whole process starting from blood collection and ending with attainment of test results is further reduced. The employment of this technique is thus desirable.

Figure 54:
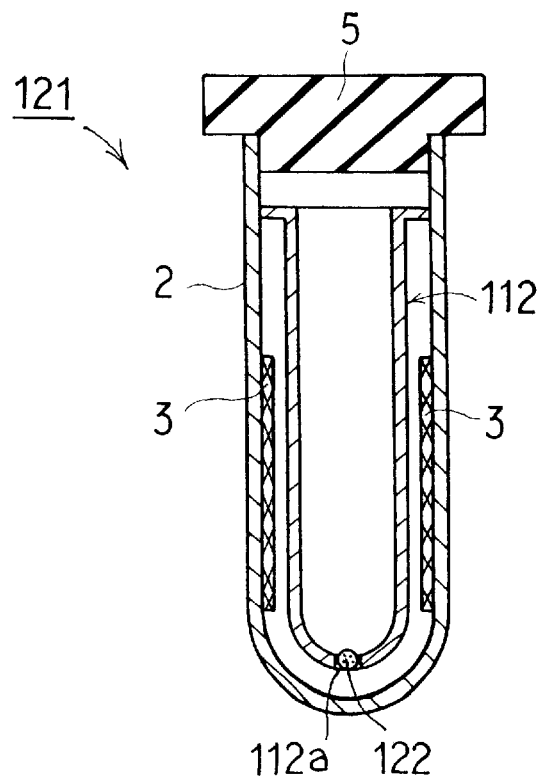
FIG. 54 is a transverse sectional view, showing an exemplary construction of the blood test container in accordance with the invention.

FIG. 54 is a sectional view, illustrating a blood test container 121 in accordance with the invention as recited in claim 25. This blood test container 1 is identical in construction to the blood test container 111 shown in FIG. 53, with the exception that the hole 112a pierced in a bottom of the second tubular container 112 is closed by a cover member 122 formed of a metal. The cover member 122 is positioned to close an inner face side of the hole 112a. Due to the presence of the cover member 122, the blood introduced into the second tubular container 112 is prevented from passing through the hole 112a into the tubular container 2.

In the measurement, the cover member 122 may be moved to open the hole 112a by using an external magnet. That is, a magnetic force is utilized to move the cover member 122 to open the hole 112a. Then, the blood introduced or the serum or plasma centrifugally separated therefrom is allowed to flow into the space defined between the inner face of the tubular container 2 and the outer face of the second tubular container 112. The measurement can thus be carried out in the same manner as for the blood test container 111 shown in FIG. 53.

Preferably, paramagnetic materials, such as iron and nickel, whose motion is controllable by a magnet, are used to form the cover member 122.

Alternatively, the cover member 122 itself may be formed from a magnet. In such a case, a motion of the cover member 122 can be controlled by an external metal plate formed of paramagnetic material, such as an iron plate.

Figure 55:
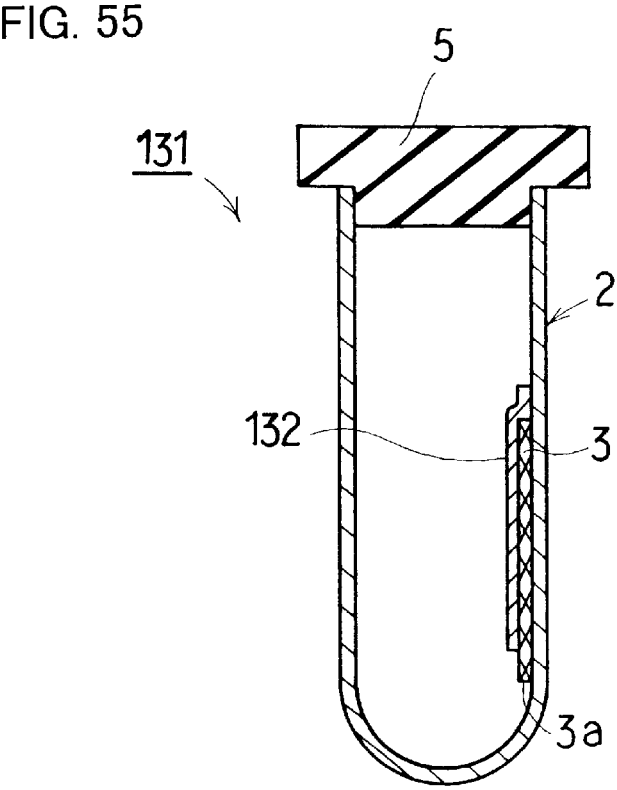
FIG. 55 is a transverse sectional view, showing an exemplary construction of the blood test container in accordance with the invention as recited in claim 26.

FIG. 55 is a sectional view which explains a blood test container 131 in accordance with the invention.

In this embodiment, the blood test reagent 3 is secured onto an inner face of the tubular container 2. The blood test reagent 3 surface is exposed only at its bottom region 3a adjacent a bottom end, and its remaining surface region is covered with a protective layer 132.

The blood test reagent 3 can be secured onto an inner face of the tubular container 2 by an arbitrary method, such as by using an adhesive or pressure-sensitive adhesive. Any material can be used to form the protective layer 132 which serves to prevent contact of the blood test reagent 3 with blood, so long as it can actually prevent the contact of the blood test reagent 3 with the blood. Suitable materials include glass, synthetic resins such as polyethylene terephthalate, and the like. Preferably, the protective layer is rendered transparent so that visual observation of changes of the blood test reagent from outside is permitted.

The cover layer 132 is positioned to leave only the reaction-initiating bottom region 3a uncovered and cover all surfaces of the remaining region of the blood test reagent 3.

In the measurement, blood or blood component, after being introduced into the tubular container 2, is left at rest. In this case, only the bottom region 3a of the blood test reagent 3 is immersed in the blood or blood component to initiate a reaction.

For the blood test container 131 shown in FIG. 55, only a part of the blood test reagent is immersed in the blood or its component and a major part of the blood test reagent 3 is prevented from being wetted.

Exemplary constructions of a blood test container 141 in accordance with the invention are now specifically described with reference to FIGS. 56(a) and 56(b)–FIGS. 58(a) and 58(b).

For the blood test container 141 shown in FIG. 56(a), the aforementioned contact control structure is positioned within the tubular container 2 and an inner tube 142 formed of a flexible resin is further provided. An outer surface portion of the inner tube 142 is brought into close contact with an inner face of the tubular container 2. However, an upper portion of the inner tube 142 is configured to have a declining diameter toward its top end, i.e., have an outer diameter smaller smaller than an inner diameter of the tubular container 2 so that a peripheral surface of the inner tube 142 upper portion is spaced from the inner face of the tubular container 2.

A communicating member 143 is provided in the space defined between the inner face of the tubular container 2 and the peripheral surface of the inner tube 142 such that it is moveable in a length direction of the tubular container 2. The form of the communicating member 143 is not particularly specified, so long as it is permitted to move in the length direction of the tubular container 2. The communicating member may be provided in the form of beads, an annular ring or the like.

The inner tube 142 can be made from various materials, so long as it is made flexible and its lower portion can be brought into close contact with the inner surface of the tubular container 2. Examples of suitable materials include polypropylene, polyethylene, soft vinyl chloride, nylon, polyurethane foam and the like. In the case of a thin-wall inner tube, polyethylene terephthalate, polycarbonate, rigid vinyl chloride and the like can also be used, for example. In such a case, the wall thickness of the inner tube 142 may preferably be selected such that its lower portion is made flexible and elastic sufficient to be brought into close contact with the inner face of the tubular container 2.

The material used to form the communicating member 143 is not particularly specified, so long as it permits the member to move in the length direction of the tubular container 2. Useful materials include suitable glasses, metals and synthetic resins such as nylon, polypropylene and polyethylene terephthalate.

For the blood test container 141, the blood test reagent 3 is secured onto an inner face of the tubular container 2. The blood test reagent 3 used in the invention shown in FIGS. 1 and 2 can also be used for the blood test reagent 3 in this embodiment. The technique used for securement is not particularly specified.

The blood test reagent 3 must be secured in a position above a bottom end of the tube 142 portion which is held in close contact with the inner face of the tubular container 2. This is purposed to prevent the contact of the blood introduced with the blood test reagent 5 by locating the blood inside the contact region of the inner tube 142 and tubular container 2 and placing the blood test reagent outside the contact region.

Figure 56:
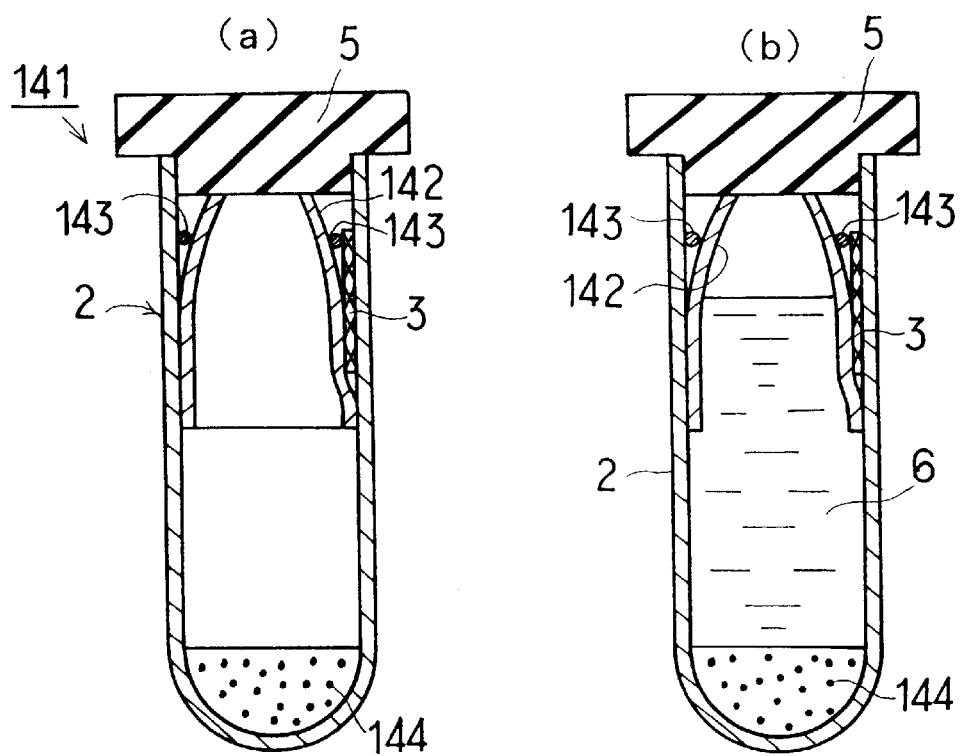
FIGS. 56(a) and 56(b) are transverse sectional views showing an exemplary construction of the blood test container in accordance with the invention, respectively.

For the blood test container 1 shown in FIG. 56, a separating medium 144 is accommodated in the tubular container 2 to reside at its bottom portion. The separating medium 144 can be comprised of materials suitable for the separation of serum or plasma from solid matter, respective produced when blood is centrifuged, and may be comprised principally of chlorinated polybutene (Patent Laying-Open No. Sho 55-43462), a modified oligomer of cyclopentadiene (Patent Laying-Open No. Hei 2-95257), α-olefin.maleic diester copolymer (Patent Laying-Open No. Sho 57-149964) or the like, for example. It will be recognized that the separating medium is not necessarily accommodated in the tubular container.

Also, the stopper 5 is mounted to the tubular container 2. After mounting of the stopper 5, an interior of the tubular container 2 may preferably be reduced in pressure so that blood can be introduced into the tubular container 2 by a vacuum blood-collecting technique.

In the measurement, the blood 6 is introduced into the tubular container 2, as shown in FIG. 56(b). In this instance, a projector needle may be inserted through the stopper 5 to supply the blood 6 into the tubular container. Alternatively, the blood 6 may be introduced into the inner tube 142 by a vacuum blood-collecting technique.

Although the blood 6 is introduced inside of the inner tube 142, the close contact of the inner tube 142 with the tubular container 2 prevents the blood 6 from passing across the contact region into the space between the peripheral surface portion of the inner tube 142 and the inner face of the tubular container 2. The contact of the blood 6 with the blood test reagent 3 is thus inhibited.

When left at rest for a certain period, the blood 6 is coagulated to separate into serum 6A and clot 6B, as shown in FIG. 57(a). The blood test container 141 is thereafter turned upside down and then centrifuged. As a result, the separating medium layer 144 is caused to move to a position of intermediate height, whereby the clot 6B is completely isolated from the serum 6A, as shown in FIG. 57(b). Concurrently, the communicating member 143 is caused to move downward, so that the contact area of the inner tube 142 and tubular container 2 is reduced.

When the centrifugation is repeated, the communicating member 143 is caused to move further downward. In this instance, the downward movement of the communicating member 143 results in the formation of a clearance between the peripheral surface of the inner tube 142 and the inner face of the tubular container 2, as shown in FIGS. 58(a) and (b). The serum 6A separated is then allowed to pass through the clearance into the space, defined between the the outer face of the inner tube 142 and the inner face of the tubular container 2, where it contacts the blood test reagent 3 and a reaction therebetween is allowed to proceed.

In the situation shown in FIG. 58(b), the communicating member 143 has already fallen onto the separating medium layer 144 and the outer face of the inner tube 142 has been brought again into close contact with the inner face of the tubular container 2. However, the reaction in the blood test reagent 3 is sustained.

Accordingly, the reaction results can be observed visually from outside, or alternatively, measured by a suitable measuring equipment such as a spectro photometer and a camera, as described earlier.

Figure 57:
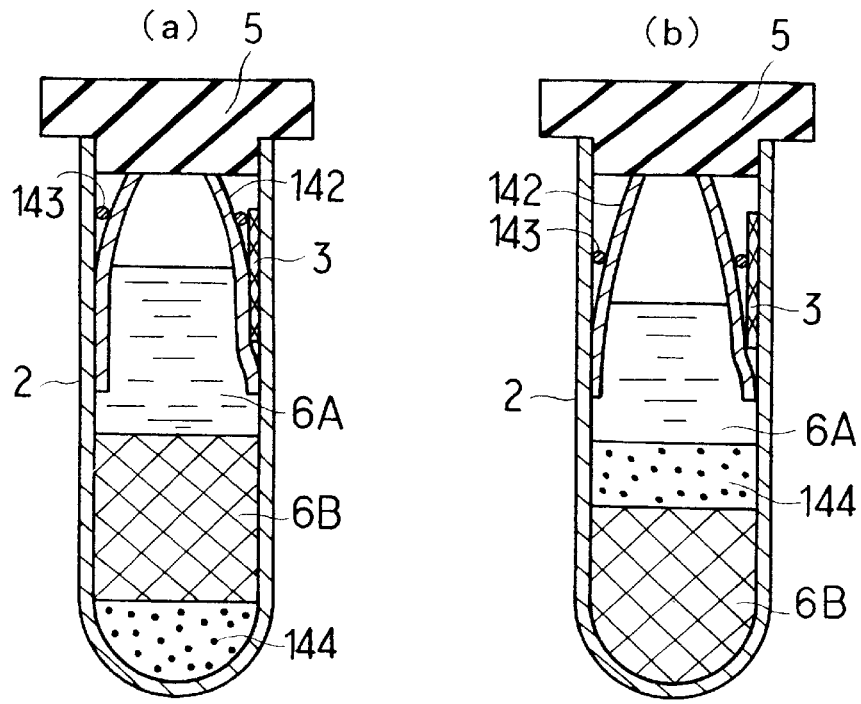
FIGS. 57(a) and 57(b) are transverse sectional views showing an exemplary construction of the blood test container in accordance with the invention, respectively.
Figure 58:
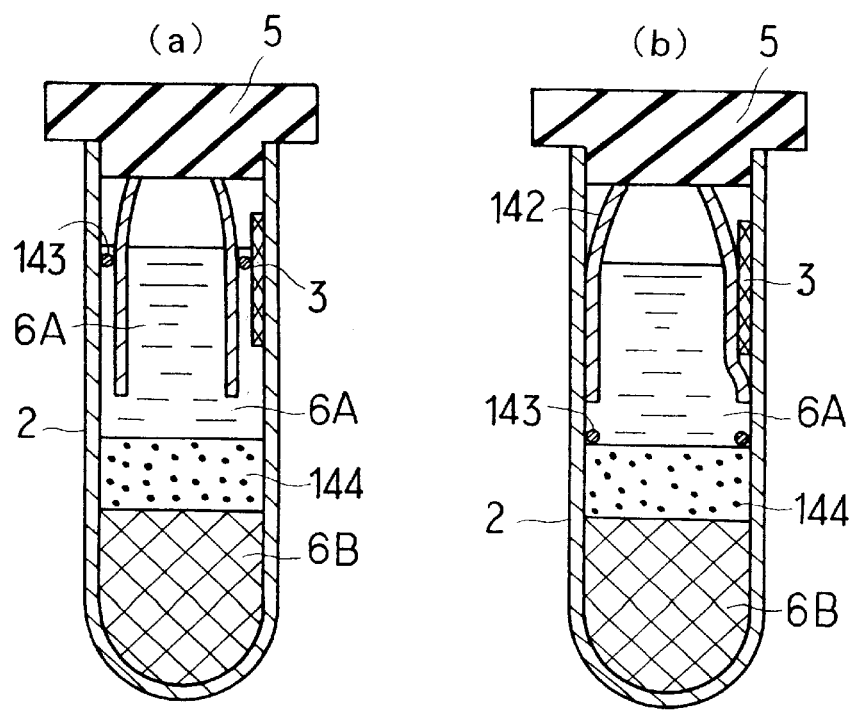
FIGS. 58(a) and 58(b) are transverse sectional views which explain measuring steps, with the use of the blood test container in accordance with the invention, respectively.

For the blood test container shown in FIG. 56–FIG. 58, there hardly exists a chance for a tester to contact blood because a whole process from blood collection till acquisition of measurement results is performed within the tubular container 2. This accordingly results in the safe and efficient measurement of the blood or blood components.

Figure 60:
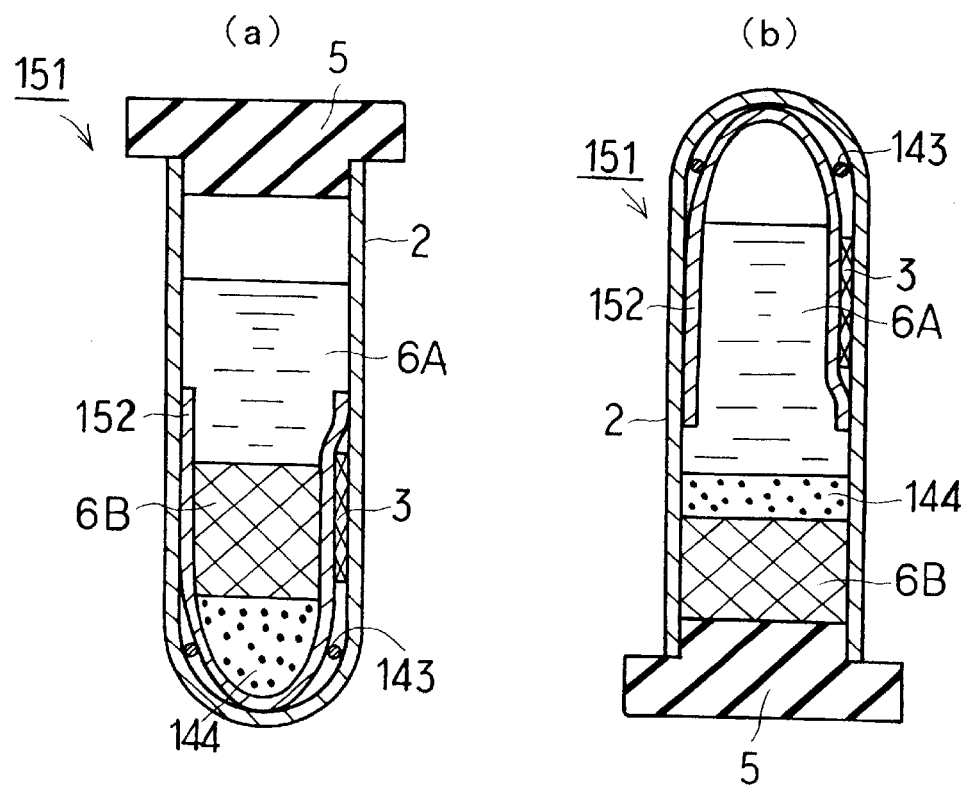
FIGS. 60(a) and 60(b) are transverse sectional views, showing the condition where the serum and solid matter in the blood test container shown in FIG. 59 were separated from each other and the condition where the container was turned upside down, respectively.
Figure 61:
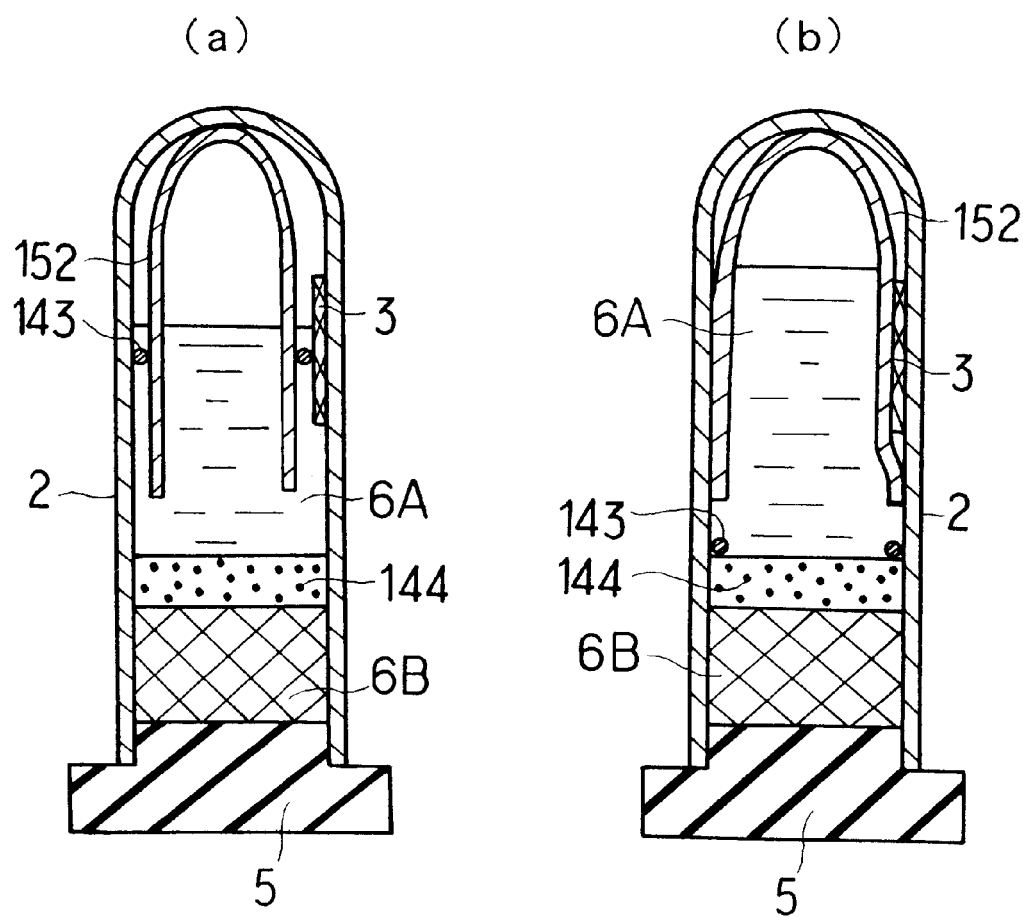
FIGS. 61(a) and 61(b) are transverse sectional views which explain measuring steps, with the use of the blood test container in accordance with the invention as recited in claim 11, respectively.

A blood test container in accordance with the invention as recited in claim 11 will be now described with reference to FIG. 59–FIG. 61.

For a blood test container 151 shown in FIG. 59(a), a closed-bottom inner tube 152 is disposed such that a portion adjacent its open top end is held in close contact with an inner face of the tubular container 2. Those materials used to form the inner tube 142 of the blood test container 141 shown in FIG. 58 can also be used for the inner tube 152.

In the illustrated construction, a lower portion of the inner tube 152 is configured to have a reducing diameter, that is, its bottom-adjacent portion has a reduced outer diameter. Accordingly, a peripheral surface of the bottom-adjacent portion of inner tube 152 is spaced from an inner face of the tubular container 2. The communicating member 143 is placed within the space between the peripheral surface of the inner tube 152 and the inner face of the tubular container 2.

The blood test reagent 3 is secured to an inner face of the inner tube 152 at a position below a top end of the contact region where the inner tube 152 is held in close contact with the tubular container 2.

Figure 59:
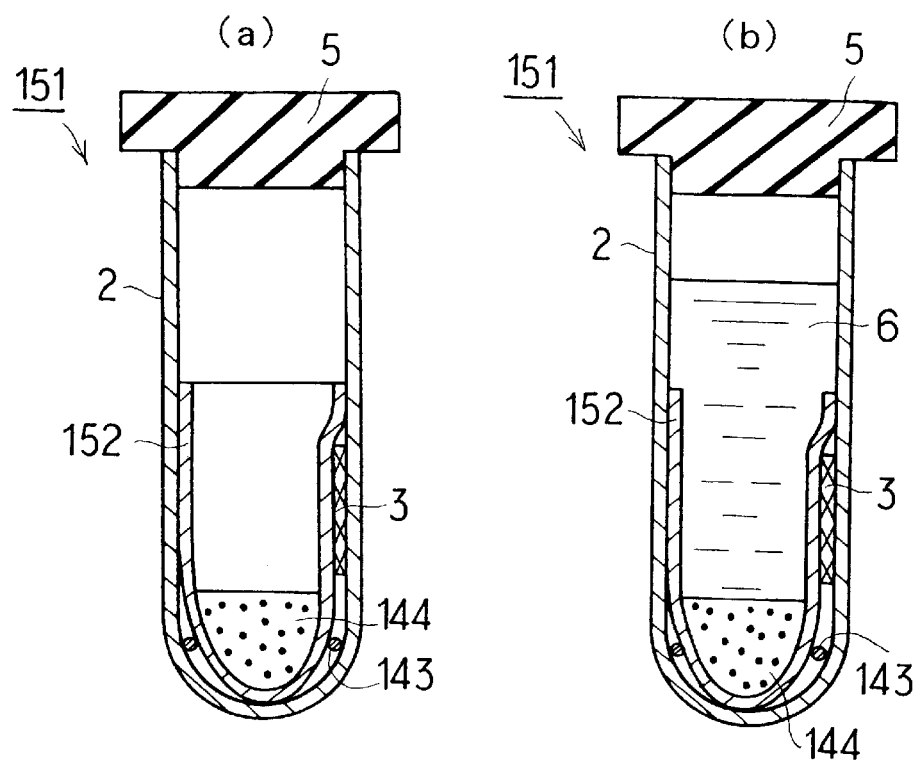
FIGS. 59(a) and 59(b) are transverse sectional views which explain the blood test container in accordance with the invention as recited in claim 11, respectively.

The blood test container 151 shown in FIG. 59 is identical in construction to the blood test container shown in FIG. 56, excepting the arrangement and configuration of the inner tube 152 and the arrangement of the communicating member and blood test reagent 5.

In the measurement, the blood 6 is introduced into the tubular container 2, as shown in FIG. 59(b). In this instance, because the top-adjacent portion of the inner tube 152 is held in close contact with the inner face of the tubular container 2, the blood 6 introduced is prevented from flowing into a space in which the communicating member 143 and the blood test reagent 3 are accommodated, i.e., prevented from flowing into a space outside the contact region where the inner tube 152 is held in close contact with the inner face of the tubular container 2. In an initial condition, the contact of the blood 6 with the blood test reagent 6 can thus be prevented.

When left to stand for a certain period, the blood 6 is coagulated to separate into serum 6A and clot 6B (shown in FIG. 60(a)).

The blood test container 151 is thereafter turned upside down and then centrifuged. As a result, the serum 6A is completely isolated from the clot 6B by the separating medium layer 144, as shown in FIG. 60(b). Since this centrifugation is performed under mild conditions, the communicating member 143 is allowed to stay above the contact region where the inner face of the tubular container 2 is held in close contact with the outer face of the tube 152.

When the centrifugation is repeated, the communicating member 143 is caused to move downward. As shown in FIGS. 61(a) and 61(b), the downward movement of the communicating member 143 results in releasing the contact of the outer surface of the inner tube 152 with the inner surface of the tubular container 2. This permits the serum 6A to flow into the space defined outside the inner tube 3 and contact the blood test reagent 3, whereby a reaction thereof is allowed to proceed.

In the situation shown in FIG. 61(b), the communicating member 143 has already fallen to bring the outer face of the inner tube 142 into contact with the inner face of the tubular container 2. However, the above-described reaction is sustained because the blood test reagent has already contacted the serum 6A.

Therefore, the reaction result can be observed or measured from outside in the same manner as in the case for the blood test container 141 shown in FIG. 56.

DESCRIPTION OF EXAMPLES

Specific examples of the present invention will be now described.

Example 1

A blood test container 1 as shown in FIG. 1 was assembled. A serum separating medium-containing vacuum blood-collecting tube (manufactured by Sekisui Chemical Co., Ltd., product name: INSEPACK, a 15 mm diameter and 100 mm long polyethylene terephthalate tube having an inner wall surface coated with a blood coagulation promoter) was provided. A rubber stopper was removed from the vacuum blood-collecting tube to bring its interior to a normal pressure, thereby constituting a tubular container 2.

A strip-of test paper was removed from a reaction container incorporating a single dosage QUICK CHASER HBsAg (manufactured by Mizuho Meddy Co., Ltd., about 6 cm long reagent for HBs antigen detection) to use as a detection reagent 3. The detection reagent was adhesively secured to the tubular container by using a pressure-sensitive adhesive tape such that its top end is located 8 cm above a bottom 2b of the tubular container.

The HBs antigen detection reagent (QUICK CHASER HBsAg) is an immunochromatography assay reagent based in principle on a sandwich technique. When a blood sample contacts a lower portion of the reagent, the sample blood is caused to migrate on the reagent according to a capillary phenomenon. The HBs antigen present in the blood sample reacts with anti-HBs mouse monoclonal antibody binding colloidal gold to form an HBs antigen-antibody-colloidal gold complex. This complex further migrates on a membrane filter to reach the anti-HBs mouse monoclonal antibody solid phase portion where it is bound trapped. As a result, in the case of HBs antigen positive, a red purple line derived from the colloidal gold is caused to appear in the solid phase portion, but not in the case of HBs antigen negative. Whether HBs antigen positive or negative can thus be visually determined.

Blood was injector collected from human subjects A, B and C. 7 ml of each sample blood collected was transferred into the blood test container of the present Example which was left to stand for 10 minutes. Each sample blood was then centrifuged at 3,000 r.p.m. for 10 minutes by using a centrifugal separator (manufactured by a domestic company, product name: H-20). As a result, the blood was separated into serum 6a and solid matter 6b (refer to FIG. 3(b)).

After centrifuged, the container was left to stand for 10 minutes. The serum 6a was thereafter contacted with the reagent 3. The results proved HBs antigen negative for all the subjects, A, B and C.

Example 2

Figure 4:
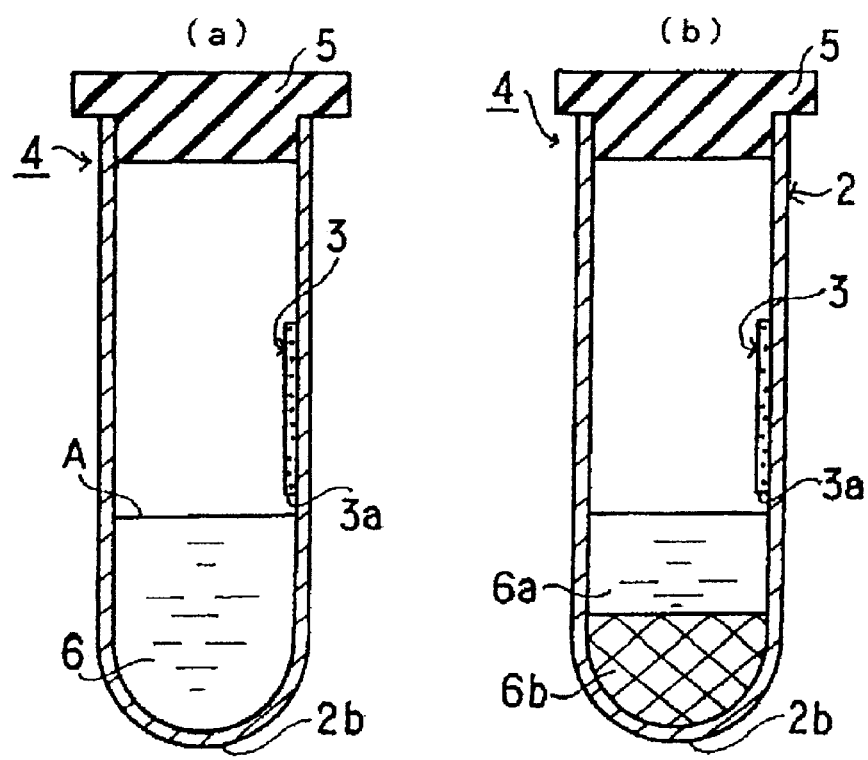
FIGS. 4(a) and 4(b) are transverse sectional views which explain blood test procedures when the blood test container shown in FIG. 2 is used, respectively.

A blood test container 4 as shown in FIG. 4 was assembled. That is, the rubber stopper was removed from the serum separating medium-containing vacuum blood-collecting tube used in Example 1 to prepare a tubular container 2, the reagent 3 was secured within the tubular container 2 in the same manner as in Example 1, and the rubber stopper 5 was attached at 0.26 atmospheric pressure by using a vacuum capping machine VS-150A (manufactured by Kyowa Shinku, Co., Ltd.) to obtain the blood test container 4, as shown in FIG. 4, which carried the stopper 5 and was constructed to permit vacuum collection of 7 ml blood.

By using this blood test container 4, blood samples were collected for evaluation from the subjects A, B and C in the same manner as in Example 1. The results proved HBs antigen negative for all blood samples from the subjects, A, B and C.

Example 3

A blood test container 7 as shown in FIG. 5 was assembled. The rubber stopper was removed from the vacuum blood-collecting tube used in Example 1 to prepare a tubular container 2. A cone-shaped polyethylene container (having an inner wall surface coated with a blood coagulation promoter) having a maximum diameter of 15 mm, a minimum diameter of 6 mm and a thickness of 0.1 mm, as an inner tubular portion 8, was inserted into the tubular container 2. A 6 mm diameter polystyrene bead (manufactured by Sekisui Chemical Co., Ltd., product name: POLYSTYRENE BEAD #45), as a solid member 9, was adhesively secured to a bottom end of the inner tubular portion 8.

A conjugate liquid attached to a single-dosage HBs antigen detection reagent (product name: DYNASCREEN HBsAg, manufactured by Dynabbot Co., Ltd.) was dropped by the amount of 50 μl onto an upper end of a reagent plate to prepare a test reagent 3 which was subsequently secured to an inner wall of the tubular container 2 by using a pressure-sensitive adhesive tape.

The blood test container 7 such assembled was used to collect blood samples from the subjects A–C in the same manner as in Example 1. Each sample blood was left at rest for 10 minutes and then centrifuged at 3,000 r.p.m. for 10 minutes by using a centrifugal separator (manufactured by a domestic company, product name: H-20). As a result, the solid member 9 was forced to fall while the blood was caused to separate into serum and clot. After the centrifuging, the container was left to stand for 10 minutes. Example 1 was then followed to subsequently contact the serum with the test reagent 3, which resulted in proving HBs antigen negative for all the subjects, A, B and C.

Example 4

A blood test container 7 as shown in FIG. 6 was assembled. In addition to the HBs antigen detection reagent, an HBs antibody detection reagent (manufactured by Dynabbot Co., Ltd., product name: single dosage DYNASCREEN O-SUB) was further secured to the blood test container 7 assembled in Example 3. The rubber stopper was attached at 0.26 atmospheric pressure by using a vacuum capping machine (manufactured by Kyowa Shinku, Co., Ltd., product name: VS-150A) to permit vacuum collection of 7 ml blood. By using the blood test container thus obtained, evaluation was made in the same manner as in Example 3 resulting in proving HBs antigen negative and HBs antibody negative for all the subjects A–C.

Example 5

A blood test container 10 as shown in FIG. 7 was assembled. In the same manner as in Example 1, a rubber stopper was removed from the serum separating medium-containing vacuum blood-collecting tube (manufactured by Sekisui Chemical Co., Ltd., product name: INSEPACK) to bring its interior to a normal pressure, thereby preparing a tubular container 2. A 6 mm diameter and 60 mm long polypropylene tube (having an inner wall surface coated with a blood coagulation promoter) was used to constitute a second tubular container 11. A 5 μm pore-size filter was removed from MILLEX-SV, manufactured by Millipore Co., Ltd., and cut to provide a 10 mm diameter porous plate which was then secured onto a bottom face of the second tubular container 11 by a pressure-sensitive adhesive tape.

The HBs antigen detection reagent and HBs antibody detection reagent, same in type as those used in Example 4, were then secured onto an inner wall surface of the tubular container 2 in the same manner as in Example 1. Thereafter, the second tubular container 11 was adhesively secured to a bottom face of the stopper which was subsequently attached to the tubular container 2 for insertion of the second tubular container therein.

The second tubular container may be directly secured to the inner face of the tubular container as by using an adhesive or a bridge.

The blood test container 10 such assembled was used to collect blood samples from the subjects A–C in the same manner as in Example 1. Each sample blood was left at rest for 10 minutes, centrifuged at 3,000 r.p.m. for 10 minutes by using a centrifugal separator (manufactured by a domestic company, product name: H-20) and then left to stand for 10 minutes. The visual observation of the reagents through a container outer wall led to proving HBs antigen negative and HBs antibody negative for all the subjects A–C.

Example 6

An interior of the tubular container 2 of the blood test container as prepared in Example 5 was reduced in pressure to provide a blood test container 10 shown in FIG. 8. In this instance, pressure reduction was achieved by using a vacuum capping machine (manufactured by Kyowa Shinku, Co., Ltd., product name: VS-150A) which placed the rubber stopper on the container at 0.85 atmospheric pressure to permit vacuum collection of 1 ml blood.

The blood test container such assembled was used to collect blood samples from the subjects A–C. After left to stand for 10 minutes, each sample blood was centrifuged in the same manner as in Example 5. As a result, each blood sample separated into serum 6a and clot 6b, as shown in FIG. 10(b). Subsequent to the centrifuging, each container was left to stand for 10 minutes to observe the reagents 3. The results proved HBs antigen negative and HBs antibody negative for all the subjects A–C.

Example 7

A blood test container 13 shown in FIG. 11 was assembled. The serum separating medium-containing vacuum blood-collecting tube used in Example 1 was utilized for a tubular container 2.

The stopper was removed from the tubular container 2 to bring its interior to a normal pressure.

A 6 mm diameter and 60 mm long polypropylene tube (having an inner wall coated with a blood coagulation promoter) was used for a tubular member 14. A rubber was removed from a top end of a piston incorporated in a 5 ml syringe, manufactured by Nipro Co., Ltd., and centrally apertured by a cutter to provide an angular member 15 having a centrally-located, 6 mm diameter through-hole.

Then, the HBs antigen detection reagent and HBs antibody detection reagent 3, 3 were secured onto an inner wall surface of the tubular container 2 in the same manner as in Example 4.

A top end of the tubular member 14 was adhesively secured to a bottom face of the stopper and the annular member 15 was attached to the tubular member 14. The stopper was then attached to the tubular container 2 for insertion of those members thereinto, thereby obtaining a blood test container 13. The blood test container 13 such assembled was used to collect blood samples from the subjects A–C in the same manner as in Example 1. After left to stand for 10 minutes, each blood sample was centrifuged at 3,000 r.p.m. for 10 minutes by a centrifugal separator (product of a domestic centrifuge manufacturer, product name: H-20). Subsequent to the centrifuging, each container was left to stand for 10 minutes to observe the reagents 3, 3. The results proved HBs antigen negative and HBs antibody negative for all the subjects A–C.

The annular member 15 may be secured to the tubular container as by a bridge.

Example 8

A blood test container 13 shown in FIG. 12 was assembled. That is, in the assembly of the blood test container 13 in Example 7, the attachment of the stopper 5 was accomplished by a vacuum capping machine (manufactured by Kyowa Shinku, Co., Ltd., product name: VS-150A) which placed the rubber stopper on the container at 0.26 atmospheric pressure to permit vacuum collection of 7 ml blood.

Figure 14:
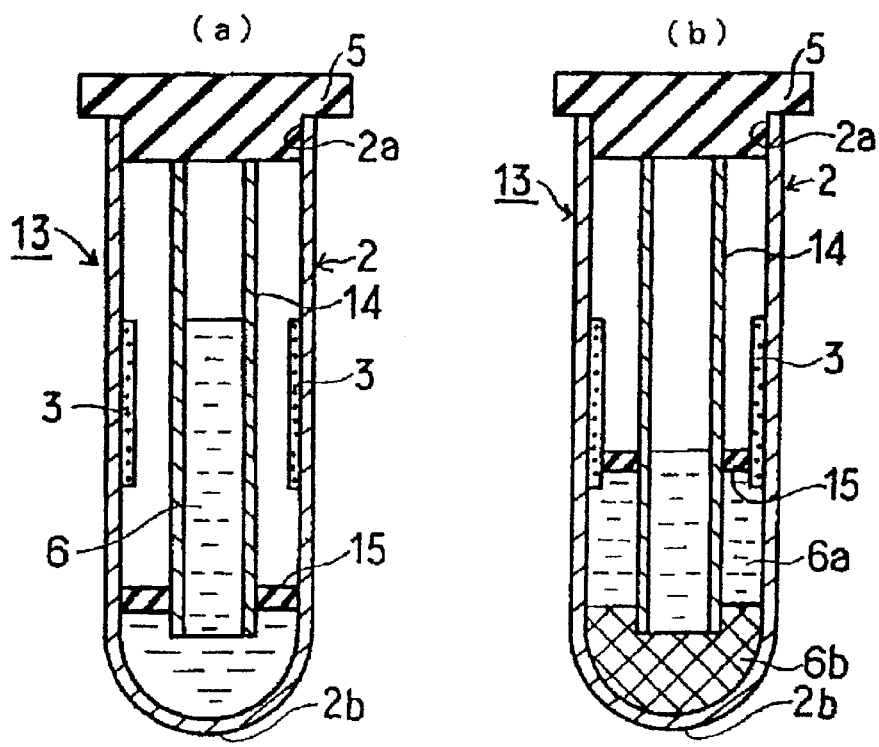
FIGS. 14(a) and 14(b) are transverse sectional views which explain blood test procedures when the blood test container shown in FIG. 12 is used, respectively.

The blood test container 13 such assembled was used to vacuum collect blood samples from the subjects A–C. As a result, the blood 6 was introduced into the tubular member 14 and reached a bottom surface of the annular member 15, as shown in FIG. 14(a). After left to stand for 10 minutes, each blood sample was centrifuged at 3,000 r.p.m. for 10 minutes by a centrifugal separator (product of a domestic centrifuge manufacturer, product name: H-20). This caused the blood to separate into serum 6a and clot 6b and also forced the annular member 15 to move upward to a position of intermediate height, as shown in FIG. 14(b). After left to stand for 10 minutes, the reagents 3 were observed for each container. The results proved HBs antigen negative and HBs antibody negative for all blood samples from the subjects A–C.

Example 9

A blood test container 16 shown in FIG. 15 was assembled. A tubular container 2 was prepared by removing the stopper from the serum separating medium-containing vacuum blood-collecting tube used in Example 1 to bring its interior to a normal pressure.

A second tubular container 17 was prepared by securing a porous plate, as fabricated according to the below-described procedure, by adhesive to a bottom of a 6 mm diameter and 60 mm long polypropylene tube (having an inner wall coated with a blood coagulation promoter).

That is, a 10 μm porous-size filter was removed from MILLEX-SV, name used in trade and manufactured by Millipore Co., Ltd., and cut to a diameter of 10 mm to provide the aforementioned porous plate. This porous plate was secured by a pressure-sensitive adhesive tape onto an open bottom of the polypropylene tube.

The test reagent 3, identical in type to that used in Example 4, was secured onto an inner wall of the tubular container 2 in the same manner as in Example 4.

A second tubular container 17 was adhesively secured to a bottom end of the stopper which was subsequently attached to the tubular container 2 for insertion of the second tubular container thereinto.

By using the blood test container 16 thus obtained, blood samples were collected from the subjects, A–C, left to stand for 10 minutes, centrifuged and evaluated in the same manner as in Example 1. After the centrifugation, each container was left to stand for 10 minutes to subsequently observe its reagent 3. Results proved HBs antigen negative and HBs antibody negative for all the subjects A–C.

The porous plate may be secured to the tubular container by adhesives or a bridge.

Example 10

A blood test container 16 shown in FIG. 16 was assembled. That is, in the assembly of the blood test container 16 in Example 9, the attachment of the stopper 5 was accomplished by a vacuum capping machine (manufactured by Kyowa Shinku, Co., Ltd., product name: VS-150A) which placed the rubber stopper on the container at 0.26 atmospheric pressure to permit vacuum collection of 7 ml blood. Other than the above, the procedure of Example 9 was followed.

Figure 18:
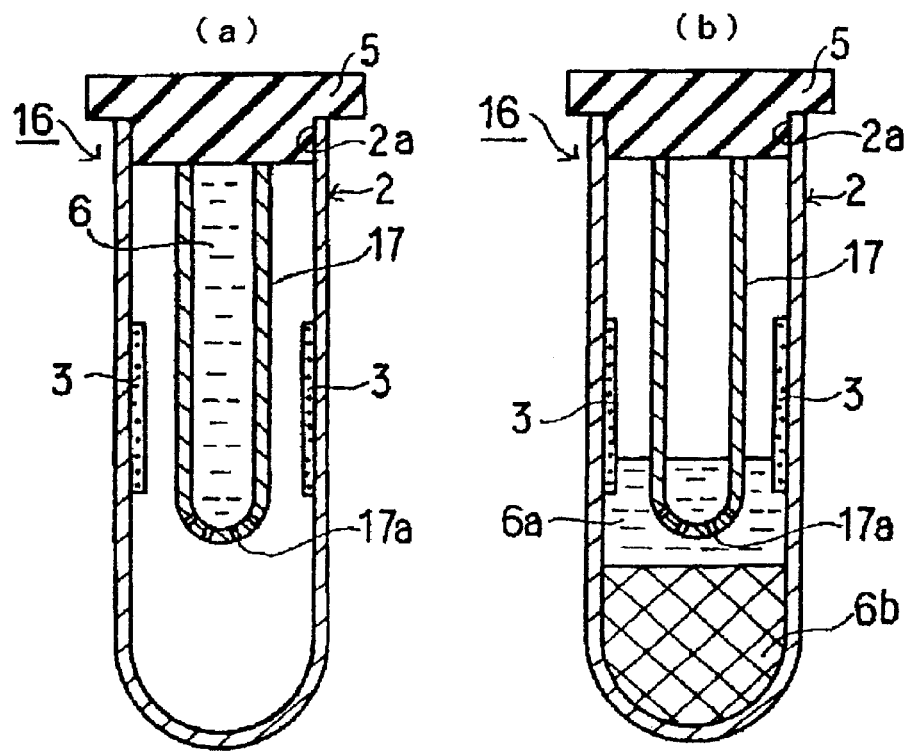
FIGS. 18(a) and 18(b) are transverse sectional views which explain blood test procedures when the blood test container shown in FIG. 16 is used, respectively.

Blood samples were collected from the subjects, A–C, by using the blood test container above obtained. As shown in FIG. 18(a), each blood sample 6 was introduced into the second tubular container 17. After the lapse of 10 minutes, each blood sample was centrifuged at 3,000 r.p.m. for 10 minutes. By this centrifuging, each blood sample, while separated into serum 6a and clot 6b, was forced to flow from the second tubular container 17 into the tubular container 2. After centrifugation, the container was left to stand for 10 minutes to subsequently observe its reagents 3. The results proved HBs antigen negative and HBs antibody negative for all the subjects A–C.

Example 11

A blood test container 18 shown in FIG. 19 was assembled. The tubular container 2 was analogous to that used in Example 1. A 6 mm diameter and 98 mm long polypropylene tube (having an inner wall coated with a blood coagulation promoter) was used for a tubular member 19. The test reagent 3, identical in type to that used in Example 4, was secured to an inner wall of the tubular container 2 in the same manner as in Example 4.

A rubber stopper originally incorporated in the tubular container 2 was used for a cap 20. The tubular member 19 was adhesively secured to a bottom face of the cap which was subsequently placed on the tubular container 2 for insertion of the tubular member therein.

Next, a blood sample from each of the subject, A–C, was collected in the blood test container 18, as analogously to Example 1, left to stand for 10 minutes and centrifuged in the same manner as in Example 1. After centrifugation, each container was left to stand for 10 minutes to subsequently observe its reagents 3. The results proved HBs antigen negative and HBs antibody negative for all the subjects A–C.

It will be recognized that the tubular member 19 may be secured to the tubular container as by a bridge.

Example 12

For the blood test container used in Example 11, an interior of its tubular container 2 was reduced in pressure so that blood can be vacuum collected therein. That is, for the attachment of the rubber stopper 5 to which the tubular container 19 was adhesively secured, as shown in FIG. 20, a vacuum capping machine (manufactured by Kyowa Shinku, Co., Ltd., product name: VS-150A) was utilized which placed the rubber stopper 5 on the container at 0.26 atmospheric pressure to permit vacuum collection of 7 ml blood.

Figure 22:
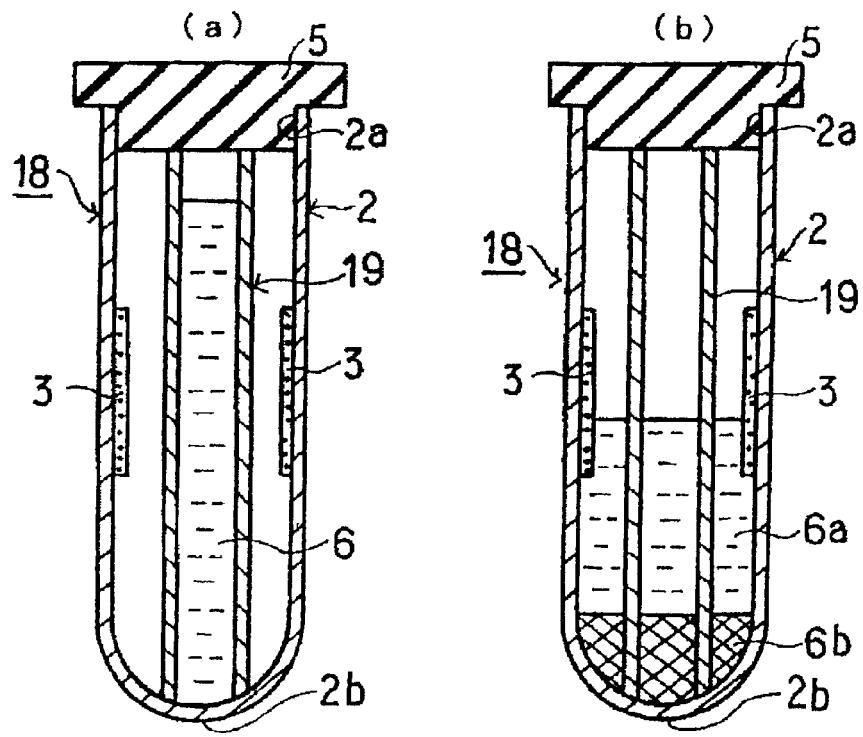
FIGS. 22(a) and 22(b) are transverse sectional views which explain blood test procedures when the blood test container shown in FIG. 20 is used, respectively.

Next, the blood test container was used to vacuum collect blood from each of the subjects, A–C, in the same manner as in Example 2. As a result, the blood 6 was introduced into the tubular member 19, as shown in FIG. 22(a). In this instance, no fraction of the blood 6 was found to leak from a bottom end of the tubular member 19 toward the interior of the tubular container 2. With the lapse of 10 minutes, each blood sample was centrifuged in the same manner as in Example 11. As a result, each blood sample, while separated into serum 6a and clot 6b, leaked from the tubular member 19 to the tubular container 2 side, as shown in FIG. 22(b). After centrifugation, each container was left to stand for 10 minutes to observe the reagents 3, resulting in proving HBs antigen negative and HBs antibody negative for all the blood samples from the subjects A–C.

Example 13

A blood test container 22 shown in FIG. 23 was assembled. The tubular container 2 was analogous to that used in Example 1. A 6 mm diameter and 60 mm long polyethylene tube, as a tubular member 23, was adhesively secured onto an inner wall surface of the tubular container 2 such that a top end of the polyethylene tube was located 10 mm below a top end of the tubular container 2. A 6 mm diameter polystyrene bead (manufactured by Sekisui Chemical Co., Ltd., product name: POLYSTYRENE BEAD #45) was secured by adhesive to a bottom of the tubular member 23.

The test reagent 3, identical in type to that used in Example 1, was secured within the polystyrene tube in the same manner as in Example 1. The elevation of the reagent 3 was adjusted such that its bottom end is located 8 cm above the bottom end of the tubular container 2.

Next, a blood sample from each of the subjects, A–C, was collected in the tubular container 2, as analogously to Example 1, while avoiding its entry into the tubular member 23. After left to stand for 10 minutes, each blood sample was centrifuged in the same manner as in Example 1. The centrifuging was found to cause the polystyrene bead, as a solid member 24, to fall and the blood to separate into serum and clot. Also, the serum was found to enter the tubular member 23.

After centrifugation, each container was left to stand for 10 minutes. The observation of the reagent 3 resulted in proving HBs antigen negative for all the blood samples from the subjects A–C.

Example 14

A blood test container 22 shown in FIG. 24 was assembled. Specifically, the configuration of the blood test container 22 shown in FIG. 23 was followed, except that the tubular container 2 fixedly accommodated therein two tubular members 23 to which two types of reagents 3, 3, identical to those used in Example 4, were respectively secured, and that its interior was reduced in pressure. For pressure reduction, a vacuum capping machine (manufactured by Kyowa Shinku, Co., Ltd., product name: VS-150A) was utilized which placed the rubber stopper 5 on the container at 0.26 atmospheric pressure to permit vacuum collection of 7 ml blood.

A blood sample was collected from each of the subjects, A–C, by using the blood test container thus prepared and evaluated in the same manner as in Example 13. The results proved HBs antigen negative and HBs antibody negative for all the blood samples from the subjects A–C.

Example 15

A blood test container 31 shown in FIG. 25 was assembled. The serum separating medium-containing vacuum blood-collecting tube used in Example 1 was used for the tubular container 2.

A rubber stopper was removed from this tubular container 2 to bring its interior to a normal pressure. Also, a 6 mm diameter and 60 mm long polypropylene tube (having an inner wall coated with a blood coagulation promoter) was used for a tubular member 14. A rubber was removed from a top end of a piston incorporated in a 5 ml syringe, manufactured by Nipro Co., Ltd., and centrally apertured by a cutter to provide an angular member 15 having a centrally-located, 6 mm diameter through-hole.

The angular member was immersed in diicosane, the temperature of which was controlled at 50° C. Then, the angular member was taken out from the diicosane, and the angular member was fixed to the outer surface of the tubular member 14 and inserted in the tubular container 2, so that the angular member 15 was secured through diicosane to the outer face of the tubular member 14 and the inner face of the tubular container 2.

Then, the HBs antigen detection reagent 3 was secured onto an inner wall surface of the tubular container 2 in the same manner as in Example 4.

Thereafter, the rubber stopper was adhesively secured onto a top end of the tubular member 14 and then pressed to fit in the tubular container 2. This results in obtaining the blood test container 31.

By using the blood test container 31 such assembled, a blood sample was collected from each of the subjects, A–C, in the same manner as in Example 1. After left to stand for 10 minutes, each blood sample was centrifuged at 3000 r.p.m. for 10 minutes by a centrifuge. As a result, the sample blood separated into serum 6a and solid matter 6b. Each container was placed in the 50° C. bath for 10 minutes. The subsequent dissolution of diicosane allowed the serum 6a to push the annular member 15 upward and finally contact the test reagent 3. The observation of the reagent 3 revealed HBs antigen negative and HBs antibody negative for all the the subjects A–C.

Example 16

A blood test container 31 shown in FIG. 26 was assembled in such a configuration as to permit vacuum collection of blood. Specifically, in the assembly of the blood test container 31 in Example 15, the attachment of the stopper 5 was accomplished by a vacuum capping machine (manufactured by Kyowa Shinku, Co., Ltd., product name: VS-150A) which placed the rubber stopper on the container at 0.26 atmospheric pressure to permit vacuum collection of 7 ml blood.

By using the blood test container 31 such assembled, a blood sample was collected from each of the subjects, A–C. After left to stand for 10 minutes, each blood sample was centrifuged in the same manner as in Example 15 and then maintained at 50° C. for 10 minutes.

Due conceivably to the dissolution of diicosane, the serum 6a pushed the annular member 15 upward and finally contacted the test reagent 3 in the same fashion as in Example 15. The observation of the reagent 3 resulted in proving HBs antigen negative and HBs antibody negative for all the blood samples from the subjects A–C.

Example 17

A blood test container 41 shown in FIG. 29 was assembled in the following manner. The tubular container 2, identical in configuration to that of Example 1, was used. As analogous to Example 1, QUICK CHASER HBsAg (manufactured by Mizuho Meddy Co., Ltd., about 6 cm long reagent for HBs antigen detection) was used for the test reagent 3. This test reagent was secured onto an inner wall of the tubular container 2 by a pressure-sensitive adhesive tape such that its top end is located 8 cm above a bottom 2b of the tubular container.

A polyethylene terephthalate test tube (manufactured by Sekisui Chemical Co., Ltd., 12 mm in diameter and 95 mm in length, having an inner wall coated with a blood coagulation promoter) was used for a second tubular container 42.

The second tubular container 42 was inserted in the tubular container 2 with the test reagent 3 secured thereon, which was subsequently closed by a stopper 5 formed of butyl bromide rubber.

The stopper 5 was removed, a blood sample from each of the subjects, A–C, was collected by an injector, and 1 ml of each blood sample collected was injected into the second tubular container 42 for the blood test container 41 of the present Example.

After injection, the stopper 5 was again attached to the blood test container. The blood test container was turned upside down and left to stand for 30 minutes during which period the blood sample was contacted with the test reagent 3. The observation of the test reagent 3 resulted in proving HBs antigen negative for all the subjects A–C.

Example 18

A blood test container was assembled in the same manner as in Example 17, with the exception that the test reagent 3 was secured to an outer face of the second tubular container 42 such that its top end was located 7 cm above the bottom of the second tubular container 42, but not secured to the inner face of the tubular container 2.

For the blood test container such assembled, the second tubular container 42 carrying the test reagent on its outer surface was inserted into the outer tubular container 2. The stopper used in Example 17 was then placed on the outer tubular container at 0.9 atmospheric pressure by a vacuum capping machine (manufactured by Kyowa Shinku, Co., Ltd., product name: VS-150A), which made it possible for the container to vacuum collect 1 ml blood.

A blood sample from each of the subjects, A–C, was brought in the second tubular container 42 according to a conventional vacuum blood collection procedure. After left to stand for 10 minutes, each blood sample was centrifuged at 3,000 r.p.m. for 10 minutes by using a centrifuge (product of a domestic manufacturer, product name: H-20) Thereafter, the blood test container was turned upside down to introduce the separated serum into a space defined between the inwardly-located second tubular container and the outer tubular container. This reversed orientation was maintained for 30 minutes during which time the test reagent was contacted with the serum. The observation of the test reagent resulted in proving HBs antigen negative for all the subjects A–C.

Example 19

The following procedure was used to assemble a blood test container which was identical in construction to the blood test container 43 shown in FIG. 30, with the exception that the test reagent 3 was fixedly positioned on the outer face of the second tubular container 42. The tubular container 2 was identical in construction to that used in Example 1.

Used for the second tubular container 42 was a serum separating medium-containing vacuum blood-collecting tube (manufactured by Sekisui Chemical Co., Ltd., product name: INSEPACK, a 12 mm diameter and 75 mm long polyethylene terephthalate tube having an inner wall coated with a blood coagulation promoter).

The HBs antigen detection reagent used in Example 1, as the test reagent 3, was adhesively secured onto the outer face of the second tubular container 42 such that its top end was located 7 cm above the bottom of the second tubular container 42.

The second tubular container 42 with the test reagent 3 adhesively secured on its outer face was inserted in the tubular container 2. A 5 mm wide and 20 mm long water-soluble film (pullulan), as the water-soluble material, was then secured around an outer periphery of the second tubular container 42 adjacent its top opening by an instantaneous adhesive (manufactured by Toa Gosei Co., Ltd., product name: ALONE-ALFA), so that the space X between the second tubular container 42 and tubular container 2 was closed.

Further, the butyl bromide rubber stopper 5 was placed on the tubular container 2 at 0.9 atmospheric pressure by a vacuum capping machine (manufactured by Kyowa Shinku, Co., Ltd., product name: VS-150A), which made it possible for the container to vacuum collect 1 ml blood.

A blood sample from each of the subjects, A–C, was brought in the second tubular container 42 according to a conventional vacuum blood collection procedure. After left to stand for 10 minutes, each blood sample was centrifuged at 3,000 r.p.m. for 10 minutes by using a centrifuge (product of a domestic manufacturer, product name: H-20) Thereafter, the blood test container was turned upside down to introduce the separated serum into a space defined between the inwardly-located second tubular container and the outer tubular container. This reversed orientation was maintained for 30 minutes during which time the test reagent was contacted with the serum. The observation of the test reagent resulted in proving HBs antigen negative for all the subjects A–C.

Example 20

The procedure of Example 19 was followed, except that, instead of using the water-soluble film "pullulan", diicosane was coated around the outer periphery of the second tubular container 42 adjacent its top opening to close the space X defined between the second tubular container 42 and tubular container 2. As a result, a blood test container 43 was assembled.

Also, a stopper was placed on the above-obtained blood test container in the same manner as in Example 19, which made it possible for the container to vacuum collect 1 ml blood.

A blood sample from each of the subjects, A–C, was collected in the second tubular container 42 of the above-obtained blood test container according to a vacuum blood collection technique. After left to stand for 10 minutes, each blood sample was centrifuged in the same manner as in Example 19. Next, the blood test container 43 was turned upside down and then placed in a constant temperature bath (manufactured by Komatsu Electronics Co., Ltd., product name: CTE24-A) controlled at 50° C. to reside therein for 30 minutes. The observation of the test reagent 3 resulted in proving HBs antigen negative for all the subjects A–C.

Example 21

Figure 31:
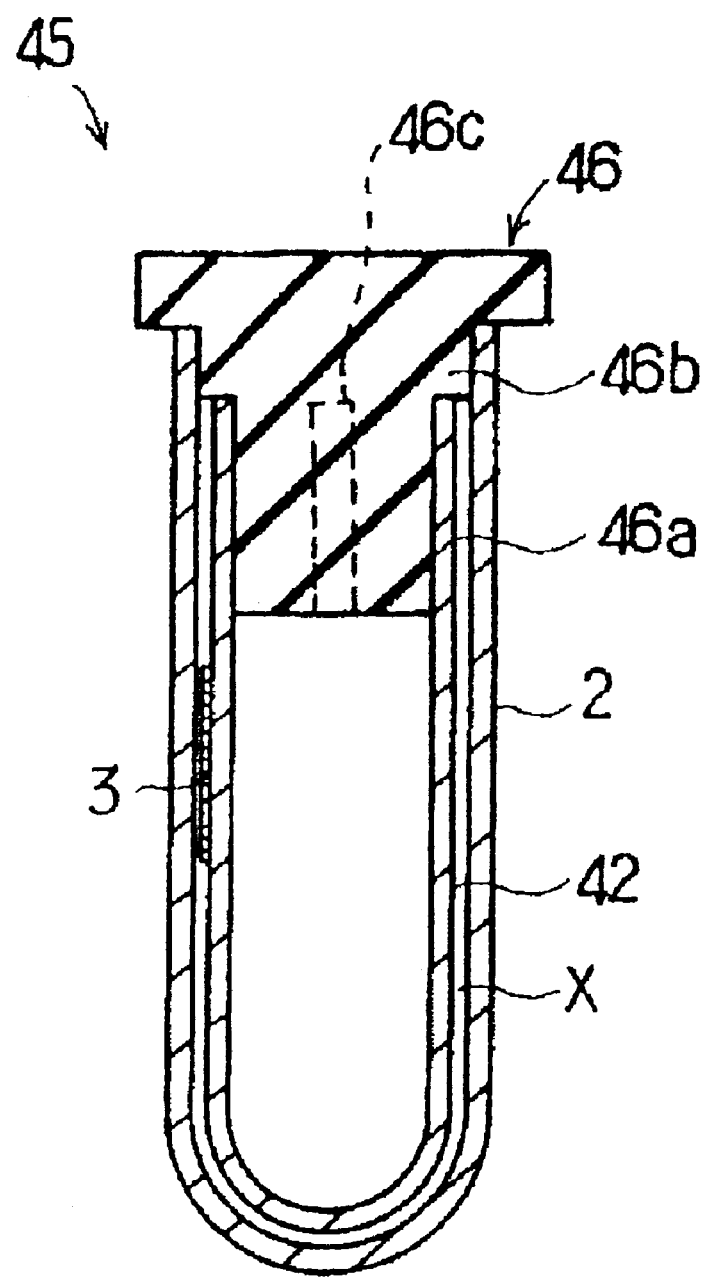
FIG. 31 is a transverse sectional view which explains the blood test container in accordance with the invention.

The following procedure was used to assemble the blood test container 45 shown in FIG. 31. The tubular container 2 was identical in construction to that used in Example 1.

Used for the tubular container 42 was a serum separating medium-containing vacuum blood-collecting tube (manufactured by Sekisui Chemical Co., Ltd., product name: INSEPACK, a 12 mm diameter and 75 mm long polyethylene terephthalate tube having an inner wall coated with a blood coagulation promoter). Also, a 2.5 mm wide, 5 mm long and 0.5 mm deep groove 42a was provided on the inner face of the second tubular container 42 to extend downwardly from its top opening.

Further provided was a butyl bromide rubber stopper 46 which had a vertically-extending 2.5 mm wide, 5 mm long and 0.5 mm deep groove 46c on its first stopper portion 46a.

The test reagent 3, identical to the HBs antigen detection reagent used in Example 1, was adhesively secured onto the outer face of the second tubular container 42 in the same manner as in Example 18.

The second tubular container 42 with the test reagent 3 adhesively secured thereon was inserted in the tubular container 2. The butyl bromide rubber stopper was then placed on the second tubular container, with its groove 46c displaced from longitudinal alignment with the groove 42a, at 0.9 atmospheric pressure by a vacuum capping machine (manufactured by Kyowa Shinku, Co., Ltd., product name: VS-150A), which made it possible for the container to vacuum collect 1 ml blood.

A blood sample from each of the subjects, A–C, was introduced into the second tubular container 42 according to a vacuum blood collection technique. After left to stand for 10 minutes, each blood sample was centrifuged at 3,000 r.p.m. for 10 minutes by using a centrifuge (product of a domestic manufacturer, product name: H-20). Then, the blood test container 45 was turned upside down and the stopper 46 was rotated to align the groove 46c with the groove 42a thereby providing a flow path. As a result, the separated serum was introduced into the space X between the second tubular container 42 and the tubular container 2. After left to stand for 30 minutes, the test reagent 3 was observed. The results proved HBs antigen negative for all the subjects A–C.

Example 22

The tubular container 2 and second tubular container 42 used in Example 20 were utilized. Also, the HBs antigen detection reagent, as the test reagent 3, was adhesively secured onto the outer face of the second tubular container 42 in the same manner as in Example 20.

Subsequently, the second tubular container 42 with the test reagent 3 adhesively secured thereon was inserted in the tubular container 2. 0.2 g of serum separating medium was removed from a separately-provided, serum separating medium-containing vacuum blood-collecting tube (manufactured by Sekisui Chemical Co., Ltd., product name: INSEPACK) and then coated around the outer periphery of the second tubular container 42 to close the space X between the second tubular container 42 and tubular container 2.

The butyl bromide rubber stopper 5 was utilized, as analogously to Example 20, to assemble the blood test container 43 in such a configuration as to permit vacuum collection of 1 ml blood. A blood sample from each of the subjects, A–C, was brought in the second tubular container 42 according to a conventional vacuum blood collection procedure. After left to stand for 10 minutes, each blood sample was centrifuged at 3,000 r.p.m. for 10 minutes by using a centrifuge (product of a domestic manufacturer, product name: H-20). Then, the blood test container was turned upside down to introduce the separated serum into a space between the inwardly-located second tubular container and the outer tubular container. This reversed orientation was maintained for 30 minutes during which time the test reagent 3 was contacted with the serum. The subsequent observation of the test reagent resulted in proving HBs antigen negative for all the subjects A–C.

Example 23

The tubular container 2 and second tubular container 42 used in Example 19 were utilized. Also, the HBs antigen detection reagent, as the test reagent 3, was adhesively secured onto the outer face of the second tubular container 42 in the same manner as in Example 19.

After its top opening was sealed by a polymer film 52 comprised of a parafilm, the second tubular container 42 was inserted in the tubular container 2.

Also, the butyl bromide rubber stopper 5 was placed on the tubular container by using a vacuum capping machine, as analogously to Example 19, which made it possible for the container to vacuum collect 1 ml blood. As a result, the blood test container 51 was assembled.

A blood sample from each of the subjects, A–C, was brought in the second tubular container 42 according to a conventional vacuum blood collection procedure. After left to stand for 10 minutes, each blood sample was centrifuged at 3,000 r.p.m. for 10 minutes by using a centrifuge (product of a domestic manufacturer, product name: H-20) Then, the blood test container was turned upside down to introduce the separated serum into a space between the inwardly-located second tubular container and the outer tubular container. This reversed orientation was maintained for 30 minutes during which time the test reagent 3 was contacted with the serum. The subsequent observation of the test reagent resulted in proving HBs antigen negative for all the subjects A–C.

Example 24

The procedure of Example 23 was followed, except that the parafilm used to constitute the polymer film 52 was replaced by a film-form diicosane, to assemble the blood test container 51 in such a configuration as to permit vacuum collection of 1 ml blood.

A blood sample from each of the subjects, A–C, was vacuum collected in the second tubular container 42 of the above-assembled blood test container. After left to stand for 10 minutes, each blood sample was centrifuged in the same manner as in Example 19. Subsequently, the blood test container 43 was turned upside down and placed in a constant temperature bath (manufactured by Komatsu Electronics Co., Ltd., product name: CTE24-A) controlled at 50° C. to reside therein for 30 minutes. The subsequent observation of the test reagent 3 resulted in proving HBs antigen negative for all the subjects A–C.

Example 25

Figure 37:
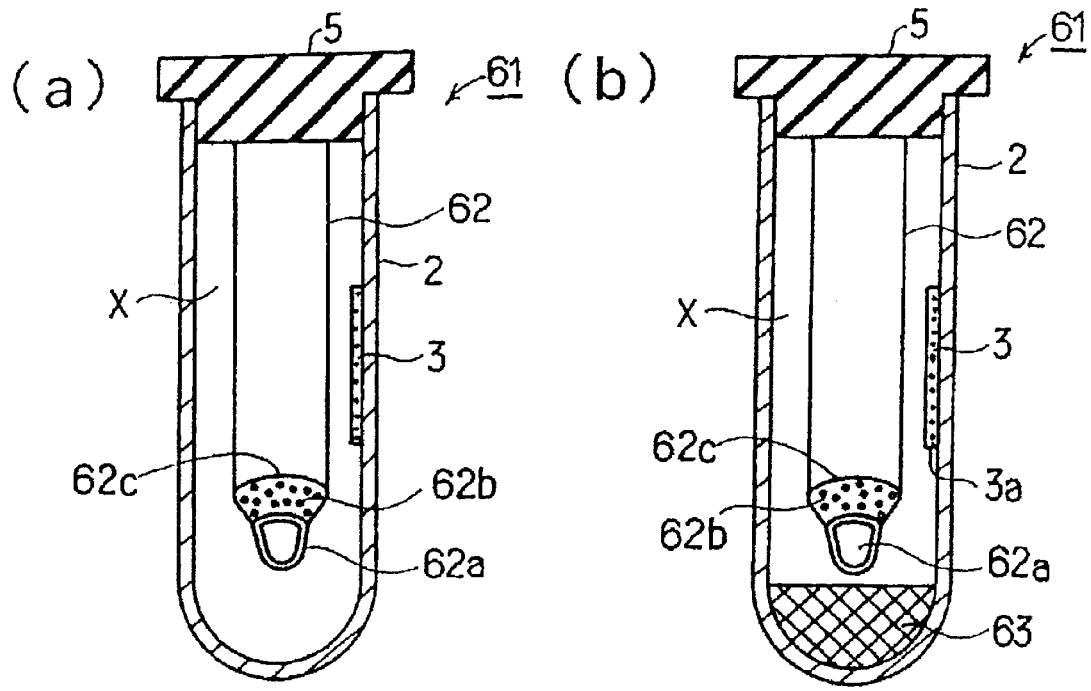
FIGS. 37(a) and 37(b) are transverse sectional views which explain the blood test container in accordance with the invention, respectively.

The following procedure was used to assemble the blood test container 61 shown in FIG. 37. The tubular container 2 used in Example 1 was utilized.

In fabricating the second tubular container 62, a SAN-PREP filter (manufactured by Millipore Co., Ltd., product number: MILLEX-LH, pore size of 0.5 $\mu$m) was attached to a top end of a 2.5 ml blood-collecting syringe (manufactured by Terumo Co., Ltd.), 0.4 g of polystyrene gel having a particle size of 8 $\mu$m (manufactured by Sekisui Chemical Co., Ltd., product name: MICRONEX) was introduced into the syringe from its upper portion (i.e., through an opening for insertion of a piston), and a 1.5 ml polypropylene sample cup (manufactured by Eppendorf Co., Ltd.) was embedded centrally of the aforementioned gel to constitute the trap portion 62a while constituting the blood cell separating layer 62b from the gel.

Next, the HBs antigen detection reagent used in Example 1, as the test reagent 3, was adhesively secured onto the inner face of the tubular container 2.

The second tubular container 62, as fabricated in the manner as described above, was secured to a bottom of the stopper 5 by using an instantaneous adhesive (manufactured by Toa Gosei Co., Ltd., product name: ALONE-ALFA) and then inserted in the tubular container 2, followed by placement of the stopper on the tubular container 2.

A blood sample from each of the subjects, A–C, was collected by an injector. 1 ml of each blood sample was transferred to the blood test container of the present Example and then centrifuged at 3,000 r.p.m. for 10 minutes by using a centrifuge (product of a domestic manufacturer, product name: H-20).

After centrifugation, the blood test container was left to stand for 10 minutes. The subsequent observation of the reagent secured on the container wall resulted in proving HBs antigen negative for every subject.

Example 26

The blood test container 61 was assembled in the same manner as in Example 25. However, the stopper 5 was placed on the second tubular container 62 at 0.85 atmospheric pressure by a vacuum capping machine (manufactured by Kyowa Shinku, Co., Ltd., product name: VS-150A), which made it possible for the container to vacuum collect 1 ml blood. A blood sample from each of the subjects, A, B and C, was collected in the blood test container of the present Example and then centrifuged at 3,000 r.p.m. for 10 minutes by using a centrifuge (product of a domestic manufacturer, product name: H-20). After centrifugation, each blood test container was left to stand for 10 minutes. The subsequent observation of the reagent on the container wall resulted in proving HBs antigen negative for all the three subjects.

Example 27

The following procedure was used to assemble the blood test container 71 shown in FIG. 39. The tubular container 2 used in Example 1 was utilized.

The rubber stopper was removed from the tubular container 2 to bring its interior to a normal pressure.

A 6 mm diameter and 60 mm long polypropylene tube (having an inner wall coated with a blood coagulation promoter) was used for the second tubular container 72.

A filter, manufactured by Millipore Co., Ltd. (product number: MILLEX-SV, pore size of 5 $\mu$m), was cut to a diameter of 10 mm and then secured to a bottom opening of the second tubular container 72 by using a pressure-sensitive adhesive tape. In this manner, a bottom member 72b comprised of the aforementioned filter was secured to the bottom end of the second tubular container 72.

0.2 g of polystyrene gel having a particle size of 8 $\mu$m (manufactured by Sekisui Chemical Co., Ltd., product name: MICRONEX) was then charged into the second tubular container 72 to form therein the hydrophilic fine particle layer 73.

Thereafter, the HBs antigen detection reagent, as the test reagent 3, was adhesively secured onto the inner face of the tubular container 2 in the same manner as in Example 1.

The second tubular container 72 was secured to a bottom of the stopper 5 by an instantaneous adhesive (manufactured by Toa Gosei Co., Ltd., product name: ALONE-ALFA) and then inserted inserted in the tubular container 2, followed by placement of the stopper on the tubular container 2. A blood sample from each of the subjects, A, B and C, was brought in the second tubular container 72 according to a conventional vacuum blood collection procedure. After left to stand for 10 minutes, each blood sample was centrifuged at 3,000 r.p.m. for 10 minutes by a centrifuge (product of a domestic manufacturer, product name: H-20). Then, the blood test container was turned upside down to introduce the separated serum into a space between the inwardly-located second tubular container and the outer tubular container. This reversed orientation was maintained for 30 minutes during which time the test reagent 3 was contacted with the serum. The subsequent observation of the test reagent 3 resulted in proving HBs antigen negative for the subjects A, B and C.

EXAMPLE 28

The procedure of Example 27 was followed, except that the stopper 5 was placed on the tubular container at 0.85 atmospheric pressure by using a vacuum capping machine (manufactured by Kyowa Shinku, Co., Ltd., product name: VS-150A), to assemble the blood test container 71 (shown in FIG. 39) capable of vacuum collecting 1 ml blood.

By using the blood test container thus assembled, a blood sample from each of the subjects, A, B and C, was collected and evaluated in the same manner as in Example 27. The results proved HBs antigen negative and HBs antibody negative for all the blood samples from the subjects A–C.

Example 29

Whole blood was used for each specimen in this Example.

The blood test container 4 shown in FIG. 4 was assembled. A blood coagulation inhibitor-containing vacuum blood-collecting tube (manufactured by Sekisui Chemical Co., Ltd., product name: INSEPACK, a 15 mm diameter and 100 mm long polyethylene terephthalate tube having an inner wall uncoated with a blood coagulation promoter) was provided. A rubber stopper was removed from this vacuum blood-collecting tube to bring its interior to a normal pressure, thereby obtaining the tubular container 2.

Next, a single-dosage QUICK CHASER HBsAg (manufactured by Mizuho Meddy Co., Ltd., about 6 cm long reagent for HBs antigen detection), as the test reagent 3, was adhesively secured onto the tubular container by a pressure-sensitive adhesive tape such that its top end was located 8 cm above the bottom 2b of the tubular container.

Subsequently, the stopper 5 was placed on the tubular container at 0.26 atmospheric pressure by using a vacuum capping machine (manufactured by Kyowa Shinku, Co., Ltd., product name-: VS-150A) to assemble the blood test container 4 with the stopper 5, as shown in FIG. 4, in such a configuration as to permit vacuum collection of 7 ml blood.

By using the blood test container thus assembled, a blood sample from each of the subjects, A–C, was collected and left at rest for 10 minutes. The subsequent observation of the test reagent 3 resulted in proving HBs antigen negative for all the blood samples from the subjects A–C.

Example 30

Figure 40:
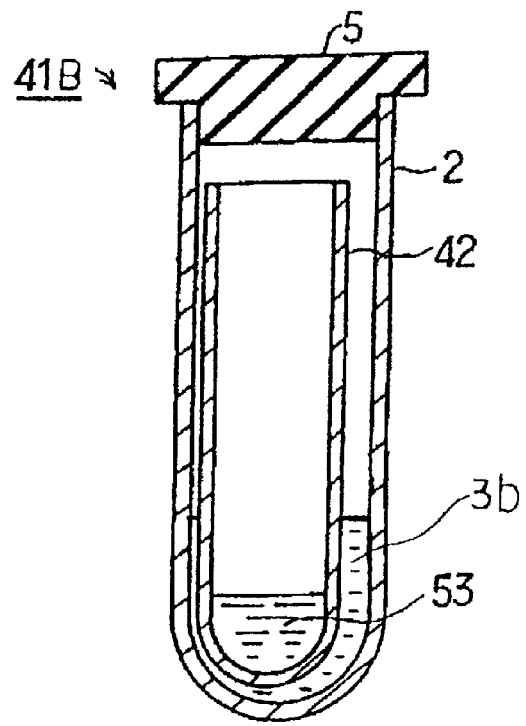
FIG. 40 is a transverse sectional view, showing the blood test container of Example 30.

The following procedure was used to assemble the blood test container 41B shown in FIG. 40. The tubular container 2 used in Example 1 (but uncoated on its inner wall surface with a blood coagulation promoter) was utilized. 1 ml of 0.04 wt. % solution of Bromothymol Blue indicator (manufactured by Wako Pure Pharm. Co., Ltd.), as the test reagent 3b, was charged in the tubular container.

A rubber stopper was removed from a plasma separating medium-containing vacuum blood-collecting tube (manufactured by Sekisui Chemical Co., Ltd., a 12 mm diameter and 95 mm long tube having an inner wall uncoated with a blood coagulation promoter) to bring its interior to a normal pressure, thereby providing the second tubular container 42. This second tubular container 42 was then inserted in the tubular container 2 accommodating therein the aforementioned test reagent 3b, followed by placement of the butyl bromide rubber stopper 5 on the outer tubular container 2 at 0.26 atmospheric pressure by using a vacuum capping machine (manufactured by Kyowa Shinku, Co., Ltd., product name: VS-150A). As a result, the blood test container 41B with the stopper 5, as shown in FIG. 40, was assembled in such a configuration as to permit vacuum collection of 7 ml blood.

A blood sample from each of the subjects, A, B and C, was brought in the second tubular container 42 according to a conventional vacuum blood collection procedure. Each blood sample was then centrifuged at 3,000 r.p.m. for 10 minutes by a centrifuge (product of a domestic manufacturer, product name: H-20). Then, the blood test container was turned upside down to introduce the separated plasma into a space between the inwardly-located second tubular container and the outer tubular container. This reversed orientation was maintained for 30 minutes during which time the test reagent 3b was contacted with the plasma. The test reagent was subsequently observed. The Bromothymol Blue indicator solution was found as having turned in color to green, i.e., having been neutralized, for the subjects A, B and C.

Example 31

Figure 41:
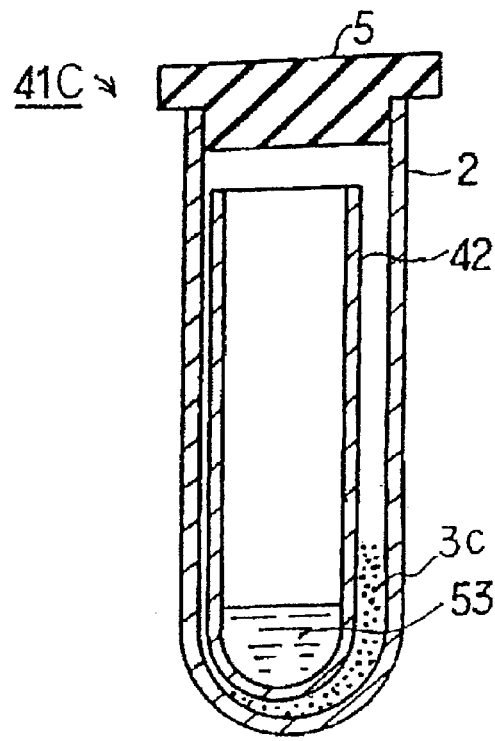
FIG. 41 is a transverse sectional view, showing the blood test container of Example 31.

The following procedure was used to assemble the blood test container 41C shown in FIG. 41. The tubular container 2 used in Example 1 (but uncoated on its inner wall surface with a blood coagulation promoter) was utilized. 1 mg of powder-form Bromothymol Blue indicator (manufactured by Wako Pure Pharm. Co., Ltd.), as the test reagent 3c, was introduced into the tubular container.

A rubber stopper was removed from a plasma separating medium-containing vacuum blood-collecting tube (manufactured by Sekisui Chemical Co., Ltd., a 12 mm diameter and 95 mm long tube having an inner wall uncoated with a blood coagulation promoter) to bring its interior to a normal pressure, thereby providing the second tubular container 42. This second tubular container 42 was then inserted in the tubular container 2 accommodating therein the aforementioned test reagent 3c, followed by placement of the butyl bromide rubber stopper 5 on the outer tubular container 2 at 0.26 atmospheric pressure by using a vacuum capping machine (manufactured by Kyowa Shinku, Co., Ltd., product name: VS-150A). As a result, the blood test container 41C with the stopper 5, as shown in FIG. 40, was assembled in such a configuration as to permit vacuum collection of 7 ml blood.

A blood sample from each of the subjects, A, B and C, was brought in the second tubular container 42 according to a conventional vacuum blood collection procedure. Each blood sample was then centrifuged at 3,000 r.p.m. for 10 minutes by a centrifuge (product of a domestic manufacturer, product name: H-20). Then, the blood test container was turned upside down to introduce the separated plasma into a space between the inwardly-located second tubular container and the outer tubular container. This reversed orientation was maintained for 30 minutes during which time the test reagent was contacted with the plasma. The test reagent was subsequently observed. The Bromothymol Blue indicator was found as having turned in color to green, i.e., having been neutralized, for the subjects A, B and C.

Example 32

Figure 52:
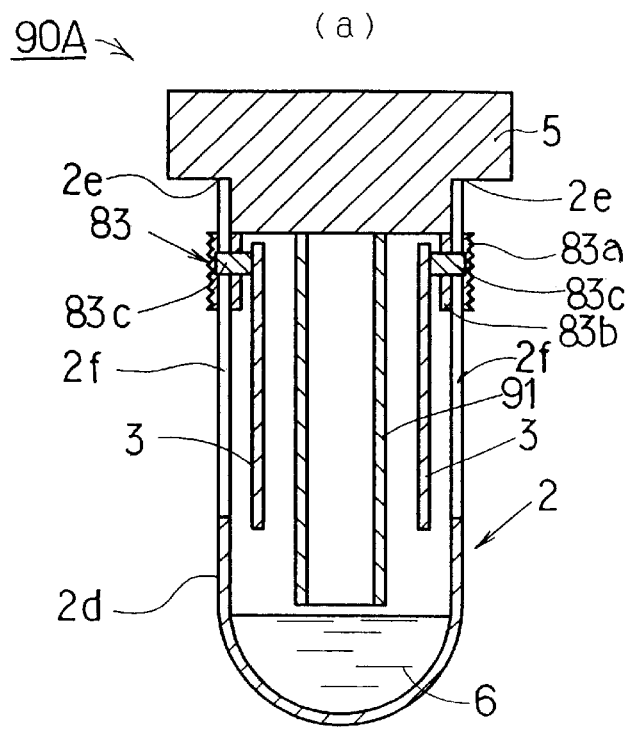
FIGS 52(a) and 52(b) are a transverse view showing the blood test container of Example 32.
Figure 52:
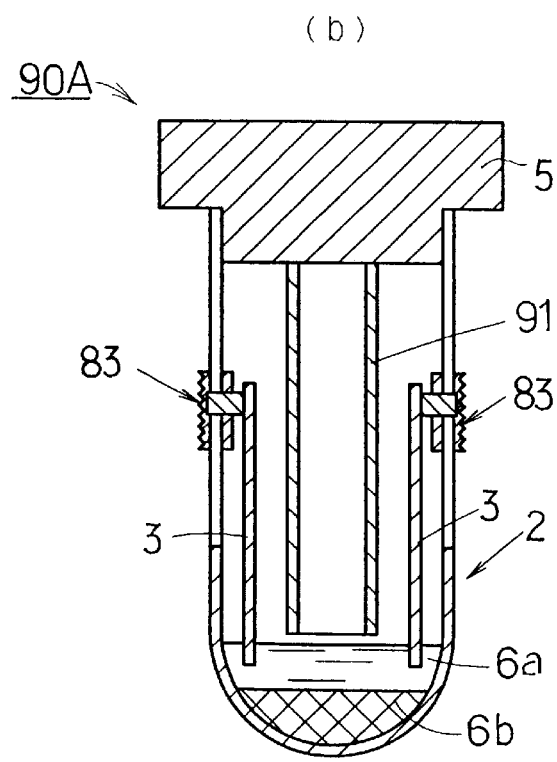

The blood test container 90A shown in FIG. 52(a) was assembled. The blood test container 90A was identical in construction to the blood test container 90 shown in FIG. 46, excepting the below-described difference.

Difference: For the blood test container 90, the tube 91 was adhesively secured onto the bottom surface of the lid member 92. On the other hand, for the blood test container 90A, the tube 91 was adhesively secured to the rubber stopper 5 for attachment to the tubular container 2.

First, a rubber stopper was removed from a plasma separating medium-containing vacuum blood-collecting tube (manufactured by Sekisui Chemical Co., Ltd., product name: INSEPACK, a 10 mm diameter and 75 mm long polyethylene terephthalate tube) to bring its interior to a normal pressure, thereby providing the tubular container 2.

A pair of opposing rectangularly-shaped slots 2f, 2f, each having a width of 3 mm and a length of 30 mm, were provided which extend downwardly from a open top edge along a side wall of the tubular container 2. The sliding switch 83 (made from polyethylene and having 5 mm wide and 10 mm long outer wing 83a and inner wing 83b) was attached to each slot 2f such that its outer wing 83a and inner wing 83b flanked therebetween the opposing side walls 2g, 2h (refer to FIG. 43) of the slot 2f therebetween.

A single-dosage QUICK CHASER HBsAg (manufactured by Mizuho Meddy Co., Ltd., 5 mm wide and 40 mm long reagent for HBs antigen detection), as the test reagent 3, had been previously suspended from a top end of the joining member 83c of the sliding switch 83, with the aid of a pressure-sensitive adhesive tape, such that when the sliding switch 83 was shifted to the highest position, a top edge of the test reagent 3 was located 60 mm above the bottom of the tubular container 2.

The aforementioned HBs antigen detection reagent (QUICK CHASER HBsAg) is an immunochromatography assay reagent based in principle on a sandwich technique. When a blood sample is contacted with a lower portion of the reagent, the blood sample is caused to migrate on the reagent according to a capillary phenomenon. The HBs antigen present in the blood sample then reacts with the anti-HBs mouse monoclonal antibody binding colloidal gold, as previously coated on the reagent, to form an HBs antigen-antibody-colloidal gold complex. This complex further migrates on a membrane filter to reach the anti-HBs mouse monoclonal antibody solid phase portion where it is bound trapped. As a result, in the case of HBs antigen positive, a red purple line derived from the colloidal gold is caused to appear in the solid phase portion, but not in the case of HBs antigen negative. Whether HBs antigen positive or negative can thus be visually determined.

The 6 mm diameter and 60 mm long polypropylene tube 91 was at its top end secured to a bottom of the stopper 5 (i.e., a rubber stopper used in the vacuum blood-collecting tube, INSEPACK), sized to fit in the above-described tubular container 2, by an adhesive (manufactured by Toa Gosei Co., Ltd., product name: Alone-alfa). The stopper 5 carrying the tube 91 adhesively secured thereto was then fittingly placed at the top opening of the tubular container 2 to which the sliding switches 83 were attached. As a result, the blood test container 90A was assembled.

A blood sample was collected from each of the subjects, A, B and C, by an injector, and its blood-collecting needle was thrust through the stopper 5 of the above-obtained blood test container to introduce 1 ml of each blood sample into the blood test container (refer to FIG. 52(a)). Each blood sample was centrifuged at 3,000 r.p.m. for 10 minutes by using a centrifuge (product of a domestic manufacturer, product name-: H-20), and as a result, separated into plasma 6A and hemocyte 6B.

After centrifugation, the sliding switch 83 was pushed down to bring a part of the test reagent 3 into contact with the plasma 6A (refer to FIG. 52(b)). After left to stand for 10 minutes, the test reagent 3 was observed. The results proved HBs antigen negative for all the subjects, A, B and C.

Example 33

Figure 51:
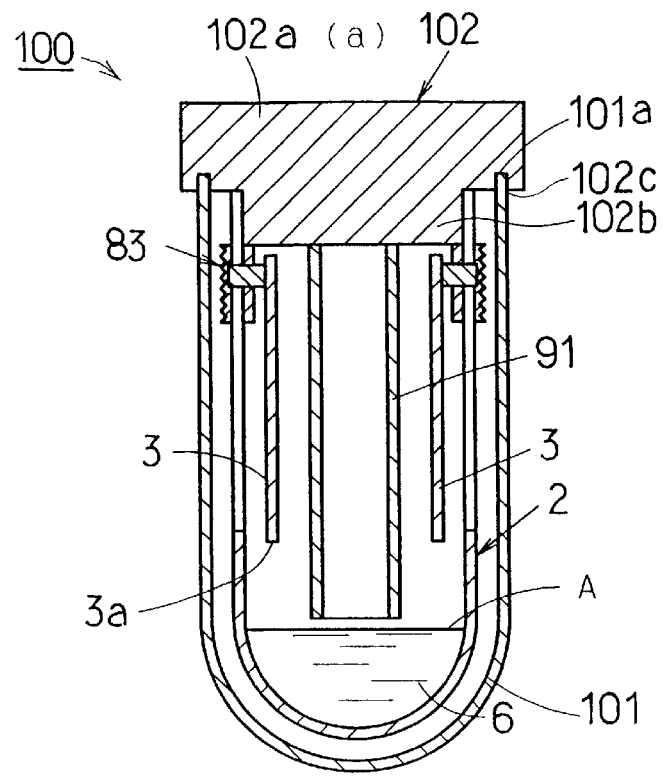
FIGS. 51(a) and 51(b) are a transverse view showing the blood test container of Example 33.
Figure 51:
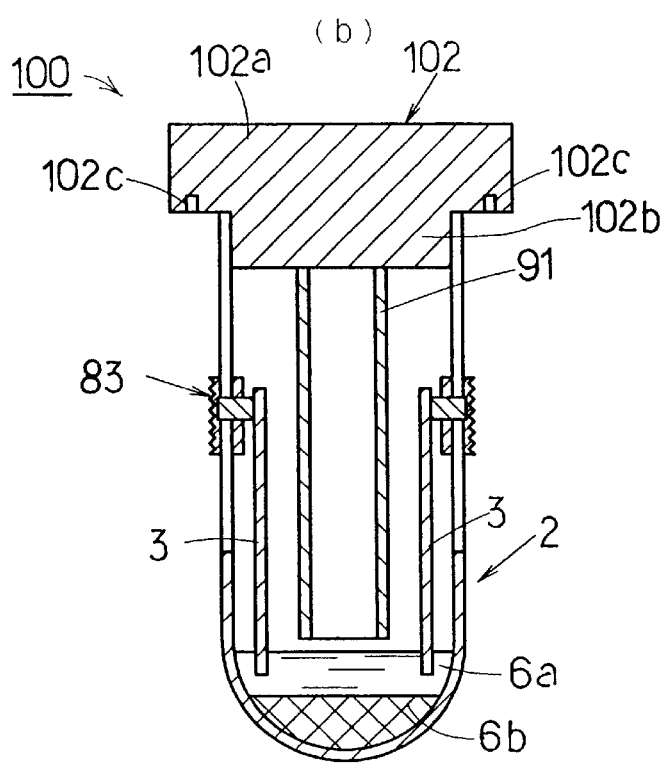

The blood test container 100 shown in FIG. 51 was assembled. Specifically, a rubber stopper was removed from a vacuum blood-collecting tube identical in construction to that used in Example 32 to provide the tubular container 2. A pair of sliding switches 83 each carrying the test reagent 3 were attached to the tubular container 2 in the same manner as in Example 32. The test reagent 3 secured to the sliding switch 83 on one slot 2f was identical in type to the test reagent 3 (QUICK CHASER HBsAg) used in Example 32. However, the test reagent 3 secured to the sliding switch 83 on the other slot 2f was the HBs antibody detection reagent (manufactured by Dynabbot Co., Ltd., product name: DYNASCREEN O-SUB), instead of QUICK CHASER HBsAg.

A top end of the tube 91 identical in construction to that used in Example 32was adhesively secured onto a bottom surface of the stopper 102 sized to fit in the top opening of the tubular container 2 and having the groove 102c. The stopper 102 carrying the tube 91 adhesively secured thereon was then fitted in the top opening of the tubular container 2 bearing the pair of sliding switches 83.

Next, a 13 mm diameter and 100 mm long, closed-bottom tubular container 101, formed of polyethylene terephthalate, was put lightly to cover the tubular container 2, followed by pressing the open top edge of the tubular container 101 into the groove 102c of the stopper 102 at 0.85 atmospheric pressure by using a vacuum capping machine (manufactured by Kyowa Shinku, Co., Ltd., product name: VS-150A). As a result, the shown blood test container was assembled in such a configuration as to permit vacuum collection of 1 ml blood.

The blood test container such assembled was set at a holder for vacuum blood collection, to which a multiple blood-collecting needle had been attached. This multiple blood-collecting needle was at its one end stuck into a blood vessel of a human subject and at its another end thrust through the stopper 102. According to such a conventional vacuum blood collection procedure, 1 ml of a blood sample was collected from each of the human subjects, A, B and C. Each blood sample was centrifuged at 3,000 r.p.m. for 10 minutes by using a centrifuge (product of a domestic manufacturer, product name: H-20), and as a result, separated into plasma 6A and hemocyte 6B.

After centrifugation, the outer tubular container was removed and then the sliding switch 83 was pushed down to bring a part of the test reagent 3 into contact with the plasma 6A (refer to FIG. 51(b)). After left to stand for 10 minutes, the test reagent 3 was observed. The results proved HBs antigen negative and HBs antibody negative for all the subjects, A, B and C.

Example 34

The blood test container 111 shown in FIG. 53 was assembled. A 15.5 mm diameter and 100 mm long, polyethylene terephthalate tubular container 2 (manufactured by Sekisui Chemical Co., Ltd., product name: SEPARAPIT TUBE) and a 6 mm diameter and 85 mm long, polyethylene terephthalate second tubular container 112 (manufactured by Sekisui Chemical Co., Ltd., product name: SEPARAPIT TUBE) were provided. An interior of each of the tubular container 2 and second tubular container 112 was washed with purified water.

Next, a bottom of the second tubular container 112 was apertured to provide a 3 mm diameter hole 112a.

QUICK CHASER HBsAg ((manufactured by Mizuho Meddy Co., Ltd., 6 cm long reagent for HBs antigen detection), as the test reagent 3, was secured onto an outer wall of the second tubular container by a pressure-sensitive adhesive tape. In this instance, the blood test reagent 3 was secured such that its top edge was located 1 cm above the bottom opening of the second tubular container.

5 mg of EDTA, as the anti-coagulant, was introduced into the second tubular container 112.

The second tubular container 112 was then inserted in the tubular container 2 which was subsequently closed by the stopper 5.

A blood sample from each of the subjects, A, B and C, was collected by an injector. 2 ml of each blood sample collected was injected into the blood test container of the present Example which was subsequently left to stand for 40 minutes. The following observation of the blood test reagent 3 resulted in proving HBs antigen negative for all the blood samples from the subjects, A, B and C.

Example 35

The blood test container 111 shown in FIG. 53 was assembled. A 15.5 mm diameter and 100 mm long, polyethylene terephthalate tubular container 2 (manufactured by Sekisui Chemical Co., Ltd., product name: SEPARAPIT TUBE) and a 6 mm diameter and 85 mm long, polyethylene terephthalate second tubular container 112 (manufactured by Sekisui Chemical Co., Ltd., product name: SEPARAPIT TUBE) were provided. An interior of each of the tubular container 2 and second tubular container 112 was washed with purified water.

Next, a bottom of the second tubular container 112 was apertured to provide a 3 mm diameter hole 112a.

QUICK CHASER HBsAg ((manufactured by Mizuho Meddy Co., Ltd., 6 cm long reagent for HBs antigen detection), as the blood test reagent, was secured onto an outer wall of the second tubular container 112 by using a pressure-sensitive adhesive tape. In this instance, the blood test reagent 3 was secured such that its top edge was located 1 cm above the bottom opening of the second tubular container 112.

2 mg of EDTA, as the anti-coagulant, was introduced into the second tubular container 112.

The second tubular container 112 such treated was then inserted in the tubular container 2, followed by placement of the stopper 5 on the outer tubular container at 0.56 atmospheric pressure by using a vacuum capping machine (manufactured by Kyowa Shinku, Co., Ltd., product name: VS-150A). As a result, the blood test container of the present Example was assembled in such a configuration as to permit vacuum collection of 2 ml blood.

The blood test container such assembled was used to vacuum collect a blood sample from each of the subjects, A, B and C. Each blood test container was then left to stand for 40 minutes. The subsequent observation of the blood test reagent 3 resulted in proving HBs antigen negative for all the blood samples from the subjects, A, B and C.

Example 36

The blood test container 121 shown in FIG. 54 was assembled. A 15.5 mm diameter and 100 mm long, polyethylene terephthalate tubular container 2 (manufactured by Sekisui Chemical Co., Ltd., product name: SEPARAPIT TUBE) and a 6 mm diameter and 85 mm long, polyethylene terephthalate second tubular container 112 (manufactured by Sekisui Chemical Co., Ltd., product name: SEPARAPIT TUBE) were provided. An interior of each of the tubular container 2 and second tubular container 112 was washed with purified water.

Next, a bottom of the second tubular container 112 was apertured to provide a 3 mm diameter hole 112a. A water-soluble cover member comprised of a 6 mm diameter disc-form water-soluble film (pullulan) was secured by instantaneous adhesive (manufactured by Toa Gosei Co., Ltd., product name: ALONE-ALFA) to cover and close the hole 112a.

QUICK CHASER HBsAg ((manufactured by Mizuho Meddy Co., Ltd., 6 cm long reagent for HBs antigen detection), as the blood test reagent 3, was secured onto an outer wall of the second tubular container 112 by using a pressure-sensitive adhesive tape. In this instance, the blood test reagent 3 was secured such that its top edge was located 1 cm above the bottom opening of the second tubular container 112.

5 mg of EDTA, as the anti-coagulant, was introduced into the second tubular container 112.

Next, the second tubular container 112 was inserted in the tubular container 2 which was subsequently closed by the stopper 5.

A blood sample from each of the subjects, A, B and C, was collected by an injector. 2 ml of each blood sample collected was injected into the blood test container of the present Example which was subsequently left to stand for 40 minutes. The following observation of the blood test reagent 3 resulted in proving HBs antigen negative for all the blood samples from the subjects, A, B and C.

Example 37

The blood test container 121 shown in FIG. 54 was assembled. A 15.5 mm diameter and 100 mm long, polyethylene terephthalate tubular container 2 (manufactured by Sekisui Chemical Co., Ltd., product name: SEPARAPIT TUBE) and a 6 mm diameter and 85 mm long, polyethylene terephthalate second tubular container 112 (manufactured by Sekisui Chemical Co., Ltd., product name: SEPARAPIT TUBE) were provided. An interior of each of the tubular container 2 and second tubular container 112 was washed with purified water.

Next, a bottom of the second tubular container 112 was apertured to provide a 3 mm diameter hole 112a. A water-soluble cover member comprised of a 6 mm diameter disc-form water-soluble film (pullulan) was secured by instantaneous adhesive (manufactured by Toa Gosei Co., Ltd., product name: ALONE-ALFA) to cover and close the hole 112a.

QUICK CHASER HBsAg ((manufactured by Mizuho Meddy Co., Ltd., 6 cm long reagent for HBs antigen detection), as the blood test reagent 3, was secured onto an outer wall of the second tubular container 112 by using a pressure-sensitive adhesive tape. In this instance, the blood test reagent 3 was secured such that its top edge was located 1 cm above the bottom opening of the second tubular container 112.

2 mg of EDTA, as the anti-coagulant, was introduced into the second tubular container 112.

The second tubular container 112 such treated was then inserted in the tubular container 2, followed by placement of the stopper 5 on the outer tubular container at 0.56 atmospheric pressure by using a vacuum capping machine VS-150A (manufactured by Kyowa Shinku, Co., Ltd.). As a result, the blood test container of the present Example was assembled in such a configuration as to permit vacuum collection of 2 ml blood.

The blood test container such assembled was used to vacuum collect a blood sample from each of the subjects, A, B and C. Each blood test container was then left to stand for 40 minutes. The subsequent observation of the blood test reagent 3 resulted in proving HBs antigen negative for all the blood samples from the subjects, A, B and C.

Example 38

The procedure of Example 36 was followed, except that the cover member 122 comprised of a 4 mm diameter stainless steel plate was brought into contact with the inner face of the hole 112a to close the hole 112a, to assemble the blood test container.

2 mg of EDTA, as the anti-coagulant, was introduced into the second tubular container 112, and then a blood sample was collected from each of the subjects, A, B and C, in the same manner as in Example 36.

The stainless steel cover member 122 was then caused to shift by moving a magnet outside the blood test container to open the hole 112a, which allowed each blood sample to flow into the space defined between the tubular container 2 and the second tubular container 112 and contact the blood test reagent 3.

Each blood test container was left to stand for 40 minutes and then its blood test reagent 3 was observed. The results proved HBs antigen negative for all the blood samples from the subjects, A, B and C.

Example 39

The blood test container 121 shown in FIG. 54 was assembled in the same manner as in Example 38. However, after insertion of the second tubular container 112 in the tubular container 2, the stopper 5 was placed on the outer tubular container at 0.56 atmospheric pressure by using a vacuum capping machine VS-150A (manufactured by Kyowa Shinku, Co., Ltd.). As a result, the blood test container was assembled in such a configuration as to permit vacuum collection of 2 ml blood.

Thereafter, the cover member 122 was caused to shift by moving the external magnet, which allowed each blood sample to flow from an interior of the second tubular container 112 into the space between the tubular container 2 and second tubular container 112, where it was contacted with the blood test reagent 3.

Example 40

The blood test container 131 shown in FIG. 55 was assembled. A 15.5 mm diameter and 100 mm long, polyethylene terephthalate tubular container 2 (manufactured by Sekisui Chemical Co., Ltd., product name: SEPARAPIT TUBE) was provided. An interior of this tubular container 2 was washed with purified water.

A single-dosage of QUICK CHASER HBsAg (manufactured by Mizuho Meddy Co., Ltd., 6 cm long reagent for HBs antigen detection), as the test reagent 3, was secured onto an inner wall of the tubular container 2 with the aid of a pressure-sensitive adhesive tape. An upper portion of the blood test reagent 3 was covered with a protective layer, in the form of a polyethylene terephthalate film (3 cm wide and 6 cm long), to leave its lower 1 cm length portion uncovered. In this case, the protective layer 132 was secured to a surface of the blood test reagent 3 by a pressure-sensitive adhesive tape.

5 mg of EDTA, as the anti-coagulant, was introduced into the tubular container 131 which was subsequently closed by the stopper 5.

A blood sample was collected by an injector from each of the subjects, A, B and C. 2 ml of each blood sample collected was injected into the blood test container of the present Example which was subsequently left to stand for 40 minutes. The following observation of the blood test reagent 3 resulted in proving HBs antigen negative for all the blood samples from the subjects, A, B and C.

Example 41

The blood test container 131 shown in FIG. 55 was assembled in the same manner as in Example 40. However, the stopper 5 was placed on the tubular container at 0.56 atmospheric pressure by using a vacuum capping machine VS-150A (manufactured by Kyowa Shinku, Co., Ltd.). As a result, the blood test container was assembled in such a configuration as to permit vacuum collection of 2 ml blood.

Thereafter, a blood sample from each of the subjects, A, B and C, was vacuum introduced into the above-assembled blood test container which was subsequently left to stand for 40 minutes. The subsequent observation of the blood test reagent 3 resulted in proving HBs antigen negative for all the blood samples from the subjects, A, B and C.

UTILITY IN INDUSTRY

For the blood test container according to the present invention, the blood test reagent is secured within the closed-bottom tubular container. Therefore, blood test results can be immediately obtained by (1) introducing blood or its component into the blood test container where it is allowed to contact the blood test reagent, or alternatively, (2) introducing the blood into the blood test container and centrifuging whereby its component, such as serum or plasma, is allowed to the blood test container.

Conventional blood test methods have required complex procedure involving collecting and centrifuging the blood to separate out the serum or plasma, and taking it up and transferring dropwise onto a reagent by using a dropping pipet. This has also imposed a risk for a tester to contact the blood. In contrast, the use of the blood test container according to the present invention not only simplifies the blood test procedure but also substantially eliminates the risk for a tester to contact the blood. This assures the efficient and safe blood testing.

The invention further includes the contact control structure effective to normally prevent the contact of blood introduced into the tubular container with the test reagent and, when centrifuged, allow a component of the blood to contact the test reagent. This arrangement permits the efficient and safe testing, as well as assuring contact of serum or plasma alone with the test reagent leading to the increased accuracy of blood testing.

In accordance with the invention, the aforementioned contact control structure is configured to include the inner container portion and the solid member. Accordingly, the blood introduced into the inner tubular container, prior to being centrifuged, is blocked by the solid member to stay within an interior of the inner container portion and prevented from contacting the test reagent. When centrifuged, the solid member is forced to fall down to allow the then separated serum or plasma to successfully contact the test reagent secured onto the inner face of the tubular container and/or the outer face of the inner container portion.

In accordance with the invention, the contact control structure is configured to include the tubular member accommodated in the tubular container and the annular member. Accordingly, when introduced into the tubular member, the blood is initially restricted by the annular member from flowing toward the test reagent. When centrifuged, the blood is forced to move from the tubular member toward the tubular container while pushing up the annular member, so that the then separated serum or plasma is allowed to successfully reach and contact the test reagent.

In accordance with the invention, the contact control structure is configured to include a tubular member accommodated in the tubular container and having a bottom end brought into contact with an interior bottom face of the tubular container, and a pressing means for pressing the tubular member against the interior bottom face of the tubular container so that the blood introduced into the tubular member is prevented from leaking therefrom. Accordingly, when introduced into the tubular member, the blood is prevented from leaking therefrom toward the tubular container. When centrifuged, the blood, while separated into serum or plasma and solid matter, is forced to escape toward the tubular container where the separated serum or plasma is allowed to successfully contact the test reagent.

In accordance with the invention, the contact control structure is configured to include the tubular member secured onto the inner face of the tubular container, the test reagent fixedly accommodated in the tubular member, and the solid member located below the test reagent and designed to fall down when centrifuged. Accordingly, when introduced into the tubular container, the blood is prevented from flowing into the tubular member. When subsequently centrifuged, the solid member is forced to fall down while the blood is separated into serum or plasma and solid matter, so that the serum or plasma is permitted to easily flow into the tubular member for contact with the test reagent.

In accordance with the invention, for the blood test container according to the invention as recited in claim 4, the annular member is mounted between the outer face of the tubular member and the inner face of the tubular container with the aid of paraffin. When heated after centrifugation, the paraffin is caused to melt. It then becomes difficult for the annular member to restrict the movement of the serum or plasma. As a result, the serum or plasma, while pushing up the annular member, reaches the test reagent for contact therewith.

For the blood test container according to the invention, the space defined between the tubular container and the second tubular container, inclusive of the region where the blood test reagent is secured, is sealed by the sealing member comprised of thixotropic material having a viscosity of 5,000–500,000 centipoise at 25° C. The blood sample is first introduced into the second tubular and then centrifuged. During the centrifugation, the thixotropic sealing member is forced to move down toward the bottom of the tubular container, thereby opening the space. When the blood test container is subsequently turned upside down, the separated serum or plasma is allowed to enter the space to successfully contact the blood test reagent.

In accordance with the invention, the provision of the contact control structure assures that the blood introduced is initially prevented from contacting the test reagent and the serum or plasma separated by the subsequent centrifugation is allowed to contact the test reagent. This leads to the practice of blood testing with increased precision.

In accordance with the invention, the aforementioned contact control structure includes the flexible inner resin tube accommodated in the tubular container. The inner tube has a peripheral surface portion brought into close contact with an inner face of the tubular container. One end portion of the inner tube has an outer diameter made smaller than an inner diameter of the tubular container so that its peripheral surface is spaced from the inner face of the tubular container. Accordingly, prior to being centrifuged, the blood is prevented from contacting the test reagent by the close contact of the outer face of the inner tube and the inner face of the tubular container. When centrifuged, the communicating member is forced to shift in location to act to release the close contact of the outer face of the inner tube and the inner face of the tubular container, thereby assuring the contact of the serum or plasma with the blood test reagent.

In accordance with the invention, the top and bottom ends of the aforementioned inner tube is opened and an outer diameter of the top end is made smaller than the inner diameter of the tubular container such that the blood, when introduced into the inner tube, is permitted to pass through the bottom opening of the inner tube down toward the bottom portion of the tubular container where it is stored. Accordingly, when centrifuged, the communicating is forced to shift in location to act to release the close contact of the outer face of the inner tube and the inner face of the tubular container, thereby assuring the contact of the separated serum or plasma with the blood test reagent.

In accordance with the invention, the inner tube is closed at its bottom and its outer peripheral surface adjacent the bottom is made smaller than the inner diameter of the tubular container to thereby space it from the inner face of the tubular container. On the other hand, the upper portion of the inner tube has an outer peripheral surface brought into close contact with the inner face of the tubular container so that the blood, when introduced into the inner tube, is prevented from contacting the blood test reagent. Accordingly, when the above-described blood test container is turned upside down, the subsequent centrifuging forces the communicating member to shift in location toward the top of the tubular container, whereby the close contact of the outer face of the inner tube and the inner face of the tubular container is released to allow the separated serum or plasma to successfully contact the blood test reagent.

For the blood test container according to the invention, the second tubular container is accommodated in the tubular container and secured to the inner face of the tubular container and/or the outer face of the second tubular container. Accordingly, in an exemplary case where the stopper is used to close the top opening, when the blood test container is turned upside down, the blood sample leaves from the interior of the second tubular container to enter the space between the first and second tubular containers where it is contacted with the test reagent.

In accordance with the invention, the contact control structure includes the second tubular container accommodated in the tubular container and having at its bottom a plurality of through-holes with diameters of 0.1–10 $\mu$m. Before centrifugation, the blood introduced into the second tubular container hardly leaks therefrom toward the tubular container so that its contact with the reagent is prevented. When centrifuged, the serum or plasma is forced to pass through the plurality of through-holes of the second tubular container and enter the tubular container, while the clot is retained to stay within the second tubular container. Thus, after centrifugation, the serum or plasma is allowed to successfully contact the test reagent.

In accordance with the invention, the contact control structure includes the second tubular container provided at its bottom with a plurality of 10–400 $\mu$m diameter through-holes which prevent immediate passage of the blood when introduced into the second tubular container toward the tubular container. Accordingly, the blood, prior to be centrifuged, is prevented from contacting the test reagent. The subsequent centrifuging forces the blood in the second tubular container to flow into the tubular container while separating the blood into serum or plasma and solid matter. As a result, the serum or plasma separated by the centrifugation is allowed to contact the test reagent.

For the blood test container according to the invention, the space between the tubular container and the second tubular container, inclusive of the region where the blood test reagent is secured, is sealed by the sealing member comprised of the water-soluble material or the material having a melting point of not below 40° C. The blood, when introduced into the blood test container, is thus prevented from accidentally flowing into the space between the tubular container and the second tubular container. After the blood sample is introduced into the second tubular container, the blood test container is turned upside down. The blood sample is allowed to contact the test reagent if the blood test container is simply left to stand according to the invention, or if the blood test container is heated to 40° C. or higher according to the invention.

For the blood test container according to the invention, the blood sample can be brought into the aforementioned space for contact with the test reagent by introducing the blood into the second tubular container, turning the blood test container upside down, and then rotating the stopper to a position where the grooves on the first and second stopper portions are aligned with each other.

In accordance with the invention, the opening of the second tubular container is sealed by the polymer or metal film having a thickness up to 100 $\mu$m. By partly breaking the polymer or metal film using a needle or sharp-edged cutter, the blood can be introduced into the second tubular container without fail and prevented from entering the aforementioned space.

When the blood test container is turned upside down, the blood sample is caused to enter the space between the tubular container and the second tubular container and successfully contact the blood test reagent.

In accordance with the invention, the opening of the second tubular container is sealed by the membrane formed of material having a melting point of not below 40° C. Such a membrane, when partly broken, provides a passage through which the blood can be introduced as by using a tubular member. This prevents the blood sample from entering the space between the tubular container and the second tubular container. Thereafter, the blood test container is turned upside down and then heated to a temperature of 40° C. or higher at which the membrane is caused to melt. As a result, the blood sample is allowed to immediately enter the space and successfully contact the blood test reagent.

For the blood test container according to the invention, the serum or plasma separating medium is accommodated in the second tubular container. Due to the presence of the separating medium, the blood, when centrifuged, can be separated successfully into the serum or plasma which is duly brought into contact with the blood test reagent for reaction therewith.

For the blood test container according to the invention, the second tubular container is provided with the trap portion for trapping erythrocyte and adjacent the trap portion with the hemocyte separating portion having a plurality of 0.1–20 $\mu$m diameter through-holes. The blood is introduced into the second tubular container and then centrifuged. During the centrifugation, the serum or plasma is forced to pass through the through-holes and leave the trapping portion while the erythrocyte, because of its high specific gravity, is retained within the trapping portion. As a result, the serum or plasma is caused to leave the trapping portion and enter the space, between the second tubular container and tubular container, where it successfully contacts the blood test reagent.

For the blood test container according to the invention, the second tubular container is provided at its bottom portion with a plurality of through-holes. Further, the layer comprised of 0.1–200 $\mu$m hydrophilic fine particles is placed to overlie the bottom portion. When a blood sample is introduced into the second tubular container and subsequently centrifuged, the separated serum or plasma is caused to flow into the space between the second tubular container and the tubular container. On the other hand, the hemocyte is retained within the second tubular container to overlie the hydrophilic fine particle layer. As a result, the serum or plasma alone can be brought into contact with the blood test reagent.

In the case where the centrigation is not performed, the blood is vacuum collected by reducing the interior pressure of the blood test container. This pressure reduction creates a suction force which acts to filter the serum or plasma through the hydrophilic fine particle layer. As a result, the serum or plasma alone can be brought into contact with the blood test reagent, as similar to the case as described above.

The second tubular container for use in the invention can be easily fabricated by securing the bottom member having a plurality of through-holes to the tubular member.

In accordance with the invention, for the blood test container according to the invention, the second tubular container is at its bottom apertured to provide a hole and the water-soluble cover member is secured to the bottom of the second tubular container for closing the hole. The blood, when introduced into the second tubular container, is initially prevented from contacting the blood test reagent due to the presence of the water-soluble cover member which closes the hole provided in the bottom of second tubular container.

With the lapse of time, or after centrifugation, the water-soluble cover member is induced to dissolve into the water content of the blood, serum or plasma. As a result, the blood, serum or plasma is allowed to come into contact with the blood test reagent.

In accordance with the invention, the hole provided in the bottom of second tubular container is closed by the cover member formed of a metal or magnet. The blood, when introduced into the second tubular container, is thus prevented from contacting the blood test reagent. The bottom hole of the second tubular container can be opened when the cover member is caused to shift in location by using an external metal or magnet. This permits the blood introduced into the second tubular container or the serum or plasma separated by subsequent centrifugation to pass through the bottom hole and enter the space between the second tubular container and the tubular container. As a result, the blood, serum or plasma is allowed to come into contact with the blood test reagent.

In accordance with the invention, a portion of the blood test container is exposed and the remaining portion is covered with the protective film. This arrangement is effective in preventing undesired swelling of the blood test reagent.

In the blood test container according to the invention, the blood introduced into the tubular container or the serum or plasma separated by the subsequent optional centrifuging can be brought into contact with a part of the blood test reagent by the downward shift of the sliding switch. This eliminates the procedure to distribute the centrifugally separated serum or plasma into test cups, extremely reduces a risk for a tester to contact the blood, and increases the blood testing efficiency.

In accordance with the invention, the tube has a bottom end located at a position below the lowest position that the sliding switch can assume. The blood, when introduced into the tube, is thus prevented from reaching the sliding switch mounted on a side wall of the tubular container. Even in the case where the tubular container is provided with an elongated cutout or the like for slidable movement of the sliding switch therealong, the blood is prevented from leaking through the cutout to outside, thereby assuring the increased safety.

For the blood test container according to the invention, the closed-bottom second tubular container is provided to accommodate the tubular container and the sliding switch mounted thereon and these two tubular containers are reduced in interior pressure. Accordingly, the blood can be quickly collected in the tubular container according to the vacuum blood collection procedure. After collection of the blood, or after optionally-followed centrifugation that separates the serum or plasma from the blood, the second tubular container is removed. Thereafter, the blood test procedure used for the blood test container is followed.

Therefore, the whole procedure starting from blood collection and ending with measurement of various blood components can be safely carried out without a risk for a tester to contact the blood.

In accordance with the invention, the blood test container-according to the invention is reduced in interior pressure. Accordingly, the blood can be easily introduced into the blood test container according to the vacuum blood collection procedure.

With the use of the blood test container according to the invention, the whole procedure starting from blood collection and ending with measurement of various blood components can thus be easily and precisely carried out without a risk for a tester to directly contact the blood.

When the blood test method according to the invention is followed, the whole procedure starting from blood collection and ending with measurement of various blood components can be easily and precisely carried out without a risk for a tester to directly contact the blood.

When the blood test method according to the invention is followed, the whole procedure starting from blood collection and ending with measurement of various blood components can be easily and precisely carried out without a risk for a tester to directly contact the blood.

What is claimed is:

1. A blood test container, comprising:
   a closed-bottom tubular container and a blood test reagent secured within the tubular container, and a contact control structure which includes:
   a flexible inner resin tube accommodated in the tubular container and having a peripheral surface portion brought into close contact with an inner face of the tubular container and an end portion dimensioned to have an outer diameter smaller than an inner diameter of the tubular container so that its peripheral surface is spaced from the inner face of the tubular container to provide an enclosed space preventing fluid communication therebetween; and
   a communicating member disposed within said space so as to be moveable to allow fluid communication in said space,
   wherein said blood test reagent is enclosed within the space and secured onto either the inner face of the tubular container or the outer face of the inner tube.

2. The blood test container as recited in claim 1, wherein said inner tube is opened at its top and bottom ends and an outer diameter of said top end is made smaller than the inner diameter of the tubular container.

3. The blood test container as recited in claim 1, wherein said inner tube has a closed bottom and an outer diameter of its portion adjacent the bottom is made smaller than the inner diameter of the tubular container.

4. The blood test container as recited in claim 1, wherein an interior of the blood test container is reduced in pressure.

5. The blood test method characterized as comprising, in sequence, introducing blood into the blood test container as recited in claim 1 and allowing the blood or its component to contact said blood test reagent.

6. A blood test method characterized as comprising, in sequence, introducing blood into the blood test container as recited in claim 1 and, subsequent to centrifugation thereof, allowing a component of the blood to contact said blood test reagent.

7. A blood test container as recited in claim 1 wherein the test reagent is for immunochromatography and is fixed within said tubular container.

8. A blood test container as recited in claim 7, wherein a portion of said test reagent for immunochromatography is exposed and the remaining portion thereof is covered with a protective layer so that the contact of the test reagent for immunochromatography with blood or the like is prevented at the remaining portion.

9. A blood test container, comprising:
   a closed-bottom tubular container and a blood test reagent secured within the tubular container; and
   a bottom-closed second tubular container, having a smaller diameter than said tubular container, being provided at its bottom with a plurality of through-holes having diameters of 0.1–10 μm, and being accommodated within the tubular container,
   wherein said blood test reagent is provided on at least one of the inner face of the tubular container and the outer face of the second tubular container.

10. A blood test container, comprising:
    a closed-bottom tubular container and a blood test reagent secured within the tubular container; and
    a bottom-closed second tubular container, having a smaller diameter than said tubular container, being provided at its bottom with a plurality of through-holes having diameters of 10–400 μm, and being accommodated within the tubular container,
    wherein said blood test reagent is provided on at least one of the inner face of the tubular container and the outer face of the second tubular container, and a porous region including said plurality of through-holes is located at a position below said test reagent.

11. The blood test container as recited in any one of claims 9–10, characterized as further containing a serum or plasma separating medium accommodated in said second tubular container.

12. A blood test container, comprising:
    a closed-bottom tubular container and a blood test reagent secured within the tubular container; and
    a bottom-closed second tubular container having a smaller diameter than said tubular container and accommodated within the tubular container,
    wherein said blood test reagent is provided on at least one of the inner face of the tubular container and the outer face of the second tubular container, and said second tubular container has at its bottom a downwardly-projecting trap portion, constructed for trapping erythrocytes, and is disposed adjacent to, and lower than a hemocyte separating portion having a plurality of through-holes 0.1–20 μm in diameter.

13. A blood test container, comprising:
    a closed-bottom tubular container and a blood test reagent secured within the tubular container; and
    a bottom-closed second tubular container having a smaller diameter than said tubular container and accommodated within the tubular container,
    wherein said blood test reagent is provided on at least one of the inner face of the tubular container and the outer face of the second tubular container, and said second tubular container has at its bottom a plurality of through-holes and that a layer comprised of 0.1–200 μm hydrophilic fine particles is disposed to overlie said through-holes.

14. The blood test container as recited in claim 13, characterized that said second tubular container includes a tubular member opened at its both ends and a bottom member secured onto the bottom end of the tubular member and having said plurality of through-holes.

* * * * *

UNITED STATES PATENT AND TRADEMARK OFFICE
CERTIFICATE OF CORRECTION

PATENT NO. : 6,793,885 B1
DATED : September 21, 2004
INVENTOR(S) : Masayuki Yokoi et al.

It is certified that error appears in the above-identified patent and that said Letters Patent is hereby corrected as shown below:

<u>Title page,</u>
Item [73], Assignee, insert -- Sekisui Chemical Co., Ltd., Osaka Japan --

Signed and Sealed this

Fifth Day of July, 2005

JON W. DUDAS
*Director of the United States Patent and Trademark Office*